United States Patent [19] [11] 4,248,999
Baba et al. [45] Feb. 3, 1981

[54] 5-FLUOROURACIL DERIVATIVES AND PROCESS FOR PREPARING THEREOF

[75] Inventors: Tsuneo Baba, Fukuoka; Masakatsu Kaneko, Hiromachi; Bunji Shimizu, Hiromachi; Masao Arakawa, Hiromachi, all of Japan

[73] Assignee: Sankyo Company Limited, Tokyo, Japan

[21] Appl. No.: 847,452

[22] Filed: Oct. 31, 1977

[30] Foreign Application Priority Data

Oct. 28, 1976 [JP] Japan .................. 51-130200
Apr. 15, 1977 [JP] Japan .................. 52-43214
May 20, 1977 [JP] Japan .................. 52-58492
Sep. 13, 1977 [JP] Japan .................. 52-110370
Sep. 14, 1977 [JP] Japan .................. 52-110867

[51] Int. Cl.³ ............... C07H 17/02; A61K 31/70
[52] U.S. Cl. .......................... 536/4; 536/18; 424/180
[58] Field of Search ..................... 536/18, 4

[56] References Cited

U.S. PATENT DOCUMENTS 3,016,372  1/1962  Krimmel .................. 536/4
4,074,042  2/1978  Watanabe et al. ......... 536/18

FOREIGN PATENT DOCUMENTS 130200  10/1976  Japan .................. 536/4

OTHER PUBLICATIONS

Johnson et al., "Cancer Treatment Reviews," vol. 2, 1975, pp. 1–31.

Primary Examiner—Johnnie R. Brown
Attorney, Agent, or Firm—Frishauf, Holtz, Goodman & Woodward

[57] ABSTRACT

5-Fluorouracil compounds having a glycoside substituent connected to the 5-fluorouracil nucleus through a bridging oxygen atom; and having anti-tumor activity.

18 Claims, No Drawings

5-FLUOROURACIL DERIVATIVES AND PROCESS FOR PREPARING THEREOF

FIELD OF INVENTION

This invention relates to 5-fluorouracil derivatives characterized by excellent anti-tumor activity.

BACKGROUND OF THE INVENTION

Heretofore, a glycoside compound in which a heterocyclic base is connected with a saccharide through an oxygen atom is unstable against an alkali and, particularly, an O-glycoside in which the protective groups of the saccharide moiety are completely removed has never been isolated.

SUMMARY OF THE INVENTION

Novel and valuable compounds characterized by excellent anti-tumor activity, as contemplated herein, are selected from the following:

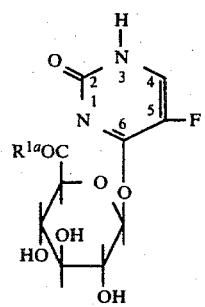
(Ia)

wherein $R^{1a}$ represents hydroxy, alkoxy, cycloalkoxy, aralkyloxy, aryloxy or

in which $R^{2a}$ and $R^{3a}$ may be the same or different and each represents hydrogen, alkyl, cycloalkyl, aralkyl, aryl, or $R^{2a}$ and $R^{3a}$ may form, together with the adjacent nitrogen atom, a cyclic imino group;

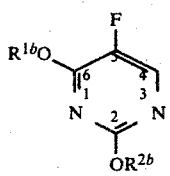
(Ib)

wherein $R^{1b}$ and $R^{2b}$ are the same and can each represent β-D-glucopyranosyl, β-D-galactopyranosyl, β-D-ribopyranosyl or β-D-xylopyranosyl, or one of $R^{1b}$ and $R^{2b}$ represents β-D-glucopyranosyl, β-D-galactopyranosyl, β-D-ribopyranosyl or β-D-xylopyranosyl and the other of $R^{1b}$ and $R^{2b}$ is hydrogen;

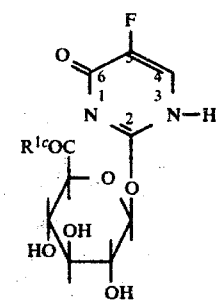
(Ic)

wherein $R^{1c}$ represents hydroxy, alkoxy, cycloalkoxy, aralkyloxy, aryloxy or

in which $R^{2c}$ and $R^{3c}$ may be the same or different and each represents hydrogen, alkyl, cycloalkyl, aralkyl, aryl, or $R^{2c}$ and $R^{3c}$ may form, together with the adjacent nitrogen atom, a cyclic imino group;

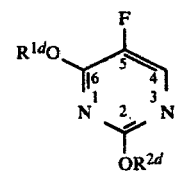
(Id)

wherein one of $R^{1d}$ and $R^{2d}$ represents a group of the formula

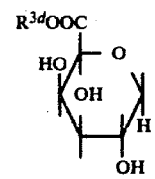

in which $R^{3d}$ represents hydrogen, alkyl, cycloalkyl, aralkyl or aryl, and the other of $R^{1d}$ and $R^{2d}$ is hydrogen; and

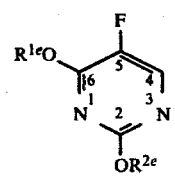
(Ie)

wherein one of $R^{1e}$ and $R^{2e}$ represents a group of the formula

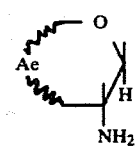

wherein Ae is a group of one of the following formulae

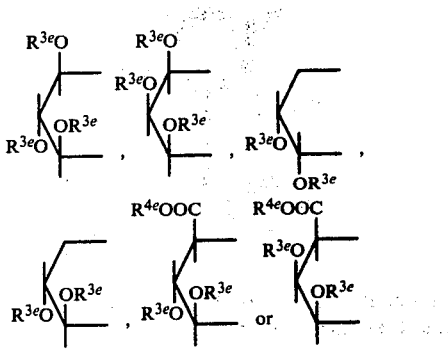

in which $R^{3e}$ is hydrogen or acyl, $R^{4e}$ is hydrogen, alkyl, cycloalkyl, aralkyl or aryl, and the other of $R^{1e}$ and $R^{2e}$ is hydrogen.

SPECIFIC EMBODIMENTS OF THE INVENTION

COMPOUNDS (Ia)

As indicated above, 5-fluorouracil compounds contemplated herein include those represented by the following formula

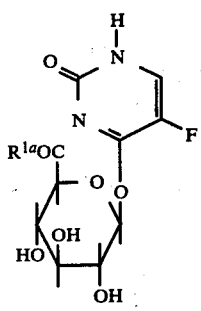

(Ia)

In the above formula, $R^{1a}$ represents a hydroxyl group, an alkoxy group, a cycloalkoxy group, an aralkyloxy group, an aryloxy group or a group

in which $R^{2a}$ and $R^{3a}$ may be the same or different and each represents a hydrogen atom, an alkyl group, a cycloalkyl group, an aralkyl group or an aryl group; or $R^{2a}$ and $R^{3a}$ may form, taken together with the adjacent nitrogen atom, a cyclic amino group.

In formula (Ia) mentioned above, $R^{1a}$ represents a hydroxyl group; a straight-chain or branched alkoxy group having 1 to 8 carbon atoms, e.g., methoxy, ethoxy, n-propoxy, isopropoxy, n-butoxy, isobutoxy, n-pentyloxy, isopentyloxy, n-hexyloxy, sec-hexyloxy, n-heptyloxy, n-octyloxy, 2-ethyl-hexyloxy, etc.; a cycloalkoxy group having 5 to 7 ring members, e.g., cyclopentyloxy, cyclohexyloxy, cycloheptyloxy, etc.; an aralkyloxy group, the aromatic ring of which may be unsubstituted, e.g., benzyloxy, phenethyloxy, etc., or substituted with a lower alkyl group such as methyl, ethyl, n-propyl, isopropyl, n-butyl and isobutyl, a lower alkoxy group such as methoxy, ethoxy, n-propoxy, isopropoxy, n-butoxy and isobutoxy, or a halogen atom such as chlorine, bromine and fluorine; an aryloxy group, the aromatic ring of which may be unsubstituted or substituted with a lower alkyl group such as methyl, ethyl, n-propyl, isopropyl, n-butyl and isobutyl, a lower alkoxy group such as methoxy, ethoxy, n-propoxy, isopropoxy, n-butoxy and isobutoxy, or a halogen atom such as chlorine, bromine and fluorine e.g., phenyloxy etc.; or a group

in which $R^{2a}$ and $R^{3a}$ may be the same or different and each represents a hydrogen atom; a straight-chain or branched alkyl group having 1 to 5 carbon atoms, e.g., methyl, ethyl, n-propyl, isopropyl, n-butyl, isobutyl, n-pentyl, isopentyl, etc.; a cycloalkyl group having 5 to 7 ring members, e.g., cyclopentyl, cyclohexyl, cycloheptyl, etc.; an aralkyl group, the aromatic ring of which may be unsubstituted or substituted with a lower alkyl group such as methyl, ethyl, n-propyl, isopropyl, n-butyl and isobutyl, a lower alkoxy group such as methoxy, ethoxy, n-propoxy, isopropoxy, n-butoxy and isobutoxy, or a halogen atom such as chlorine, bromine and fluorine, e.g., benzyl, phenethyl, etc.; an aryl group, the aromatic ring of which may be unsubstituted, e.g., phenyl, etc., or substituted with a lower alkyl group such as methyl, ethyl, n-propyl, isopropyl, n-butyl and isobutyl, a lower alkoxy group such as methoxy, ethoxy, n-propoxy, isopropoxy, n-butoxy and isobutoxy, or a halogen atom such as chlorine, bromine and fluorine; or $R^{2a}$ and $R^{3a}$ may form, taken together with the adjacent nitrogen atom, a 5 to 6 membered-cyclic amino group, e.g., 1-pyrrolidinyl, piperidino, morpholino, etc.

Further, in formula (Ia) mentioned above, $R^{1a}$ preferably represents a hydroxyl group; a straight-chain or branched alkoxy group having 1 to 8 carbon atoms; an amino group; a straight-chain or branched alkylamino or dialkylamino group having 1 to 5 carbon atoms; a benzylamino group; and a cyclic amino group having 5 to 6 ring members.

We have made extensive studies concerning 5-fluorouracil compounds for the purpose of developing an anti-tumor agent having little side-effect. As a result of this, we have found that $O^4$-glucuronides of 5-fluorouracil of formula (Ia) mentioned above have excellent anti-tumor activity and low toxicity.

As the compounds of formula (Ia) mentioned above, the following are illustrative:

1a     1-(5-Fluoro-1H-2-oxo-pyrimidin-4-yl)-β-D-glucopyranouronic acid
2a     1-(5-Fluoro-1H-2-oxo-pyrimidin-4-yl)-β-D-glucopyranouronic acid methyl ester
3a     1-(5-Fluoro-1H-2-oxo-pyrimidin-4-yl)-β-D-glucopyranouronic acid ethyl ester
4a     1-(5-Fluoro-1H-2-oxo-pyrimidin-4-yl)-β-D-glucopyranouronic acid n-propyl ester
5a     1-(5-Fluoro-1H-2-oxo-pyrimidin-4-yl)-β-D-glucopyranouronic acid isopropyl ester
6a     1-(5-Fluoro-1H-2-oxo-pyrimidin-4-yl)-β-D-glucopyranouronic acid n-butyl ester
7a     1-(5-Fluoro-1H-2-oxo-pyrimidin-4-yl)-β-D-glucopyranouronic acid isobutyl ester 8a 1-(5-Fluoro-1H-2-oxo-pyrimidin-4-yl)-β-D-gluoc-pyranouronic acid n-pentyl ester
9a 1-(5-Fluoro-1H-2-oxo-pyrimidin-4-yl)-β-D-glucopyranouronic acid n-hexyl ester
10a 1-(5-Fluoro-1H-2-oxo-pyrimidin-4-yl)-β-D-glucopyranouronic acid n-heptyl ester
11a 1-(5-Fluoro-1H-2-oxo-pyrimidin-4-yl)-β-D-glucopyranouronic acid n-octyl ester
12a 1-(5-Fluoro-1H-2-oxo-pyrimidin-4-yl)-β-D-glucopyranouronic acid amide
13a 1-(5-Fluoro-1H-2-oxo-pyrimidin-4-yl-β-D-glucopyranouronic acid dimethylamide
14a 1-(5-Fluoro-1H-2-oxo-pyrimidin-4-yl)-β-D-glucopyranouronic acid diethylamide
15a 1-(5-Fluoro-1H-2-oxo-pyrimidin-4-yl)-β-D-glucopyranouronic acid n-propylamide
16a 1-(5-Fluoro-1H-2-oxo-pyrimidin-4-yl)-β-D-glucopyranouronic acid isopropylamide
17a 1-(5-Fluoro-1H-2-oxo-pyrimidin-4-yl)-β-D-glucopyranouronic acid n-butylamide
18a 1-(5-Fluoro-1H-2-oxo-pyrimidin-4-yl)-β-D-glucopyranouronic acid isobutylamide
19a 1-(5-Fluoro-1H-2-oxo-pyrimidin-4-yl)-β-D-glucopyranouronic acid n-pentylamide
20a 1-(5-Fluoro-1H-2-oxo-pyrimidin-4-yl)-β-D-glucopyranouronic acid benzylamide
21a 1-[1-(5-Fluoro-1H-2-oxo-pyrimidin-4-yl)-β-D-glucopyranouronoyl]-pyrrolidine
22a 1-[1-(5-Fluoro-1H-2-oxo-pyrimidin-4-yl)-β-D-glucopyranouronoyl[-piperidine
23 a 4-[1-(5-Fluoro-1H-2-oxo-pyrimidin-4-yl)-β-D-glucopyranouronoyl]-morpholine The compunds of this invention, formula (Ia), can be prepared by the processes illustrated below.

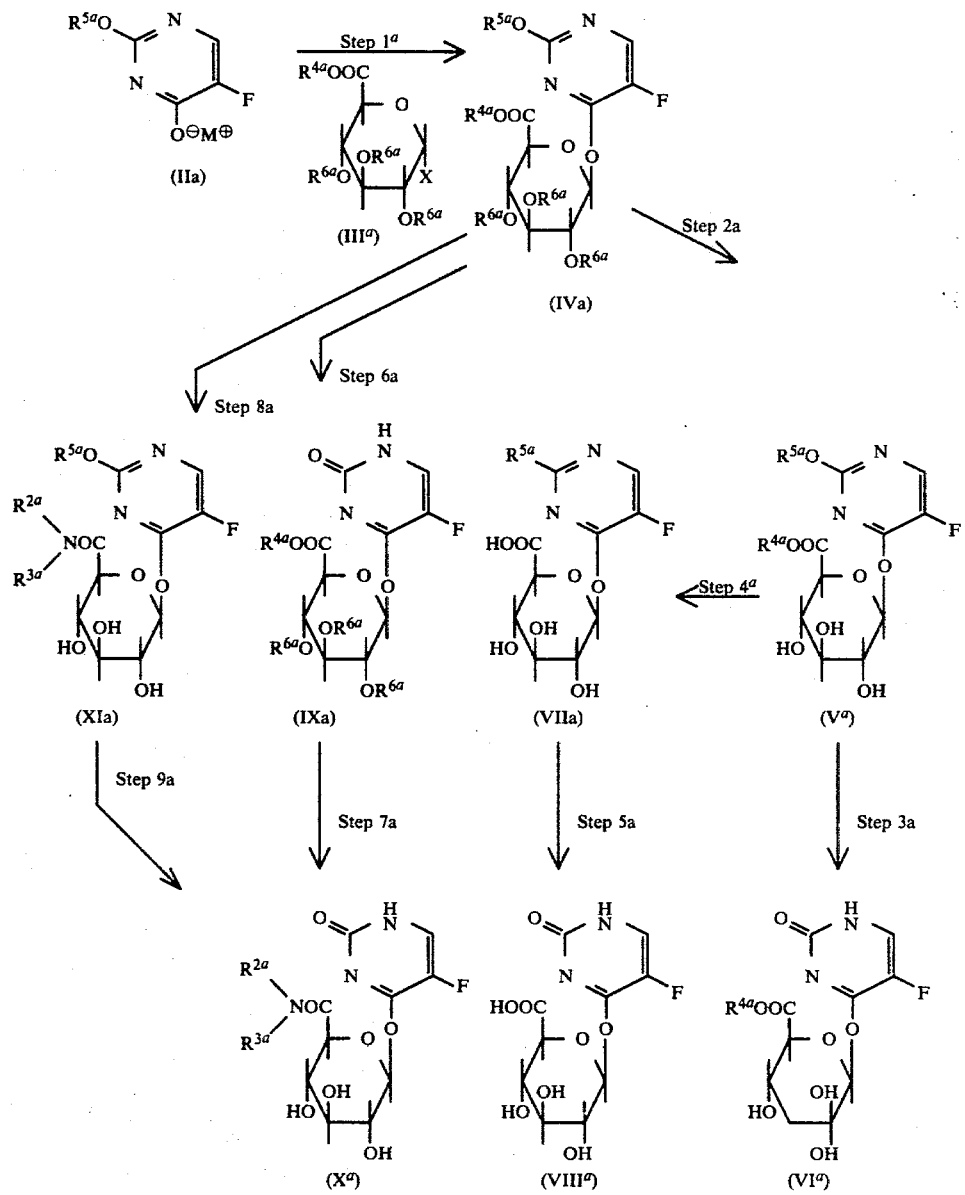

In the above formulae, $R^{2a}$ and $R^{3a}$ have the same meanings as defined hereinbefore; $R^{ra}$ represents an alkyl group, a cycloalkyl group, an aralkyl group or an aryl group, each corresponding to a group $R^{1a}OC-$ in general formula (Ia) mentioned above which represents a carboxylic acid ester group; $R^{5a}$ represents a protective group for a hydroxyl group which may be removed by reduction reaction, e.g., a benzyl group, the aromatic ring of which may be unsubstituted or substituted with a nitro group, a halogen atom such as chlorine, bromine and fluorine, or an ethyl group substituted at the β-position with one or more halogen atoms such as 2,2,2-trichloroethyl, 2,2-dibromoethyl, etc.; $R^{6a}$ represents an acyl group which may be employed as a protective group for a hydroxyl group, e.g., an aliphatic acyl group such as acetyl, n-propionyl, n-butyryl and isobutyryl, or an aromatic acyl group such as benzoyl, p-nitrobenzoyl, p-methylbenzoyl and p-methoxybenzoyl, etc.; an ion $M^{\oplus}$ represents a metal ion which may be employed in the reaction for preparing an O-glycoside compound by condensation of a heterocyclic base and a saccharide, e.g., a monovalent silver ion, a monovalent mercury ion, a divalent mercury ion as in HgCl and HgBr$_2$, an alkali metal ion such as a sodium ion, a potassium ion and the like, etc.; and X represents a halogen atom, e.g., chlorine, bromine, etc.

The first step is to prepare an O-glycoside compound of formula (IVa) mentioned above; a metal salt of 5-fluorouracil of formula (IIa) is subjected to condensation reaction with a halogenoglucopyranouronic acid ester derivative of formula (IIIa).

In carrying out the condensation reaction, a compound of formula (IIa) is contacted with a compound of formula (IIIa) in the presence of a solvent.

As the solvents to be used, though not limited in particular as long as they do not participate in the condensation reaction, there are preferred aromatic hydrocarbons, e.g., toluene, xylene, etc.; dialkyl aliphatic acid amides, e.g., dimethylformamide, dimethylacetamide, etc.; dialkylsulfoxides, e.g., dimethylsulfoxide etc.; phosphoric acid amides, e.g., hexamethylphosphoroamide etc.; nitroalkanes, e.g., nitromethane etc.; and nitriles, e.g., acetonitrile. While the reaction temperature is not limited in particular, the reaction is carried out generally at 0°–150° C., but preferably at 100°–150° C. when a nonpolar solvent is used and at around room temperature when a polar solvent is used. The reaction period varies depending mainly upon the reaction temperature and the solvent to be used, but it is between around 5 minutes and 20 hours.

The condensation reaction may also be conducted by a process which comprises, instead of using a metal salt of formula (IIa), adding mercuric cyanide in the presence of a solvent to a compound of formula (XIIa)

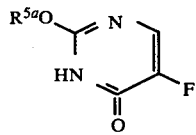

(XIIa)

wherein $R^{5a}$ has the same meaning as defined above, and then a halogenoglucopyranouronic acid of formula (IIIa) mentioned above is added thereto while heating.

After completion of the condensation reaction, desired compound (IVa) is obtained from the reaction mixture according to any ordinary method. For instance, after insoluble substances in the reaction mixture are filtered off, the solvent is removed by distillation under reduced pressure and the residue is extracted with an organic solvent such as chloroform. After the extract is washed with water and dried, the solvent is removed from the extract by distillation, an organic solvent such as ethanol is added to the residue so obtained and the mixture is allowed to stand in an ice room to obtain crystals of the desired compound.

The second step is to prepare a compound of formula (Va) mentioned above; an acyl protective group of a hydroxyl group in a saccharide moiety is removed from a compound of formula (IVa). In carrying out this step, the reaction is conducted by contacting a compound of formula (IVa) with an alkali metal alkoxide in the presence of a solvent. Preferred alkali metal alkoxides are sodium methoxide, sodium ethoxide, potassium tert-butoxide and the like. As the solvents to be used, though not limited as long as they do not participate in the reaction, there may preferable be mentioned alcohols, e.g., methanol, ethanol, tert-butanol, etc.; ethers, e.g., tetrahydrofuran, dioxane, etc.; halogenated hydrocarbons, e.g., methylene chloride, chloroform, etc.; and aromatic hydrocarbons, e.g., benzene, toluene, xylene. While the reaction temperature is not limited in particular, the reaction is carried out generally at −20° to 50° C., but preferably at around 0° C. in particular. The reaction period is different depending mainly upon the reaction temperature but is between around 10 and 60 minutes.

After completion of the reaction, desired compound (Va) is obtained from the reaction mixture according to an ordinary method. For instance, after the reaction mixture is neutralized by adding such an acid as dilute hydrochloric acid thereto and the solvent is removed by distillation, the residue is dissolved in an organic solvent such as chloroform. Then, the organic solvent layer is washed with water and dried. Thereafter the solvent is removed from the extract by distillation and the residue so obtained is purified by fractionation by column chromatography on silica gel. From the thus obtained eluate which contains the desired product is removed the solvent by distillation, to the residue thus produced is added an organic solvent such as ethanol and the resulting mixture is allowed to stand to obtain crystals of the desired product.

The third step is to prepare a uronic acid ester compound of formula (VIa) which is a desired compound of this invention; a protective group of the hydroxyl group in the pyrimidinine nucleus moiety is removed from a compound of formula (Va) by reduction reaction.

In carrying out the reduction reaction, a compound of formula (Va) is contacted with a reducing agent in the presence of a solvent. As the reducing agents, hydrogen and a catalyst for catalytic reduction such as palladium-carbon are preferable in cases where the protective group of the hydroxyl group is a substituted or unsubstituted benzyl group; and metallic zinc and acetic acid or an alcohol such as methanol, ethanol, etc., are preferable in cases where the protective group of the hydroxyl group is an ethyl group substituted at its β-position with one or more halogen atoms. While the solvents to be used are not limited in particular as long as they do not participate in the present reaction, alcohols such as methanol, ethanol, etc., and ethers such as tetrahydrofuran, dioxane, etc., are preferable. The reaction temperature is not limited in particular but the reaction may preferably be carried out at around room temperature. The reaction period varies depending mainly upon the reducing agent but is between around 5 and 60 minutes.

After completion of the reduction reaction, desired compound (VIa) is obtained according to an ordinary method. For instance, after insoluble substances are removed from the reaction mixture, the solvent is removed by distillation under reduced pressure. To the residue thus produced is added an organic solvent such as ethanol and the resulting mixture is allowed to stand to obtain crystals of the desired product.

The fourth step is to prepare a compound of formula (VIIa); an ester compound of formula (Va) is hydrolyzed. In carrying out this step, the reaction is conducted by contacting a compound of formula (Va) with a hydrolyzing agent in the presence of a solvent. While the hydrolyzing agents are not limited in particular if they hydrolyze only an ester group without influencing another part of the compound, the reaction is preferably carried out at around pH 11 by using ammonium hydroxide. As the solvents to be used, while not limited in particular as long as they do not participate in the reaction, a mixed solvent of an alcohol such as methanol, ethanol, etc., and water is preferable. While the reaction temperature is not limited in particular, the reaction is carried out generally at $-10°\sim 50°$ C., but may usually be carried out preferably at around room temperature. The reaction period varies depending mainly upon the reaction temperature, but is between around 3 and 24 hours.

After completion of the reaction, desired compound (VIIa) is obtained according to an ordinary method. For instance, the solvent is removed from the reaction mixture by distillation under reduced pressure and the residue is purified by fractionation by preparative thin layer chromatography on silica gel. The so obtained fraction of the desired compound is extracted with an organic solvent such as methanol and then the solvent is removed by distillation from the extract. After an organic solvent such as ethanol is added to the residue, the mixture is allowed to stand in an ice room to obtain crystals of the desired product.

The fifth step is to prepare a uronic acid compound of formula (VIIIa) which is a desired compound of this invention; a protective group of the hydroxyl group in the pyrimidine nucleus moiety is removed from a compound of formula (VIIa) by reduction reaction. The reduction reaction conditions and the procedures for after-treatment are similar to those in the third step as mentioned above.

The sixth step is to prepare a compound of formula (IXa); a protective group of the hydroxyl group in the pyrimidine nucleus moiety is removed from a compound (IVa) by reduction reaction. The reduction reaction conditions and the procedures for after-treatment are similar to those in the third step as mentioned above.

The seventh step is to prepare a uronic acid amide compound of formula (Xa) which is a desired compound of the present invention; acidamidation is conducted, simultaneously with removing an acyl protective group for the hydroxyl group of the saccharide moiety from a compound of formula (IXa).

In carrying out the reaction of the seventh step, the reaction is conducted by contacting a compound of formula (IXa) with an amine of formula

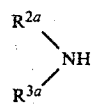

(XIIIa)

wherein $R^{2a}$ and $R^{3a}$ have the same meanings as defined above, in the presence of a solvent. As the solvents to be used, while not limited in particular as long as they do not participate in the reaction, an alcohol such as methanol, ethanol, etc., is preferable. While the reaction temperature is not limited in particular, the reaction is carried out at 0°-100° C., preferably at around room temperature in general. The reaction period varies depending mainly upon the reaction temperature but is between around 3 and 18 hours, preferably between around 12 and 18 hours in cases where the reaction is conducted at room temperature.

After completion of the reaction, desired compound (X) is obtained from the reaction mixture according to an ordinary method. For instance, the solvent is removed from the reaction mixture by distillation under reduced pressure and the desired product can be obtained by adding an organic solvent such as ethanol to the residue so obtained.

The eighth step is to prepare a compound of formula (XIa); acidamidation is conducted, simultaneously with removing an acyl protective group for the hydroxyl group of the saccharide moiety from a compound of formula (IVa).

The reaction conditions of the reaction in the eighth step and the procedures for after-treatment are similar to those in the seventh step as mentioned above.

The ninth step is an alternative process for preparing a uronic acid amide compound of formula (Xa) which is a desired compound of this invention; a protective group for the hydroxyl group on the pyrimidine nucleus moiety is removed from a compound of formula (XIa) by reduction reaction. The reduction reaction conditions for the reaction and the procedures for after-treatment are similar to those in the third step as mentioned above.

Each desired compound which is obtained by the steps mentioned above can, if necessary, be purified further by an ordinary method, e.g., recrystallization or reprecipitation method.

Compounds of formula (Ia) are illustrated below.

EXAMPLE 1a 1-(2-Benzyloxy-5-fluoro-pyrimidin-4-yl)-2,3,4-tri-O-acetyl-β-D-glucopyranouronic acid methyl ester

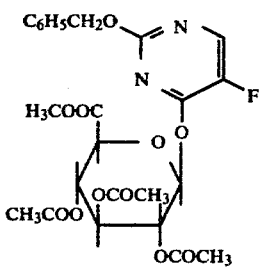

In 320 ml of dry xylene was suspended 7.9 g (24.2 mmol) of 2-benzyl-5-fluorouracil silver salt obtained in Referential Example 1. About 90 ml of the solvent was removed by distillation using a water-separator to remove water in the suspension and the remaining suspension was allowed to cool. To the remaining suspension was added 9.1 g (24.2 mmol) of 1-bromo-1-deoxy-2,3,5-tri-O-acetyl-α-D-glucopyranouronic acid methyl ester and the mixture was refluxed while heating for 5 minutes. After completion of the reaction and allowing the resulting mixture to cool, insoluble substances precipitated. Such substances were filtered off and the solvent was removed by distillation under reduced pressure.

The residue was dissolved in chloroform. The resulting chloroform layer was washed successively with 5% aqueous sodium hydrogen carbonate and 20% aqueous sodium chloride, and the resulting aqueous layers were extracted with chloroform. After the chloroform layers were combined and dried, the solvent was removed therefrom by distillation to obtain a caramel-like residue. To the residue was added ethanol and then the resulting mixture was allowed to stand at 4° C. overnight. 7.3 g of the desired compound, as crystals melting at 120°–121° C., were obtained.

Elementary analysis: for $C_{24}H_{25}O_{11}N_2F$ Calcd. C, 53.73; H, 4.70; N, 5.22; F, 3.54 Found C, 53.94; H, 4.56; N, 5.19; F, 3.48

Ultraviolet absorption spectrum $\lambda_{max}^{0.1\ N\text{-}HCl,\ MeOH}$ 271 nm ($\epsilon$, 8000); $\lambda_{max}^{MeOH}$ 271 nm ($\epsilon$, 7300); $\lambda_{max}^{0.1\ N\text{-}NaOH}$ 270 nm ($\epsilon$, 9000).

EXAMPLE 2a 1-(2-Benzyloxy-5-fluoro-pyrimidin-4-yl)-$\beta$-D-glucopyranouronic acid methyl ester

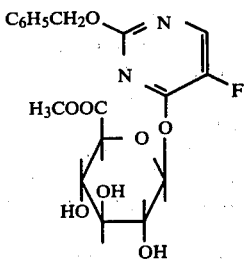

To 70 ml of a mixture of anhydrous methanol and methylene chloride (3:2) was added 6.06 g (11.3 mmol) of 1-(2-benzyloxy-5-fluoro-4-pyrimidin-4-yl)-2,3,4-tri-O-acetyl-$\beta$-D-glucopyranouronic acid methyl ester. After cooling with ice water, 6.6 ml of 1 N methanol solution of sodium methoxide was added thereto, followed by stirring and the resulting mixture was stirred further for 40 minutes at 0° C. After completion of the reaction, 2.5 ml of 1 N hydrochloric acid was added to the reaction mixture for neutralization and the solvent was removed by distillation. After the resulting residue was dissolved in chloroform, the chloroform layer was washed with water and dried over anhydrous magnesium sulfate. Then, the solvent was removed by distillation to obtain 4.46 g of a caramel-like residue. This residue was subjected to column chromatography on 100 g of silica gel using chloroform containing 2.5% of methanol. The solvent of the eluate collected was removed by distillation and the resulting residue, after adding ethanol thereto, was allowed to stand. The crystals precipitated were recovered by filtration to obtain 1.78 g of the desired compound as white crystals melting at 159°–160° C. Further, 540 mg of secondary crystals were obtained from the mother liquor.

Elementary analysis: for $C_{18}H_{19}O_8N_2F$ Calcd. C, 52.68; H, 4.67; N, 6.83; F, 4.63 Found C, 53.05; H, 4.50; N, 6.93; F, 4.41

Ultraviolet absorption spectrum: $\lambda_{max}^{0.1\ N\text{-}HCl}$ 269 nm ($\epsilon$, 7100); $\lambda_{max}^{HO}$ 270 nm ($\epsilon$, 7300); $\lambda_{max}^{0.1\ N\text{-}NaOH}$ 269 nm ($\epsilon$, 7700).

EXAMPLE 3a 1-(5-Fluoro-1H-2-oxo-pyrimidin-4-yl)-$\beta$-D-glucopyranouronic acid methyl ester

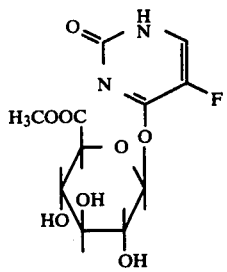

In 100 ml of anhydrous methanol was dissolved 2.03 g (4.95 mmol) of 1-(2-benzyloxy-5-fluoro-pyrimidin-4-yl)-$\beta$-D-glucopyranouronic acid methyl ester. After replacement of the atmosphere in the reaction vessel for reduction with nitrogen gas, 400 mg of 10%-palladium on carbon was added thereto. After replacing the atmosphere again with nitrogen gas, hydrogen gas was introduced with stirring under ordinary pressure for 15 minutes. After completion of the catalytic reduction, insoluble substances were removed from the reaction mixture by filtration and the solvent was removed by distillation under reduced pressure. To the crystals which precipitated were added ethanol and the resulting mixture was filtered. 1.529 g of the desired compound, as white crystals melting at 122°–124° C., were collected.

Elementary analysis: for $C_{11}H_{13}O_8N_2F$. ½ $H_2O$ Calcd. C, 40.13; H, 4.29; N, 8.51; F, 5.77 Found C, 39.97; H, 4.64; N, 8.44; F, 5.47

Ultraviolet absorption spectrum: $\lambda_{max}^{H2O}$ 288 nm ($\epsilon$, 5700)

The crystals were recrystallized from a mixture of anhydrous methanol and ethanol (1:1) to obtain white needles melting at 127°–128° C.

EXAMPLE 4a 1-(2-Benzyloxy-5-fluoro-pyrimidin-4-yl)-$\beta$-D-glucopyranouronic acid

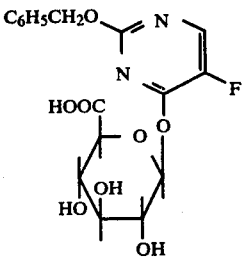

In 23 ml of a mixture of methanol, water and concentrated aqueous ammonia (6:3.9:0.1) was dissolved 1.025 g (2.5 mmol) of 1-(2-benzyloxy-5-fluoro-pyrimidin-4-yl)-$\beta$-D-glucopyranouronic acid methyl ester obtained in Example 2a, and the resulting solution was stirred at room temperature for 24 hours. After completion of the reaction, the solvent was removed by distillation under reduced pressure to obtain 1.2 g of a caramel-like residue. This residue was subjected to preparative thin layer chromatography on silica gel and chloroform containing 35% of methanol was used as an eluent. A fraction containing the desired compound was extracted with methanol and the extract was evaporated to remove the methanol. To the thus obtained caramel-like residue was added ethanol and the resulting mixture was allowed to stand in a refrigerator overnight. Crystals which precipitated were collected by filtration to obtain 724.5 mg of the desired product as white crystals melting at 129°–130° C.

Elementary analysis: for $C_{17}H_{17}O_8N_2F \cdot 2\ H_2O$ Calcd. C, 47.23; H, 4.90; N, 6.48; F, 4.39 Found C, 47.77; H, 4.60; N, 6.39; F, 4.00

Ultraviolet absorption spectrum: $\lambda_{max}^{pH\ 4.01}$ 269 nm ($\epsilon$, 8800); $\lambda_{max}^{H_2O}$ 269 nm ($\epsilon$, 8400); $\lambda_{max}^{pH\ 9.18}$ 269 nm ($\epsilon$, 8500).

EXAMPLE 5a 1-(5-Fluoro-1H-2-oxo-pyrimidin-4-yl)-$\beta$-D-glucopyranouronic acid

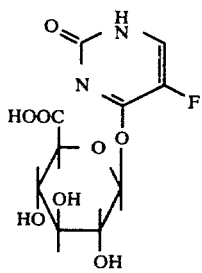

In 20 ml of anhydrous methanol was dissolved 362.6 mg of 1-(2-benzyloxy-5-fluoro-pyrimidin-4-yl)-$\beta$-D-glucopyranouronic acid. After replacing the atmosphere in the reaction vessel for reduction with nitrogen gas, 72.5 mg of 10%-palladium on carbon was added thereto and the resulting mixture was stirred at room temperature while introducing hydrogen gas thereinto. After completion of the reaction, the catalyst was removed from the reaction mixture by filtration and the solvent was removed by distillation under reduced pressure to give a crystalline powder, which was then suspended in a small amount of ethanol, recovered by filtration and washed to obtain 254 mg of the desired compound as a white powder.

Elementary analysis: for $C_{10}H_{11}O_8N_2F$ Calcd. C, 39.22; H, 3.62; N, 9.15; F, 6.20 Found C, 38.95; H, 3.51; N, 9.01; F, 6.31

Ultraviolet absorption spectrum $\lambda_{max}^{H_2O}$ 288 nm

EXAMPLE 6a 1-(5-Fluoro-1H-2-oxo-pyrimidin-4-yl)-2,3,4-tri-O-acetyl-$\beta$-D-glucopyranouronic acid methyl ester

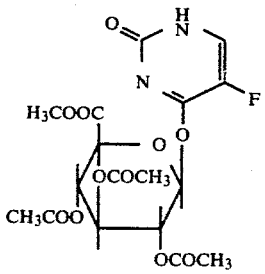

In 120 ml of anhydrous methanol was dissolved 1.2 g of 1-(2-benzyloxy-5-fluoro-5-pyrimidinyloxy)-2,3,4-tri-O-acetyl-$\beta$-D-glucopyranouronic acid methyl ester obtained in Example 1. After replacing the atmosphere in the reaction vessel for reduction with nitrogen gas, 240 mg of 10%-palladium on carbon was added to the solution, the atmosphere was replaced again with nitrogen gas and the resulting mixture was stirred for 15 minutes while introducing hydrogen gas under ordinary pressure. After completion of the reaction, insoluble substances which had formed were removed from the reaction mixture and the solvent was removed by distillation under reduced pressure. To the so-obtained residue was added ethanol to obtain crystals which had precipitated. White crystals, 891 mg of the desired compound melting at 115°–117° C., were then recovered by filtration. Further, 106 mg of secondary crystals were obtained from the mother liquor.

Elementary analysis: for $C_{17}H_{19}O_{11}N_2F \cdot H_2O$ Calcd. C, 43.97; H, 4.56; N, 6.03; F, 4.10 Found C, 44.70; H, 4.55; N, 5.89; F, 4.26

Ultraviolet absorption spectrum: $\lambda_{max}^{H_2O}$ 288 nm ($\epsilon$, 4800)

EXAMPLE 7a 1-(5-Fluoro-1H-2-oxo-pyrimidin-4-yl)-$\beta$-D-glucopyranouronic acid amide

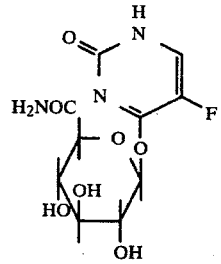

In 20 ml of anhydrous methanol was dissolved 200 mg of 1-(5-fluoro-1H-2-oxo-pyrimidin-4-yl)-2,3,4-tri-P-acetyl-$\beta$-D-glucopyranouronic acid methyl ester. The resulting solution was saturated with ammonia gas, while cooled with ice, and was allowed to stand, after plugging the vessel closely, in a refrigerator overnight. After completion of the reaction, the solvent was removed from the resulting reaction mixture by distillation under reduced pressure. Methanol was added to the crystalline residue which was obtained, and the resulting mixture was filtered. 111 mg of the desired compound as white crystals melting at 146°–150° C. (decomp.) were obtained.

Elementary analysis: for $C_{10}H_{12}O_7N_3F$ Calcd. C, 39.35; H, 3.96; N, 13.77; F, 6.22 Found C, 39.10; H, 3.81; N, 13.65; F, 6.12

Ultraviolet absorption spectrum: $\lambda_{max}^{H_2O}$ 286 nm ($\epsilon$, 9200)

EXAMPLE 8a 1-(2-Benzyloxy-5-fluoropyrimidin-4-yl)-2,3,4-tri-O-acetyl-β-D-glucopyranouronic acid isopropyl ester

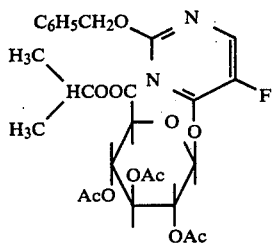

In 150 ml of dry xylene was suspended 3.27 g (10 mmol) of 2-benzyl-5-fluorouracil silver salt. In order to remove water, around 40 ml of the solvent was removed by distillation under ordinary pressure and the remaining suspension was allowed to cool. To the remaining suspension was added 4.25 g of 1-bromo-1-deoxy-2,3,5-tri-O-acetyl-α-D-glucopyranouronic acid isopropyl ester and the resulting mixture was refluxed under heating for 5 minutes. After completion of the reaction and allowing the heated mixture to cool, insoluble substances which had precipitated were filtered out and the solvent was removed by distillation under reduced pressure. The residue so obtained was dissolved in 100 ml of chloroform and the chloroform layer was washed successively with each of 50 ml of 5% aqueous sodium hydrogen carbonate and 20% aqueous sodium chloride. After each aqueous layer was extracted again with 50 ml of chloroform, all of the chloroform layers were combined and dried. The solvent was removed by distillation to obtain a colorless caramel-like residue. Ethanol was added to the residue to dissolve it and the resulting solution was allowed to stand in a refrigerator overnight. Crystals which precipitated were collected by filtration; 4.97 g of the desired compound as white crystals melting at 138°–139° C. were obtained.

Elementary analysis: for $C_{26}H_{29}O_{11}N_2F$ Calcd. C, 55.32; H, 5.18; N, 5.00; F, 3.37 Found C, 55.08; H, 5.21; N, 4.93; F, 3.12

Ultraviolet absorption spectrum: $\lambda_{max}^{0.1\ N\text{-}HCl\ in\ 50\%\ MeOH}$ nm (ε), 270 (10500); $\lambda_{max}^{50\%\ MeOH}$ nm (ε), 270 (10300); $\lambda_{max}^{0.1\ N\text{-}NaOH\ in\ 50\%\ MeOH}$ nm (ε), 270 (10800).

EXAMPLE 9a 1-(2-Benzyloxy-5-fluoropyrimidin-4-yl)-β-D-glucopyranouronic acid isopropyl ester

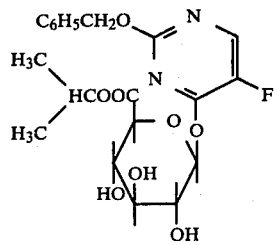

In a three-necked flash was placed 100 ml of anhydrous methanol, 0.366 g of metallic sodium was added thereto and the resulting mixture was cooled to −30° C. while shutting out moisture. Then, to the thus obtained methanol solution of sodium methoxide was added 4.50 g of 1-(2-benzyloxy-5-fluoropyrimidin-4-yl)-2,3,4-tri-O-acetyl-β-D-glucopyranouronic acid isopropyl ester and the mixture which was formed was stirred for 6 hours. After completion of the reaction, the reaction mixture was neutralized by adding acetic acid thereto and concentrated to dryness. The resulting residue was dissolved in 100 ml of ethyl acetate and the ethyl acetate layer was washed twice with 2.5% aqueous sodium hydrogen carbonate and saturated aqueous sodium chloride, respectively. After drying over anhydrous magnesium sulfate, the solvent was removed by distillation under reduced pressure and the resulting residue was crystallized from methanol to give the desired compound melting at 68°–69° C.

Elementary analysis: for $C_{20}H_{23}O_8N_2F.1/3\ H_2O$ Calcd. C, 54.05; H, 5.37; N, 6.30; F, 4.28 Found C, 54.06; H, 5.45; N, 6.24; F, 4.04

Ultraviolet absorption spectrum: $\lambda_{max}^{MeOH}$ nm (ε), 270 (7300)

EXAMPLE 10a 1-(5-Fluoro-1H-2-oxopyrimidin-4-yl)-β-D-glucopyranouronic acid isopropyl ester

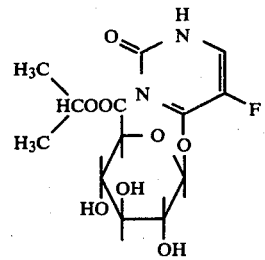

In 40 ml of anhydrous methanol was dissolved 0.46 g of 1-(2-benzyloxy-5-fluoropyrimidin-4-yl)-β-D-glucopyranouronic acid isopropyl ester. After replacing the atmosphere in the reaction vessel for reduction with nitrogen gas, 52.5 g of 10%-palladium on carbon was added to the solution and hydrogen gas was introduced thereto under ordinary pressure for reaction. After 23 ml of hydrogen gas was absorbed, the catalyst was removed by filtration from the reaction mixture and the solvent was removed by distillation under reduced pressure.

After addition of anhydrous methanol, crystals which precipitated were collected by filtration. The desired product melted at 151°–152° C.

Elementary analysis: for $C_{13}H_{17}O_8N_2F.6/5\ H_2O$ Calcd. C, 42.21; H, 5.29; N, 7.57; F, 5.14 Found C, 42.25; H, 5.08; N, 7.63; F, 4.71

Ultraviolet absorption spectrum: $\lambda_{max}$pH 6.86 phosphate buffer nm (ε) 288 (5200)

Compounds a–h shown in the following Table were obtained according to the same procedure as mentioned above, except that 1-bromo-1-deoxy-2,3,5-tri-O-acetyl-α-D-glucopyranouronic acid isopropyl ester, which was used in Example 8a for condensation reaction, was replaced with a corresponding halogenosaccharide:

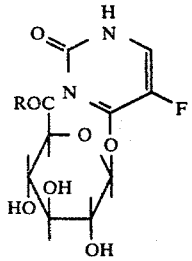

mixture by distillation under reduced pressure. After anhydrous ethanol was added to the resulting residue, crystals which had precipitated were recovered by filtration; 538 mg of the desired compound having a melting point of 159°–160° C. were so recovered. From the mother liquor 114 mg of the desired compound was recovered.

Elementary analysis: for $C_{18}H_{20}O_7N_3F$ Calcd. C, 52.81; H, 4.92; N, 10.26; F, 4.64 Found C, 52.58; H, 5.11; N, 10.24; F, 4.55

Ultraviolet absorption spectrum: $\lambda_{max}^{0.1\ N\text{-}HCl}$ nm($\epsilon$), 270 (7100); $\lambda_{max}^{MeOH}$ nm ($\epsilon$), 270 (7400); $\lambda_{max}^{0.1\ N\text{-}NaOH}$ nm($\epsilon$), 270 (7800).

| Compound | R | Melting point (°C.) | UV $\lambda_{max}^{pH6.86\ phosphate\ buffer}$ nm($\epsilon$) | Molecular formula |
|---|---|---|---|---|
| a | —CH$_2$CH$_3$ | 128 ~ 130 | 288 (4900) | C$_{12}$H$_{15}$O$_8$N$_2$F ½ H$_2$O |
| b | —(CH$_2$)$_2$CH$_3$ | 134 ~ 135 | 288 (5100) | C$_{13}$H$_{17}$O$_8$N$_2$F 6/5 . H$_2$O |
| c | —(CH$_2$)$_3$CH$_3$ | 140 ~ 141 | 288 (5100) | C$_{14}$H$_{19}$O$_8$N$_2$F 6/5 . H$_2$O |
| d | —CH$_2$CH(CH$_3$)CH$_3$ | 136 ~ 137 | 288 (4800) | C$_{14}$H$_{19}$O$_8$N$_2$F H$_2$O |
| e | —(CH$_2$)$_4$CH$_3$ | 126 ~ 127 | 288 (4900) | C$_{15}$H$_{21}$O$_8$N$_2$F ½ H$_2$O |
| f | —(CH$_2$)$_2$CH(CH$_3$)CH$_3$ | 126 ~ 129 | 288 (5100) | C$_{15}$H$_{21}$O$_8$N$_2$F 3/2 H$_2$O |
| g | —(CH$_2$)$_5$CH$_3$ | 127 ~ 129 | 288 (5000) | C$_{16}$H$_{23}$O$_8$N$_2$F H$_2$O |
| h | —C$_6$H$_{11}$ | 145 ~ 148 | 288 (5200) | C$_{16}$H$_{21}$O$_8$N$_2$F 3/2 H$_2$O |

| Compound | Calcd. (%) | | | | Found (%) | | | |
|---|---|---|---|---|---|---|---|---|
| | C | H | N | F | C | H | N | F |
| a | 41.62 | 4.75 | 8.06 | 5.49 | 41.32 | 5.01 | 7.83 | 5.73 |
| b | 42.21 | 5.29 | 7.57 | 5.14 | 42.14 | 5.00 | 7.30 | 5.59 |
| c | 43.79 | 5.62 | 7.30 | 4.95 | 43.62 | 5.42 | 7.08 | 5.23 |
| d | 44.21 | 5.57 | 7.37 | 5.00 | 44.09 | 5.47 | 7.25 | 5.15 |
| e | 46.75 | 5.75 | 7.27 | 4.73 | 46.23 | 5.34 | 7.22 | 4.63 |
| f | 44.67 | 6.00 | 6.95 | 4.71 | 44.90 | 5.72 | 7.10 | 4.60 |
| g | 47.06 | 6.17 | 6.86 | 4.65 | 47.04 | 5.54 | 6.99 | 4.50 |
| h | 46.27 | 5.82 | 6.74 | 4.57 | 46.22 | 5.59 | 6.89 | 4.62 |

EXAMPLE 11a 1-(2-Benzyloxy-5-fluoropyrimidin-4-yl)-$\beta$-D-glucopyranouronic acid methylamide

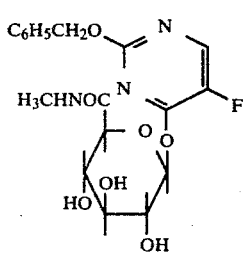

In 70 ml of anhydrous methanol was dissolved 1.34 g of 1-(2-benzyloxy-5-fluoropyrimidin-4-71)-2,3,4-tri-O-acetyl-$\beta$-D-glucopyranouronic acid methyl ester. Into the resulting solution was introduced dry monomethylamine over 10–15 minutes while shutting out moisture. Then the vessel was closed with a plug and the solution was stirred at 0° C. for 3 hours. After completion of the reaction, the solvent was removed from the reaction

EXAMPLE 12a 1-(5-Fluoro-1H-2-oxopyrimidin-4-yl)-$\beta$-D-glucopyranouronic acid methylamide

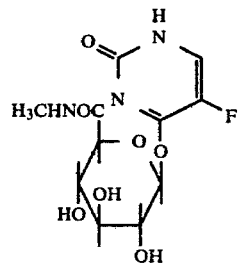

In 5 ml of anhydrous methanol was dissolved 40.9 mg of 1-(2-benzyloxy-5-fluoropyrimidin-4-yl)-$\beta$-D-glucopyranouronic acid methylamide. After the atmosphere in the reaction vessel was replaced with nitrogen gas, 8.2 mg of 10%-palladium on carbon was added to the solution which had formed and hydrogen gas was introduced thereinto over around 5 minutes. After completion of the reaction, the catalyst was removed from the resulting reaction mixture by filtration and the filtrate was evaporated to dryness under reduced pressure. The the resulting crystalline residue was added anhydrous ethanol. Crystals were recovered by filtration; 13.8 mg of the desired compound having a melting point of 130°–140° C. (decomp.) were so recovered.

Elementary analysis: for $C_{11}H_{14}O_7N_3F \cdot CH_3OH$ Calcd. C, 41.03; H, 5.16; N, 11.96; F, 5.41 Found C, 39.87; H, 5.13; N, 11.85; F, 5.48

Ultraviolet absorption spectrum: $\lambda_{max}^{H2O}$ nm ($\epsilon$), 387 (4600).

Referential Example A

2-Benzyl-5-fluorouracil silver salt

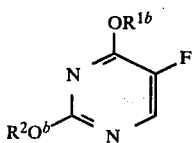

In 90 ml of water was suspended 5.387 g (24.5 mmol) of 2-benzyl-5-fluorouracil, which was then dissolved completely by adding 29.4 ml of 1 N aqueous solution of sodium hydroxide. To the resulting solution was added dropwise with stirring a solution of 4.17 g (24.5 mmol) of silver nitrate in 30 ml of water and the mixture which formed was stirred further for 15 minutes at room temperature. After completion of the reaction, precipitates which has formed were recovered by filtration, washed with water and dried. Further drying for 7 hours at 60° C. in the presence of phosphorus pentoxide gave 7.9 g of the desired silver salt.

Elementary analysis: for $C_{11}H_8O_2N_2FAg \cdot \frac{1}{2}H_2O$ Calcd. C, 39.31; H, 2.70; N, 8.34; F, 5.65 Found C, 39.14; H, 2.48; N, 8.41; F, 5.78

COMPOUNDS (Ib)

Included also herein are 5-fluorouracil compounds of formula (Ib):

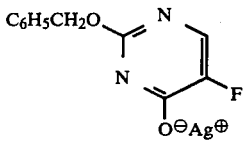

wherein $R^{1n}$ and $R^{2b}$, which are the same, each represents a $\beta$-D-glucopyranosyl, $\beta$-D-galactopyranosyl, $\beta$-D-ribopyranosyl or $\beta$-D-xylopyranosyl group, or one of $R^{1b}$ and $R^{2b}$ represents a $\beta$-D-glucopyranosyl, $\beta$-D-galactopyranosyl, $\beta$-D-ribopyranosyl or $\beta$-D-xylopyranosyl group, and the other of $R^{1b}$ and $R^{2b}$ represents a hydrogen atom.

Further, $R^{1b}$ and $R^{2b}$ in formula (Ib) are each represented by the same formula (IIb):

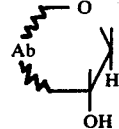

wherein Ab represents a group of the following formulae:

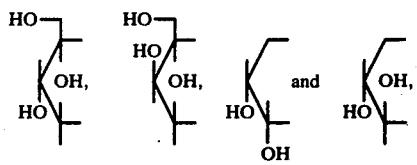

or one of $R^{1b}$ and $R^{2b}$ represents a group represented by formula (IIb) and the other represents a hydrogen atom.

Typical compounds of formula (Ib) are as follows:

(1b) $O^2$-($\beta$-D-glucopyranosyl)-5-fluorouracil (2b) $O^2$-($\beta$-D-galactopyranosyl)-5-fluorouracil (3b) $O^2$-($\beta$-D-ribopyranosyl)-5-fluorouracil (4b) $O^2$-($\beta$-D-xylopyranosyl)-5-fluorouracil (5b) $O^4$-($\beta$-D-glucopyranosyl)-5-fluorouracil (6b) $O^4$-($\beta$-D-galactopyranosyl)-5-fluorouracil (7b) $O^4$-($\beta$-D-ribopyranosyl)-5-fluorouracil (8b) $O^4$-($\beta$-D-xylopyranosyl)-5-fluorouracil (9b) $O^2$, $O^4$-bis($\beta$-D-glucopyranosyl)-5-fluorouracil (10b) $O^2$, $O^4$-bis($\beta$-D-galactopyranosyl)-5-fluorouracil (11b) $O^2$, $O^4$-bis($\beta$-D-ribopyranosyl)-5-fluorouracil (12b) $O^2$, $O^4$-bis($\beta$-D-xylopyranosyl)-5-fluorouracil Compounds of formula (Ib) according to this invention can be prepared by the following schemes:

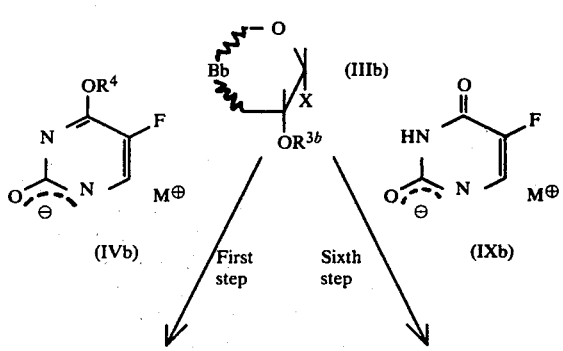

-continued

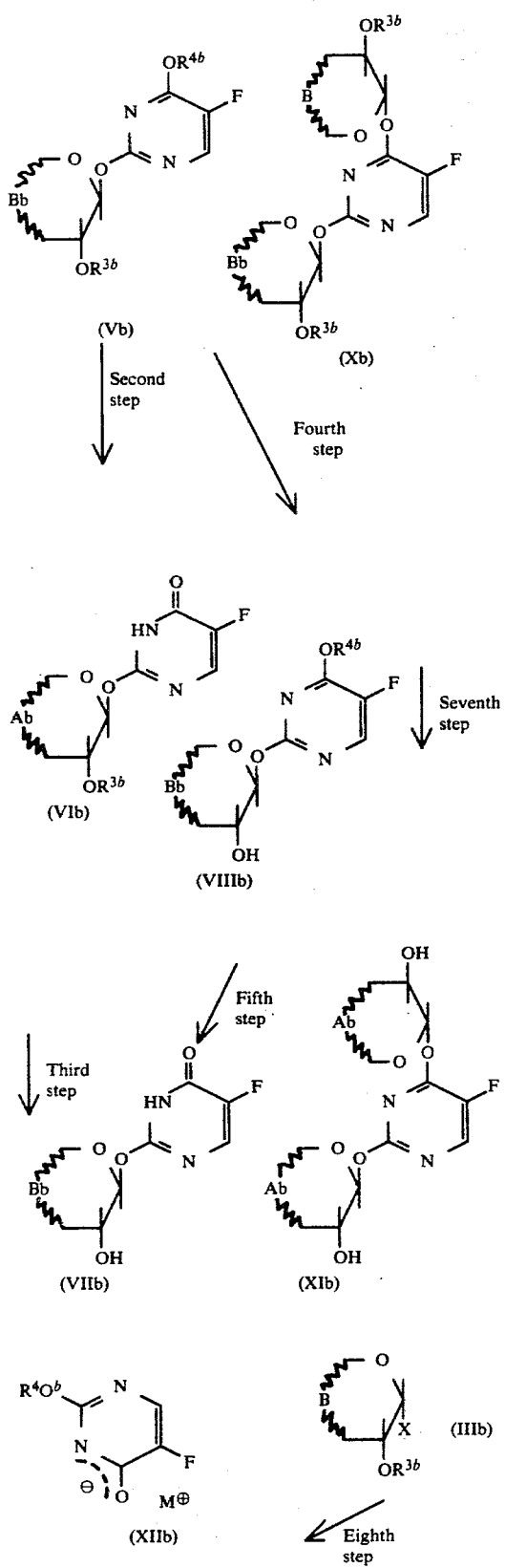

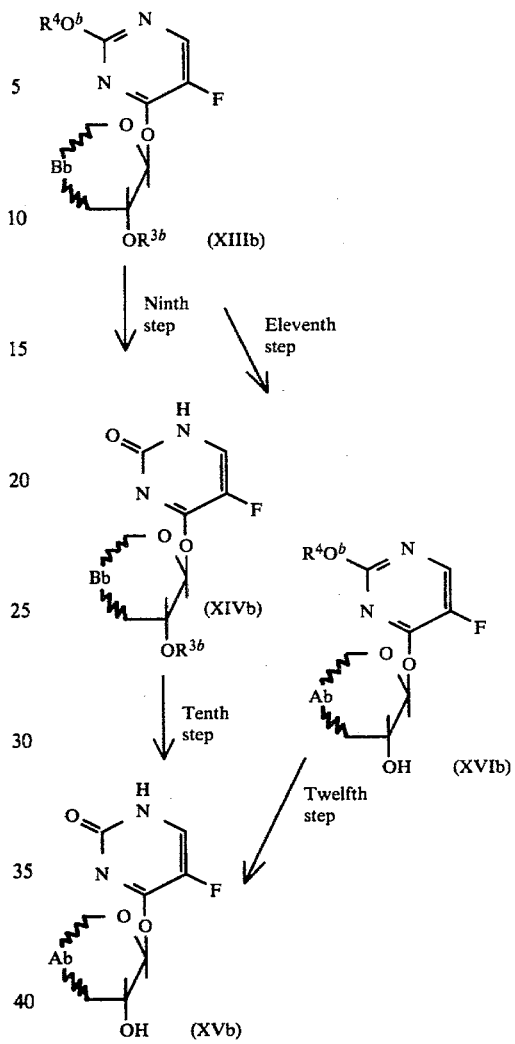

wherein Ab has the same meaning as above, $R^{3b}$ represents an acyl group used as a protecting group for the hydroxyl group in a sugar such as an aliphatic acyl radical, e.g., formyl, acetyl, n-propionyl, n-butryl or isobutryl or an aromatic acyl group, e.g., benzoyl, p-nitrobenzoyl, p-methoxybenzoyl or p-methoxybenzoyl; $R^{4b}$ represents a protecting group for the hydroxyl group in the pyrimidine nucleus such as benzyl group which may be substituted with a nitro or a halogen atom such as chlorine and bromine and said protecting group being removed by reduction; Bb represents a group of formulae:

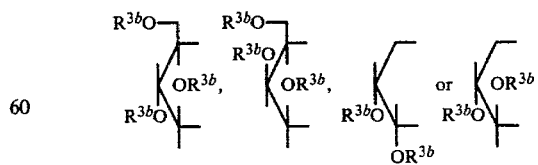

wherein $R^{3b}$ has the same meaning as above; $M^{\oplus}$ represents a metal ion used for the preparation of O-glucosides by condensation of a sugar with a heterocyclic base salt of a monovalent silver, monovalent mercury, divalent mercury such as —HgCl or —HgBr$_2$ and alkali metal such as sodium and potassium; and X represents a halogen atom such as chlorine and bromine.

The process for the preparation is carried out by an optional combination of condensation of a 5-fluorouracil metal salt and a halogeno sugar and the removal reaction of a protecting group for the pyrimidine nucleus and hydroxyl group of sugar and is explained in detail by the above reaction schemes.

The first step is a process for preparing O-glucosides of formula (Vb), which is a condensation step of a 5-fluorouracil metal salt of formula (IVb) with a halogenopyranose derivative of formula (IIIb). The condensation is effected by contacting a compound of formula (IVb) with a compound of formula (IIIb) in a solvent. The solvents used are not limitative and are preferably aromatic hydrocarbons such as toluene and xylene, aliphatic dialkylamides such as dimethylformamide and dimethylacetamide, dialkylsulfoxides such as dimethylsulfoxide, phosphoric acid amide such as hexamethylphosphoroamide, nitroalkanes such as nitromethane and nitriles such as acetonitrile. The reaction temperature is not limitative and is usually at a range of 0° to 150° C. The reaction is generally preferable at a range of 100° to 150° C. in a non-polar solvent and near room temperature in a polar solvent. The reaction time varies with mainly the reaction temperature and the solvent used and is from about 5 minutes to 30 hours.

This reaction is also carried out by adding mercuric cyanide to a compound of formula (XVIIb):

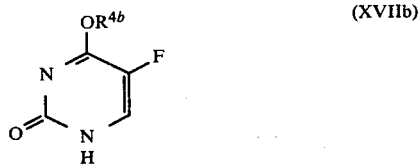

wherein $R^{4b}$ has the same meaning as above, in a solvent (instead of the metallic salt of formula (IVb)), and adding a halogenopyranose derivative of formula (IIIb) to the resulting mixture with heating.

After completion of this reaction, the desired compound (Vb) of this step is recovered from the reaction mixture by a conventional method. For example, after the reaction mixture is filtered from the insoluble material which is formed, the filtrate is evaporated under reduced pressure and the thus resulting residue is extracted with an organic solvent such as ethyl acetate. The filtrate is washed with water, dried and evaporated to give a residue, to which an organic solvent such as ethanol is added. The mixture is allowed to stand to give crystals which can be filtered.

The second step is a process for preparing a compound of formula (VIb), which is a step of removing a protecting group for the hydroxyl group of the pyrimidine nucleus in the compound of formula (Vb).

This reaction is carried out by contacting a compound of formula (Vb) with a reducing agent in a solvent. The reducing agents used are expecially non-limitative reducing ones such as are used for removing protecting groups such as benzyl group, and preferably catalytic reducing agents such as hydrogen and palladium-carbon. The solvents used are non-limitatively any solvents which are inert for the reaction and can dissolve the compound (Vb); preferably they are alcohols such as methanol and ethanol and ethers such as tetrahydrofuran and dioxane. The reaction temperature is especially non-limitative and usually perferably near room temperature. The reaction time is continued until one mole of hydrogen is absorbed.

After completion of the reaction, the compound (VIb) is recovered from the reaction mixture by a conventional manner. For example, the reaction mixture is filtered from undissolved matter which is formed and evaporated under reduced pressure. An organic solvent such as ethanol is added to the residue and allowed to stand to give crystals which can filtered.

The third step is a process for preparing $O^2$-($\beta$-D-pyranosyl)-5-fluorouracil of formula (VIIb). This is a step of removing an acyl protecting group of the hydroxyl group of the sugar part in a compound of formula (VIb). This reaction is carried out by contacting a compound of formula (VIb) with a base such as ammonia or an alkali metal alkoxide in a solvent. The bases used are preferably ammonia, sodium methoxide, sodium ethoxide or potassium t-butoxide. The solvents used are any solvents which are inert for the reaction and preferably alcohols such as methanol, ethanol and t-buthanol, and a combined solvent of such an alcohol and an organic solvent such as an ether illustrated by hydrofuran and dioxane, or a halogenohydrocarbon such as methylene chloride and chloroform. The reaction is preferably carried out under anhydrous conditions. The reaction temperature is non-limitative and at a range of from $-30°$ to 50° C., and especially preferably at a range of from 0° C. to about room temperature. The reaction time varies mainly depending on the reaction temperature but is usually at a range of from 2 to 20 hours.

After completion of the reaction, the compound (VIIb) is recovered from the reaction mixture by a conventional manner. For example, the reaction mixture is evaporated under reduced pressure and the resulting residue is dissolved in a small amount of anhydrous methanol and the addition thereto of chloroform results in crystals which can be filtered off.

The fourth step is a process for preparing a compound of formula (VIIIb). This is a step of removing an acyl protecting group for the hydroxyl group of the sugar part in a compound of formula (Vb). The reaction conditions and after-treatment are the same as in the third step.

The fifth step is another process for preparing $O^2$-($\beta$-D-pyranosyl)-5-fluorouracil of formula (VIIb). This is a step of removing a protecting group for the hydroxyl group of the pyrimidine nucleus in a compound of formula (VIIIb) by reduction. The reaction conditions and after-treatment are the same as in the second step.

The sixth step is a process for preparing an O-glucoside of formula (Xb). This is a condensation step between a 5-fluorouracil metal salt of formula (IXb) and a halogenopyranose derivative of formula (IIIb). The reaction conditions in this step are the same as in the first step described above and can also be carried out by adding mercuric cyanide to 5-fluorouracil in a solvent (instead of the metal salt of formula (IXb)), and further adding a halogenopyranose compound of formula (IIIb) to the resulting mixture with heating. After completion of the reaction, the desired compound (Xb) can be recovered from the reaction mixture by a conventional manner using the same after-treatment as in the first step.

The seventh reaction is a process for preparing an $O^2$, $O^4$-bis($\beta$-D-pyranosyl)-5-fluorouracil of formula (XIb). This is a step of removing an acyl protecting group for the hydroxyl group of the sugar part in a compound of formula (Xb). The reaction conditions and after-treatment of this reaction are the same as in the third step described above.

The eighth step is a process for preparing an O-glucoside compound of formula (XIIIb). This is a condensation step between a 5-fluorouracil of formula (XIIb) and a halogenopyranose of formula (IIIb). The reaction conditions of this step are the same as in the first step described above. This step can also be carried out by adding mercuric cyanide to a compound of formula (XVIIIb):

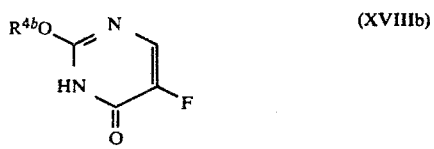

wherein $R^{4b}$ is defined as above, in a solvent (instead of a metal salt of formula (XIIb)) and adding further a halogenopyranose compound of formula (IIIb) to the resulting mixture. After completion of the reaction, the desired compound (XIIIb) of this step is recovered from the reaction mixture by a conventional manner using the same after-treatment as in the first step described above.

The ninth step is a process for preparing a compound of formula (XIVb). This is a step of removing a protecting group for the hydroxyl group of the pyrimidine nucleus in a compound of formula (XIIIb). The reaction conditions and after-treatment of this step are the same as in the second step described above.

The tenth step is a process for preparing an $O^4$-($\beta$-D-pyranosyl)-5-fluorouracil of formula (XVb). This is a step of removing an acyl protecting group for the hydroxyl group of the sugar part in a compound of formula (XIVb). The reaction conditions and after-treatment of this step are the same as in the third step.

The eleventh step is a process for preparing a compound of formula (XVIb). This is a step of removing an acyl protecting group for the hydroxyl group of the sugar part in a compound of formula (XIIIb). The reaction conditions and after-treatment of this step are the same as in the third step.

The twelfth step is another process for preparing an $O^4$-($\beta$-D-pyranosyl)-5-fluorouracil of formula (XVb). This is a step of removing a protecting group for the hydroxyl group in the pyrimidine nucleus in a compound of formula (XVIb). The reaction conditions and after-treatment of this step are the same as in the second step.

The compounds obtained by each of the steps described above can be purified, if necessary, by a conventional method, for example, recrystallization, column chromatography or reprecipitation.

Compounds of formula (Ib) are illustrated below.

EXAMPLE 1b $O^2$-($\beta$-D-Tetra-O-acetylglucopyranosyl)-$O^4$-benzyl-5-fluorouracil

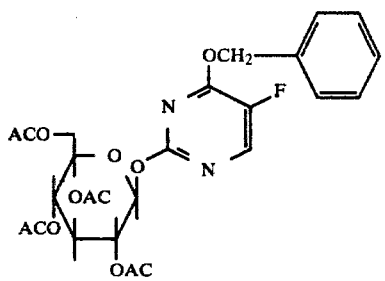

In 100 ml of anhydrous xylene, which was dehydrated with calcium hydride and distilled, was suspended 1.95 g (6.1 mmole) of $O^4$-benzyl-5-fluorouracil silver salt and the resulting mixture was refluxed to distill about 10 ml to remove water under azeotropic distillation. After cooling, 2.51 g (6.1 mmole) of 2,3,4,6-tetraacetyl-$\alpha$-D-glucopyranosyl bromide was added to the mixture and the mixture was refluxed for 5 minutes. After completion of the reaction, the crystallized insoluble material which has formed was filtered off and the filtrate was distilled under reduced pressure to give a caramel-like residue. This residue was dissolved in 30 ml of ethyl acetate and washed once with 5% sodium hydrogen carbonate aqueous solution and twice with 20 ml of water. The resulting aqueous layer was extracted with 15 ml of ethyl acetate. The combined organic layer was dried over anhydrous magnesium sulfate and distilled under reduced pressure to give a caramel-like substance, which was dissolved in 15 ml of ethanol. The ethanol solution was allowed to stand whereupon white crystals formed. These crystals were recrystallized from a mixture of 15 ml of ethanol and 4 ml of benzene to give 1.986 g of the desired compound having a melting point of 140° to 141° C.

The mother liquor was further concentrated and dried, and the resulting residue was subjected to column chromatography using silica gel and eluted with chloroform to give several portions, which were purified to give 274 mg of the desired crystals.

Elementary analysis for $C_{25}H_{27}O_{11}N_2F$ Calculated: C, 54.55; H, 4.94; N, 5.09; F, 3.45 Found: C, 54.34; H, 5.08; N, 5.04; F, 3.30

Ultraviolet absorprtion spectrum $\lambda_{methanol}$ $max^{0.1}$ $N\text{-}HCl$ in nm ($\epsilon$): 264 (5200); $\lambda_{max}{}^{0.1}$ $N\text{-}NaOH$ nm ($\epsilon$): 264 (5100); $\lambda_{max}{}^{0.1}$ $N\text{-}NaOH$ $in$ $MeOH$ nm ($\epsilon$): 265 (5500)

EXAMPLE 2b $O^2$-($\beta$-D-Tetra-O-acetylglucopyranosyl)-5-fluorouracil

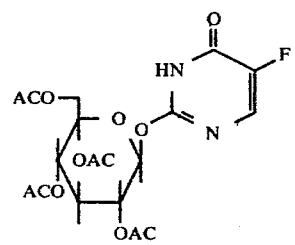

Into 30 ml of anhydrous methanol was dissolved 550 mg (1 mmole) of O²-(β-D-tetra-O-acetylglucopyranosyl)-O⁴-benzyl-5-fluorouracil and the reduction vessel was replaced with dried nitrogen gas and 100 mg of 10% Pd on carbon was added. The resulting mixture was reduced with shaking at room temperature and under normal pressure until 24 ml of hydrogen was absorbed. After completion of the reaction, the vessel was again replaced with nitrogen gas and the catalyst was filtered out. The filtrate was concentrated under reduced pressure and dried to give a crystalline residue, which was dissolved in 45 ml of anhydrous ethanol while heating. The ethanol solution was allowed to stand in a refrigerator overnight to give crystals, which were filtered; 373 mg of white crystals were recovered. These crystals melted at 140°–142° C. and decomposed with color at 197° to 212° C.

Elementary analysis for $C_{18}H_{21}O_{11}N_2F$ Calculated: C, 46.96; H, 4.60; N, 6.09; F, 4.13 Found: C, 47.23; H, 4.90; N, 5.73; F, 3.95

Ultraviolet absorption spectrum $\lambda_{max}^{MeOH}$ nm (ε): 266 (6200)

EXAMPLE 3b

O²-(β-D-Glucopyranosyl)-5-fluorouracil

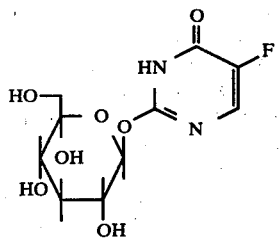

In 25 ml of anhydrous methanol was dissolved 460 mg (1 mmole) of O²-(β-D-tetra-O-actylglucopyranosyl)-5-fluorouracil and the resulting solution was saturated with dried ammonia gas and allowed to stand for 4 hours and then kept in a refrigerator overnight. After completion of the reaction, the solvent was distilled under reduced pressure. The resulting residue was dissolved in a small amount of methanol. The addition of 10 ml of chloroform gave a crystalline powdered material, which was filtered to give 307 mg of the desired compound. This material melted at 103° to 109° C. in part and decomposed with bubbles at 116° to 119° C.

Elementary analysis for $C_{10}H_{13}O_7N_2F \cdot CH_3OH \cdot NH_3 \cdot H_2O$ Calculated: C, 36.77; H, 6.17; N, 11.70; F, 5.29 Found: C, 36.06; H, 5.73; N, 12.07; F, 5.38

Ultraviolet absorption spectrum $\lambda_{max}$ 0.02 M-Phosphate buffer (pH 6.86) nm (ε): 268 (7000)

EXAMPLE 4b

O²,O⁴-Bis(β-D-tetra-O-acetylglucopyranosyl)-5-fluorouracil

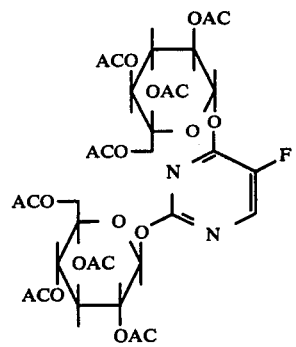

In 50 ml of well-dried acetonitrile was dissolved 4.11 g (10 mmole) of 2,3,4,6-tetraacetyl-α-D-glucopyranosyl bromide, and 2.17 g (10 mmole) of 5-fluorouracil silver salt was added thereto. The resulting mixture was stirred for 30 hours at room temperature. After completion of the reaction, a crystallized undissolved material was filtered out. The filtrate was concentrated and dried under reduced pressure to give 3.93 g of a colorless caramel-like substance. This substance was subjected to column chromatography using silica gel and eluted with a developing solvent of chloroform containing 1% methanol. The fractions obtained were crystallized from ethanol to give 1.342 g of white crystals with a melting point of from 183° to 190° C., as the desired compound.

Elementary analysis for $C_{32}H_{39}O_{20}N_2F$ Calculated: C, 48.61; H, 4.97; N, 3.54; F, 2.40 Found: C, 48.66; H, 5.08; N, 3.74; F, 2.24

Ultraviolet absorption spectrum $\lambda_{max}^{H+\ in\ MeOH}$ nm: 265; $\lambda_{max}^{MeOH}$ nm (ε): 265 (6800); $\lambda_{max}^{OH-\ in\ MeOH}$ nm: 267.

EXAMPLE 5b

O², O⁴-Bis(β-D-glucopyranosyl)-5-fluorouracil

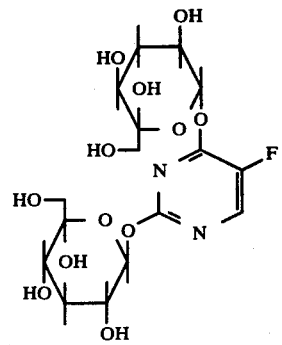

In 50 ml of anhydrous methanol was suspended 790 mg (1 mmole) O²,O⁴-bis(β-D-tetra-O-acetylglucopyranosyl)-5-fluorouracil. The resulting mixture was saturated with dry ammonia gas while cooling with ice-water and stirred at 5° C. overnight under tight sealing. After completion of the reaction, the solvent was distilled under reduced pressure and redistilled twice after addition of anhydrous methanol. The resulting residue was dissolved in 5 ml of anhydrous methanol. The addition of 40 ml of chloroform caused a white precipitate, which was filtered, washed with chloroform and dried to give 320 mg of white powder as the desired product. This had a melting point of from 110° to 113° C. (decomp.).

Elementary analysis for $C_{16}H_{23}O_{12}N_2F \cdot CH_3OH \cdot 2H_2O$ Calculated: C, 39.08; H, 5.98; N, 5.36; F, 3.64 Found: C, 39.28; H, 5.64; N, 5.60; F, 3.57

Ultraviolet absorption spectrum $\lambda_{max}$ 0.02 N-Phosphate buffer (pH 6.86 nm ($\epsilon$): 266 (5800)

EXAMPLE 6b $O^4$-($\beta$-D-Tetra-O-acetylglucopyranosyl)-$O^2$-benzyl-5-fluorouracil

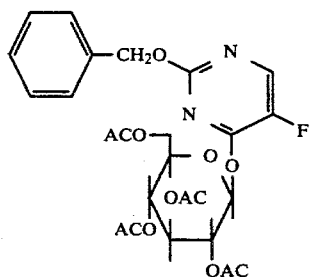

In 220 ml of dry xylene was suspended 4.91 g (15 mmole) of 2 benzyl-5-fluorouracil silver salt. The resulting mixture was refluxed and 20 ml of xylene was distilled off to remove water. 6.17 g (15 mmole) of 2,3,4,6-tetraacetyl-α-D-glucopyranosyl bromide was added thereto and the mixture which formed was refluxed for 5 minutes. After completion of the reaction, a crystallized gray-yellow insoluble material was filtered off and the solvent was concentrated and dried under reduced pressure. The resulting residue was dissolved in 100 ml of ethyl acetate and washed once with 70 ml of 5% sodium hydrogen carbonate and twice with 70 ml of water. The resulting water layer was extracted with 50 ml of ethyl acetate several times, and the combined organic layer was dried over anhydrous magnesium sulfate and distilled under reduced pressure to give a caramel-like substance, which was dissolved in ethanol. The addition of isopropanol caused crystals, which were filtered and dried to give 5.795 g of the desired compound as white crystals with a melting point of 95° to 96° C.

Elementary analysis for $C_{25}H_{27}O_{11}N_2F$ Calculated: C, 54.54; H, 4.94; N, 5.09; F, 3.26 Found: C, 54.33; H, 4.92; N, 4.70; F, 3.26

Ultraviolet absorption spectrum $\lambda_{max}^{0.1\ N\text{-}HCl\ in\ MeOH}$ nm ($\epsilon$): 270 (7200); $\lambda_{max}^{MeOH}$ nm ($\epsilon$): 270 (7100); $\lambda_{max}^{0.1\ N\text{-}NaOH\ in\ MeOH}$ nm ($\epsilon$): 270 (8300)

EXAMPLE 7b $O^4$-($\beta$-D-Tetra-O-acetylglucopyranosyl)-5-fluorouracil

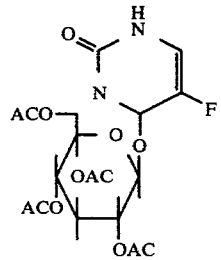

In 130 ml of distilled tetrahydrofuran was dissolved 5.795 g (10.5 mmole) of $O^4$-($\beta$-D-tetra-O-acetylglucopyranosyl)-$O^2$-benzyl-5-fluorouracil and the vessel for reduction was replaced with nitrogen gas and 526 mg of 10% palladium on carbon was added thereto. The resulting mixture was reduced while shaking at room temperature and normal pressure until 254 ml of hydrogen was absorbed. Then the vessel was again replaced with nitrogen gas and 52 mg of palladium-carbon was further added and 14 ml of hydrogen gas was caused to be absorbed. After completion of the reaction, the vessel was replaced with nitrogen gas and the catalyst was filtered out. The filtrate was concentrated and dried under reduced pressure to give a crystalline residue, to which methanol was added to give crystals. The crystals were filtered to give 4.318 g of the desired compound with a melting point of 154° to 155° C.

Elementary analysis for $C_{18}H_{21}O_{11}N_2F$ Calculated: C, 46.96; H, 4.60; N, 6.09; F, 4.13 Found: C, 46.87; H, 4.67; N, 5.93; F, 3.94

Ultraviolet absorption spectrum $\lambda_{max}^{MeOH}$ nm ($\epsilon$): 288 (4200)

EXAMPLE 8b $O^4$-($\beta$-D-Glucopyranosyl)-5-fluorouracil

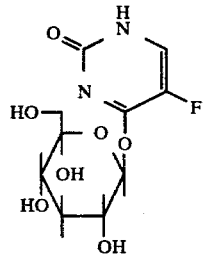

In 125 ml of anhydrous methanol was dissolved 2.3 g (5 mmol) of $O^4$-($\beta$-D-tetra-O-acetylglucopyranosyl)-5-fluorouracil. The resulting mixture was saturated with dry ammonia with ice-cooling, stirred for 6 hours and allowed to stand in a refrigerator overnight. After completion of the reaction, the solvent was distilled under reduced pressure and the distillation was repeated by addition of anhydrous ethanol. The thus obtained gelatinous substance was filtered and dried to give 1.40 g of the desired compound as a white powder with a melting point of 114° C. to 115° C.

Elementary analysis for $C_{10}H_{13}O_7N_2F \cdot \frac{1}{2}H_2O$ Calculated: C, 39.87; H, 4.68; N, 9.30; F, 6.31 Found: C, 39.36; H, 5.02; N, 9.31; F, 6.13

Ultraviolet absorption spectrum $\lambda_{max}$ 0.02 M-Phosphate buffer (pH 6.86) nm ($\epsilon$): 286 (4600)

EXAMPLE 9b $O^2$-Benzyl-$O^4$-($\epsilon$-D-glucopyranosyl)-5-fluorouracil

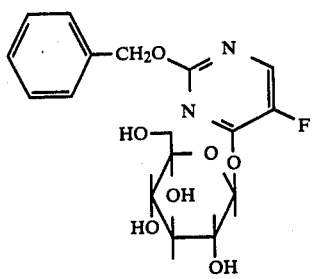

In 100 ml of anhydrous methanol was dissolved 550 mg of $O^4$-($\epsilon$-D-tetra-O-acetylglucopyranosyl)-$O^2$-benzyl-5-fluorouracil obtained by Example 6b and the resulting mixture was saturated with dry ammonia at room temperature and stirred for 2 hours after tight sealing. After completion of the reaction, the solvent was distilled under reduced pressure to give 410 mg of a caramel-like substance. This substance was subjected to thin layer chromatography using a fractional silica gel plate, eluted and purified with a developing solution of chloroform containing 10% methanol to give 310 mg of the desired compound as a caramel-like substance. This gave a single spot with a thin layer chromatography.

EXAMPLE 10b $O^4$-($\beta$-D-Glucopyranosyl)-5-fluorouracil

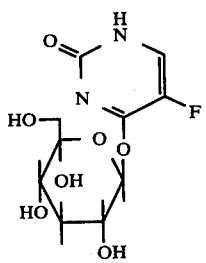

In 20 ml of anhydrous methanol was dissolved 310 mg of $O^2$-benzyl-$O^4$-($\beta$-D-glucopyranosyl)-5-fluorouracil and 50 mg of 10% palladium on carbon was added. The resulting mixture was stirred at room temperature and normal pressure while passing nitrogen gas therethrough. The catalyst was filtered after 5 minutes and the solvent was distilled under reduced pressure to give a caramel-like substance, which was dissolved in ethanol and allowed to stand to give crystals. The crystals were filtered to give a white powder of the desired compound, which was identical with the compound obtained by Preparative Example 8b.

COMPOUNDS (Ic)

The 5-fluorouracil compounds of this invention include those of formula (Ic)

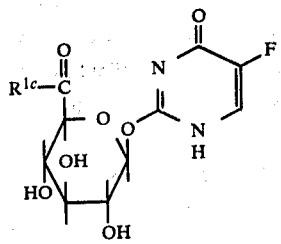

In the above formula, $R^{1c}$ represents a hydroxyl group, an alkoxy group, a cycloalkoxy group, an aralkyloxy group, an aryloxy group or a group

in which $R^{2c}$ and $R^{3c}$ may be the same or different and each represents a hydrogen atom, an alkyl group, a cycloalkyl group, an aralkyl group or an aryl group; or $R^{2c}$ and $R^{3c}$ may form, taken together with the adjacent nitrogen atom, a cyclic amino group.

In formula (Ic) mentioned above, $R^{1c}$ represents a hydroxyl group; a straight-chain or branched alkoxy group having from 1 to 8 carbon atoms, e.g., methoxy, ethoxy, n-propoxy, isopropoxy, n-butoxy, isobutoxy, n-pentyloxy, isopentyloxy, n-hexyloxy, sec-hexyloxy, n-heptyloxy, n-octyloxy, 2-ethylhexyloxy, etc.; a cycloalkoxy group having from 5 to 7 ring members, e.g., cyclopentyloxy, cyclohexyloxy, cycloheptyloxy, etc.; an aralkyloxy group, the aromatic ring of which may be unsubstituted or substituted with a lower alkyl group such as methyl, ethyl, n-propyl, isopropyl, n-butyl and isobutyl, a lower alkoxy group such as methoxy, ethoxy, n-propoxy, isopropoxy, n-butoxy and isobutoxy, or a halogen atom such as chlorine, bromine and fluorine, e.g., benzyloxy, phenethyl, etc.; an aryl group, the aromatic ring of which may be unsubstituted or substituted with a lower alkyl group such as methyl, ethyl, n-propyl, isopropyl, n-butyl and isobutyl, a lower alkoxy group such as methoxy, ethoxy, n-propoxy, isopropoxy, n-butoxy and isobutoxy, or a halogen atom such as chlorine, bromine and fluorine, e.g., phenyl, etc.; or a group

in which $R^{2c}$ and $R^{3c}$ may be the same or different and each represents a hydrogen atom; a straight-chain or branched alkyl group having from 1 to 5 carbon atoms, e.g., methyl, ethyl, n-propyl, isopropyl, n-butyl, isobutyl, n-pentyl, isopentyl, etc.; a cycloalkyl group having from 5 to 7 ring members, e.g., cyclopentyl, cyclohexyl, cycloheptyl, etc.; an aralkyl group, the aromatic ring of which may be unsubstituted or substituted with a lower alkyl group such as methyl, ethyl, n-propyl, isopropyl, n-butyl and isobutyl, a lower alkoxy group such as methoxy, ethoxy, n-propoxy, isopropoxy, n-butoxy and isobutoxy, or a halogen atom such as chlorine, bromine and fluorine, e.g., benzyl, phenethyl, etc.; an aryl group, the aromatic ring of which may be unsubstituted or substituted with a lower alkyl group such as methyl, ethyl, n-propyl, isopropyl, n-butyl and isobutyl, a lower alkoxy group such as methoxy, ethoxy, n-propoxy, isopropoxy, n-butoxy and isobutoxy, or a halogen atom such as chlorine, bromine and fluorine, e.g., phenyl etc.; or $R^{2c}$ and $R^{3c}$ may form, taken together with the adjacent nitrogen atom, a 5 to 6 membered-cyclic amino group, e.g., 1-pyrrolidinyl, piperidino, morpholino, etc.

Further, in formula (Ic) mentioned above, $R^{1c}$ preferably represents a hydroxyl group; a straight-chain or branched alkoxy group having from 1 to 8 carbon atoms; an amino group; a straight-chain or branched alkylamino or dialkylamino group having from 1 to 5 carbon atoms; a benzylamino group; and a cyclic amino group having 5 to 6 ring members.

As compounds of formula (Ic), above, the following are illustrative:

1c.  1-(5-Fluoro-1H-4-oxopyrimidin-2-yl)-β-D-glucopyranouronic acid
2c.  1-(5-Fluoro-1H-4-oxopyrimidin-2-yl)-β-D-glucopyranouronic acid methyl ester
3c.  1-(5-Fluoro-1H-4-oxopyrimidin-2-yl)-β-D-glucopyranouronic acid ethyl ester
4c.  1-(5-Fluoro-1H-4-oxopyrimidin-2-yl)-β-D-glucopyranouronic acid n-propyl ester
5c.  1-(5-Fluoro-1H-4-oxopyrimidin-2-yl)-β-D-glucopyranouronic acid isopropyl ester
6c.  1-(5-Fluoro-1H-4-oxopyrimidin-2-yl)-β-D-glucopyranouronic acid n-butyl ester
7c.  1-(5-Fluoro-1H-4-oxopyrimidin-2-yl)-β-D-glucopyranouronic acid isobutyl ester
8c.  1-(5-Fluoro-1H-4-oxopyrimidin-2-yl)-β-D-glucopyranouronic acid n-pentyl ester
9c.  1-(5-Fluoro-1H-4-oxopyrimidin-2-yl)-β-D-glucopyranouronic acid n-hexyl ester
10c.  1-(5-Fluoro-1H-4-oxopyrimidin-2-yl)-β-D-glucopyranouronic acid n-heptyl ester
11c.  1-(5-Fluoro-1H-4-oxopyrimidin-2-yl)-β-D-glucopyranouronic acid n-octyl ester
12c.  1-(5-Fluoro-1H-4-oxopyrimidin-2-yl)-β-D-glucopyranouronic acid amide
13c.  1-(5-Fluoro-1H-4-oxopyrimidin-2-yl)-β-D-glucopyranouronic acid dimethylamide
14c.  1-(5-Fluoro-1H-4-oxopyrimidin-2-yl)-β-D-glucopyranouronic acid diethylamide
15c.  1-(5-Fluoro-1H-4-oxopyrimidin-2-yl)-β-D-glucopyranouronic acid n-propylamide
16c.  1-(5-Fluoro-1H-4-oxopyrimidin-2-yl)-β-D-glucopyranouronic acid isopropylamide
17c.  1-(5-Fluoro-1H-4-oxopyrimidin-2-yl)-β-D-glucopyranouronic acid n-butylamide
18c.  1-(5-Fluoro-1H-4-oxopyrimidin-2-yl)-β-D-glucopyranouronic acid isobutylamide
19c.  1-(5-Fluoro-1H-4-oxopyrimidin-2-yl)-β-D-glucopyranouronic acid n-pentylamide
20c.  1-(5-Fluoro-1H-4-oxopyrimidin-2-yl)-β-D-glucopyranouronic acid benzylamide
21c.  1-{1-(5-Fluoro-1H-4-oxopyrimidin-2-yl)-β-D-glucopyranouronoyl}-pyrrolidine
22c.  1-{1-(5-Fluoro-1H-4-oxopyrimidin-2-yl)-β-D-glucopyranouronoyl}-piperidine
23c.  4-{1-(5-Fluoro-1H-4-oxopyrimidin-2-yl)-β-D-glucopyranouronoyl}-morpholine The novel compounds of formula (Ic) can be prepared by the processes as illustrated below.

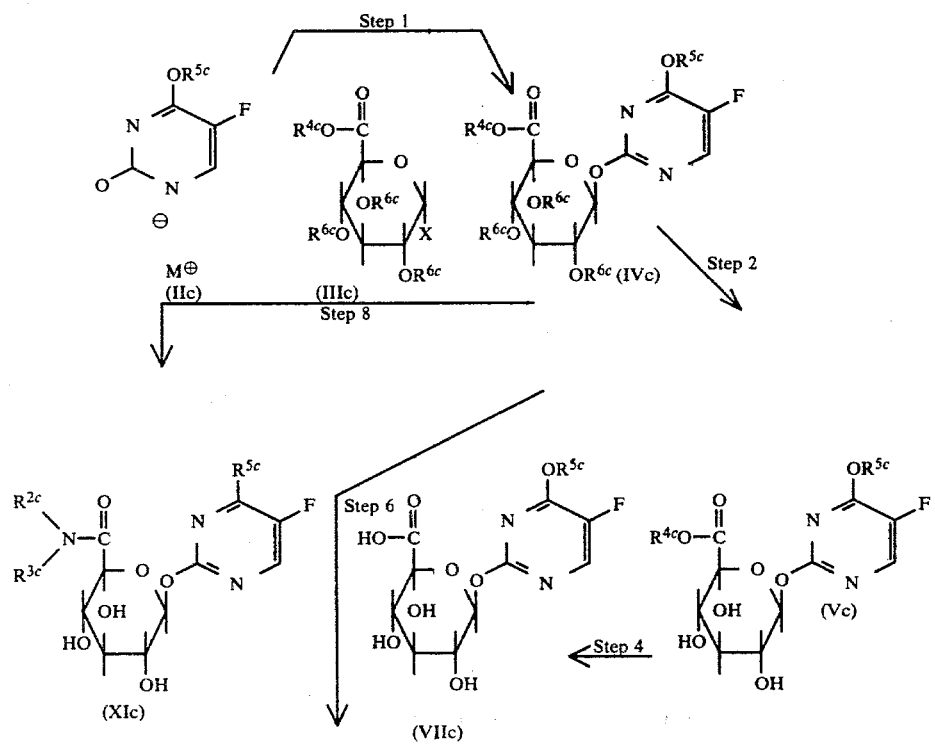

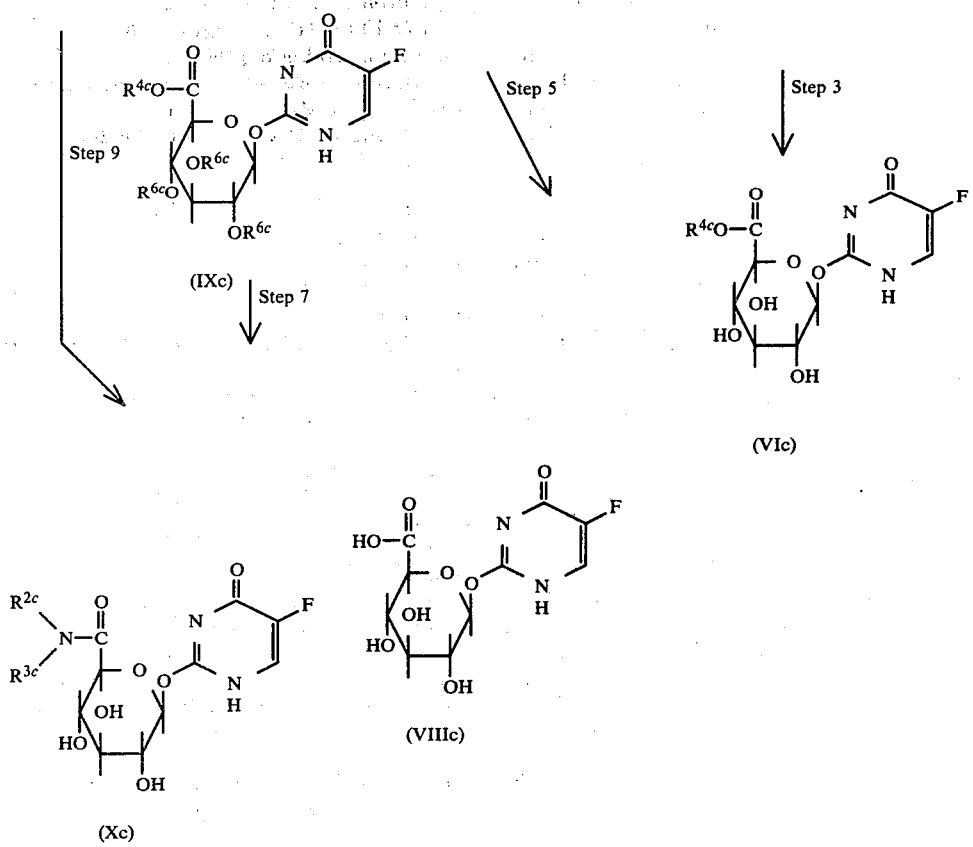

(VIc)

(Xc)

(VIIIc)

In the above formulae, $R^{2c}$ and $R^{3c}$ have the same meanings as defined hereinbefore; $R^{4c}$ represents an alkyl group, a cycloalkyl group, an aralkyl group or an aryl group, each corresponding to a group $R^{1c}OC-$ in formula (Ic), above, which represents a carboxylic acid ester group; $R^{5c}$ represents a protective group for a hydroxyl group which may be removed by reduction reaction, e.g., a benzyl group, the aromatic ring of which may be unsubstituted or substituted with a nitro group, a halogen atom such as chlorine, bromine and fluorine, or an ethyl group substituted at the β-position with one or more halogen atoms such as 2,2,2-trichloroethyl, 2,2-dibromoethyl, etc.; $R^{6c}$ represents an acyl group which may be employed as a protective group for a hydroxyl group, e.g., an aliphatic acyl group such as acetyl, n-propionyl, n-butyryl and isobutyryl, or an aromatic acyl group such as benzoyl, p-nitrobenzoyl, p-methylbenzoyl and p-methoxybenzoyl, etc.; an ion m⊕ represents a metal ion which may be employed in the reaction for preparing an O-glycoside compound by condensation of a heterocyclic base and a saccharide, e.g., a monovalent silver ion, a monovalent mercury ion, a divalent mercury ion as in HgCl and HgBr₂, an alkali metal ion such as a sodium ion, a potassium ion and the like; and X represents a halogen atom, e.g., chlorine, bromine, etc.

The first step is to prepare an O-glycoside compound of formula (IVc), above; a metal salt of 5-fluorouracil of formula (IIc) is subjected to condensation reaction with a halogenoglucopyranouronic acid ester of formula (IIIc). In carrying out the reaction of this step, the condensation reaction is conducted by contacting a compound of formula (IIc) with a compound of formula (IIIc) in the presence of a solvent.

As the solvents to be used, though not limited in particular as long as they do not participate in the present reaction, there may be preferred aromatic hydrocarbons, e.g., toluene, xylene, etc.; dialkyl aliphatic acid amides, e.g., dimethylformamide, dimethylacetamide, etc.; dialkylsulfoxides, e.g., dimethylsulfoxide, etc.; phosphoric acid amides, e.g., hexamethylphosphoroamide, etc.; nitroalkanes, e.g., nitromethane, etc.; and nitriles, e.g., acetonitrile. While the reaction temperature is not limited in particular, the reaction is carried out generally at 0°–150° C., but preferably at 100°–150° C. when a nonpolar solvent is used and at around room temperature when a polar solvent is used. The reaction period varies depending mainly upon the reaction temperature and the solvent to be used, but it is between around 5 minutes and 20 hours.

This reaction may also be conducted by a process which comprises, instead of using a metal salt of formula (IIc), adding mercuric cyanide in the presence of a solvent to a compound of formula (XIIc)

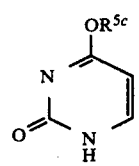

(XIIc)

wherein $R^{5c}$ has the same meaning as defined above, and then a halogenoglucopyranouronic acid of formula (IIIc), above, is added thereto with heating.

After completion of the reaction, desired compound (IVc) is obtained from the reaction mixture according to an ordinary method. For instance, after insoluble substances in the reaction mixture are filtered off, the solvent is removed by distillation under reduced pressure and the residue is extracted with an organic solvent such as chloroform. After the extract is washed with water and dried, the solvent is removed from the extract by distillation, an organic solvent such as ethanol is added to the residue so obtained and the mixture is allowed to stand in an ice room to obtain the desired compound as crystals.

The second step is to prepare a compound of formula (Vc), above; an acyl protective group of a hydroxyl group in a saccharide moiety is removed from a compound of formula (IVc). In carrying out this reaction, the reaction is conducted by contacting a compound of formula (IVc) with an alkali metal alkoxide in the presence of a solvent. As the alkali metal alkoxides to be used, preferred are sodium methoxide, sodium ethoxide, potassium tert-butoxide and the like. As the solvents to be used, though not limited as long as they do not participate in the present reaction, there may preferably be mentioned alcohols, e.g., methanol, ethanol, tert-butanol, etc.; ethers, e.g., tetrahydrofuran, dioxane, etc.; halogenated hydrocarbons, e.g., methylene chloride, chloroform, etc.; and aromatic hydrocarbons, e.g., benzene, toluene, xylene. While the reaction temperature is not limited in particular, the reaction is carried out generally at $-50°\sim50°$ C., but preferably at around 0° C. in particular. The reaction period is different depending mainly upon the reaction temperature but is between about 10 and 90 minutes.

After completion of the reaction, desired compound (Vc) of the present step is obtained from the reaction mixture according to an ordinary method. For instance, after the reaction mixture is neutralized by adding an acid such as dilute hydrochloric acid thereto and the solvent is removed by distillation, the resulting residue is dissolved in an organic solvent such as chloroform. Then, the organic solvent layer which is formed is washed with water and dried. Thereafter, the solvent is removed from the extract by distillation and the residue so obtained is purified by fractionation by column chromatography on silica gel. From the thus obtained eluate, which contains the desired product, the solvent is removed by distillation. To the residue thus produced is added an organic solvent such as ethanol and the resulting mixture is allowed to stand whereupon the desired product is obtained as crystals.

The third step is to prepare a glucuronic acid ester compound of formula (VIc) which is a desired compound of this invention; a protective group of the hydroxyl group in the pyrimidinine nucleus moiety is removed from a compound of formula (Vc) by reduction reaction. In carrying out the reduction, the reaction is carried out by contacting a compound of formula (Vc) with a reducing agent in the presence of a solvent. As the reducing agents, hydrogen and a catalyst for catalytic reduction such as palladium-carbon are preferable in cases where the protective group of the hydroxyl group is a substituted for unsubstituted benzyl group; and metallic zinc and acetic acid or an alochol such as methanol, ethanol, etc., are preferable in cases where the protective group of the hydroxyl group is an ethyl group substituted at its $\beta$-position with one or more halogen atoms. While the solvents to be used are not limited in particular as long as they do not participate in the present reaction, alcohols such as methanol, ethanol, etc., and ethers such as tetrahydrofuran, dioxane, etc., are preferable. The reaction temperature is not limited in particular but the reaction may preferably be carried out at around room temperature. The reaction period varies depending mainly upon the reducing agent but is between about 5 and 60 minutes.

After completion of the reaction, desired compound (VIc) is obtained according to an ordinary method. For instance, after insoluble substances are removed from the reaction mixture, the solvent is removed by distillation under reduced pressure. To the residue thus produced is added an organic solvent such as ethanol, and the resulting mixture is allowed to stand whereupon the desired product is obtained as crystals.

The fourth step is to prepare a compound of formula (VIIc); an ester compound of formula (Vc) is hydrolyzed. In carrying out the reaction of the fourth step, the reaction is conducted by contacting a compound of formula (Vc) with a hydrolyzing agent in the presence of a solvent. While the hydrolyzing agent is not limited in particular if it hydrolyzes only an ester group without influencing the other part of the compound, the reaction is preferably carried out at around pH 11 with ammonium hydroxide. As the solvents to be used, while not limited in particular as long as they do not participate in the reaction, a mixed solvent of an alcohol such as methanol, ethanol, etc., and water is preferable. While the reaction temperature is not limited in particular, the reaction is carried out generally at $-10°$ to $50°$ C., but may usually be carried out preferably, at around room temperature. The reaction period varies depending mainly upon the reaction temperature, but is between about 3 and 24 hours.

After completion of the reaction, desired compound (VIIc) is obtained according to an ordinary method. For instance, the solvent is removed from the reaction mixture by distillation under reduced pressure and the resulting residue is purified by fractionation by preparative thin layer chromatography on silica gel. The so obtained fraction of the desired compound is extracted with an organic solvent such as methanol and then the solvent is removed by distillation from the extract. After an organic solvent such as ethanol is added to the resulting residue, the mixture is allowed to stand in an ice room to obtain the desired product as crystals.

The fifth step is to prepare a glucronic acid compound of formula (VIIIc) which is a desired compound of this invention; a protective group of the hydroxyl group in the pyrimidine nucleus moiety is removed from a compound of formula (VIIc) by reduction reaction. The reaction conditions of the fifth step and the procedures of after-treatment are similar to those in the third step as mentioned above.

The sixth step is to prepare a compound of formula (IXc); a protective group of the hydroxyl group in the pyrimidine nucleus moiety is removed from a compound (IVc) by reduction reaction. The reaction conditions of this step and the procedures for after-treatment are similar to those in the third step as mentioned above.

The seventh step is to prepare a glucronic acid amide compound of formula (Xc) which is a desired compound of the present invention; acidamidation is conducted, simultaneously with removal of an acyl protective group for the hydroxyl group of the saccharide moiety from a compound of formula (IXc).

In carrying out the reaction of the seventh step, the reaction is conducted by contacting a compound of formula (IXc) with an amine of the formula

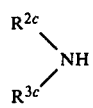 (XIIIc)

wherein $R^{2c}$ and $R^{3c}$ have the same meanings as defined above,
in the presence of a solvent. As the solvents to be used, while not limited in particular as long as they do not participate in the reaction, in alcohol such as methanol, ethanol, etc., is preferable. While the reaction temperature is not limited in particular, the reaction is carried out at 0° to 100° C., preferably at around room temperature is general. The reaction period varies depending mainly upon the reaction temperature but is between about 1 and 18 hours, preferably between about 12 and 18 hours in cases where the reaction is conducted at room temperature.

After completion of the reaction, desired compound (Xc) is obtained from the reaction mixture according to an ordinary method. For instance, the solvent is removed from the reaction mixture by distillation under reduced pressure and the desired product can be obtained by adding an organic solvent such as ethanol to the residue so obtained.

The eighth step is to prepare a compound of formula (XIc); acidamidation is conducted, simultaneously with removal of an acyl protective group for the hydroxyl group of the saccharide moiety from a compound of formula (IVc). The reaction conditions of the reaction in this step and the procedures for after-treatment are similar to those in the seventh step as mentioned above.

The ninth step is an alternative process to prepare a glucronic acid amide compound of formula (Xc) which is a desired compound of this invention; a protective group for the hydroxyl group on the pyrimidine nucleus moiety is removed from a compound of formula (XIc) by a reduction reaction. The reaction conditions for the reaction in this step and the procedures for after-treatment are similar to those in the third step as mentioned above.

Each desired compound which is obtained by each step mentioned above can, if necessary, be purified further by an ordinary method, e.g., recrystallization or reprecipitation method.

Compounds of formula (Ic) are illustrated by the following examples.

EXAMPLE 1c 1-(4-Benzyloxy-5-fluoropyrimidin-2-yl)-2,3,4-tri-O-acetyl-β-D-glucopyranouronic acid methyl ester

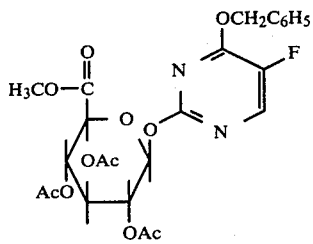

In 250 ml of dry xylene was suspended 5.23 g (16 mmol) of 4-benzyloxy-5-fluoro-1H-2-oxopyrimidine silver salt and the resulting suspension was refluxed while heating. The, about 50 ml of xylene was removed by azeotropic distillation to remove water. To the residual suspension was added 6.35 g (16 mmol) of 1-bromo-1-deoxy-2,3,5-tri-O-acetyl-α-D-glucopyranouronic acid methyl ester and the resulting mixture was refluxed with heating for 12 minutes. After completion of the reaction and allowing the heated material to cool, insoluble sustances precipitated and were then removed by filtration. The filtrate was condensed to dryness by distillation under reduced pressure. The resulting residue was dissolved in 100 ml of ethyl acetate and the solvent layer was washed successively with 50 ml of 5% aqueous sodium bicarbonate, 50 ml of saturated aqueous sodium chloride and 50 ml of water, and dried over anhydrous magnesium sulfate. To the caramel which was obtained, after removing the solvent by distillation under reduced pressure, was added a mixture of benzene and ethanol for crystallization to obtain 7.107 g of the desired product as white powdery crystals. From the mother liquor, 450 mg of secondary crystals were obtained. Melting point: 141° C.

Elementary analysis: for $C_{24}H_{25}O_{11}N_2F$ Calcd. C, 53.73; H, 4.70; N, 5.22; F, 3.54 Found C, 54.03; H, 4.68; N, 5.03; F, 3.56

Ultraviolet absorption spectrum: $\lambda_{max}^{0.1\ N\text{-}HCl\ in\ 50\%\ MeOH}$ nm (ε), 264 (8200); $\lambda_{max}^{50\%MeOH}$ nm (ε), 264 (8000); $\lambda_{max}^{0.1\ N\text{-}NaOH\ in\ 50\%\ MeOH}$ nm (ε), 265.5 (8200).

EXAMPLE 2c 1-(4-Benzyloxy-5-fluoropyrimidin-2-yl)-β-D-glucopyranouronic acid methyl ester

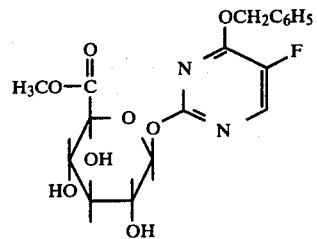

In a mixture of 18 ml of anhydrous methanol and 12 ml of methylene chloride was dissolved 5.9 g (11 mmol) of 1-(4-benzyloxy-5-fluoropyrimidin-2-yl)-2,3,4-tri-O-acetyl-β-D-glucopyranouronic acid methyl ester. To the resulting solution was added 5.5 ml of 1 N methanol solution of sodium methoxide with ice cooling. The mixture which formed was stirred as it stood for 1.5 hours. After completion of the reaction, 1 N hydrochloric acid was added to the reaction mixture to decrease the pH value of the solution to around 7 and the solvent was removed by distillation under reduced pressure. The residue which was obtained was dissolved in 50 ml of ethyl acetate, and the resulting solvent layer was washed with water and dried over anhydrous magnesium sulfate. Then, the solvent was removed by distillation under reduced pressure and 5.8 g of the crystalline residue so obtained was subjected to chromatography by using a column containing silica gel (4×22 cm). A fraction which was eluted with chloroform containing 5% of methanol was collected and the solvent was removed by distillation. Ethanol was added to the resulting residue, whereupon 2.735 g of the deisred compound were obtained as white crystals. Melting point: 146°–148° C.

Elementary analysis: for C₁₈H₁₉O₈N₂F Calcd. C, 52.68; H, 4.67; N, 6.83; F, 4.63 Found C, 52.25; H, 4.64; N, 7.03; F, 4.36

Ultraviolet absorption spectrum: $\lambda_{max}{}^{MeOH}$ nm ($\epsilon$), 265 (7700)

EXAMPLE 3c 1-(5-Fluoro-1H-4-oxopyrimidin-2-yl)-β-D-glucopyranouronic acid methyl ester

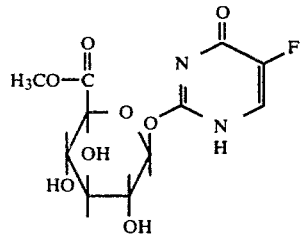

In 20 ml of anhydrous methanol was dissolved 0.65 g of 1-(4-benzyloxy-5-fluoropyrimidin-2-yl)-β-D-glucopyranouronic acid methyl ester. After the atmosphere of the reaction vessel for reduction was replaced with nitrogen gas, 130 mg of 10% palladium on carbon was added thereto and the resulting mixture was stirred for 8 minutes in a stream of hydrogen. After completion of the reaction, the catalyst was removed by filtration and the solvent was removed by distillation under reduced pressure. The residue so obtained was dissolved in a small amount of methanol. To the resulting solution was added acetone to precipitate a powder, followed by filtration to obtain 47 mg of the desired compound which shows a single spot on a thin layer chromatogram on silica gel developed with a solvent system composed of chloroform containing 30% of methanol. Melting point: 142°–145° C. (decomp.)

Elementary analysis: for C₁₁H₁₃O₈N₂F.3/2H₂O Calcd. C, 38.05; H, 4.64; N, 8.07;1 ; F, 5.47 Found C, 38.70; H, 4.56; N, 7.44; F, 5.00

Ultraviolet absorption spectrum: $\lambda_{max}$ 0.02 M-phosphate buffer (pH 6.86) nm ($\epsilon$), 267 (6400)

EXAMPLE 4c 1-(2-Benzyloxy-5-fluoropyrimidin-2-yl)-β-D-glucopyranouronic acid

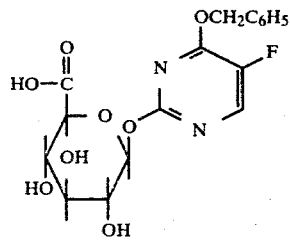

In 20 ml of a mixture of methanol, water and concentrated aqueous ammonia (6:3.9:0.1) was dissolved 821 mg (2.0 mmol) of 1-(4-benzyloxy-5-fluoropyrimidin-2-yl)-β-D-glucopyranouronic acid methyl ester obtained in Example 2c. The resulting solution was stirred at room temperature for 21 hours. Further, 0.2 ml of concentrated aqueous ammonia was added to the solution to adjust the pH value to 10–11 and the solution so obtained was stirred at room temperature for 48 hours. After completion of the reaction, the solvent was removed from the reaction mixture by distillation under reduced pressure. The thus obtained residue was dissolved in a small amount of methanol and was separated by preparative thin layer chromatography on silica gel. The powdery residue obtained by extraction with methanol was collected by filtration, after addition of ethanol thereto, to obtain 660 mg of the desired compound as a white powder. Melting point: 155°–159° C. (decomp.)

Elementary analysis: for C₁₇H₁₇O₈N₂F.3/2H₂O Calcd. C, 48.23; H, 4.76; N, 6.62; F, 4.49 Found C, 48.23; H, 5.13; N, 7.06; F, 4.10

Ultraviolet absorption spectrum: $\lambda_{max}{}^{MeOH}$nm ($\epsilon$), 266 (7800)

EXAMPLE 5c 1-(5-Fluoro-1H-4-oxopyrimidin-2-yl)-β-D-glucopyranouronic acid

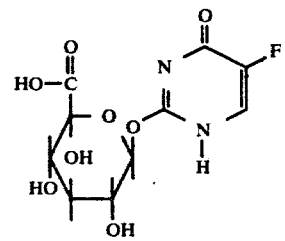

In 40 ml of anhydrous methanol was dissolved 500 mg (1.26 mmol) of 1-(2-benzyloxy-5-fluoropyrimidin-2-yl)-β-D-glucopyranouronic acid. After the atmosphere in the reaction vessel for reduction was replaced with nitrogen gas, 63 mg of 10% palladium on carbon was added to the solution and the mixture was stirred at room temperature until 22.5 ml of hydrogen was absorbed. After completion of the reaction, the catalyst was removed from the reaction mixture and the solvent was removed by distillation under reduced pressure. The thus obtained powdery residue, after suspension in anhydrous ethanol, was recovered by filtration, washed with anhydrous ethanol and dried to obtain 294 mg of the desired compound as white powders. Melting point: 146°–150° C. (decomp.)

Elementary analysis: for C₁₀H₁₁O₈N₂F.2/3C₂H₅OH.2H₂O Calcd. C, 36.49; H, 5.13; N, 7.51; F, 509 Found C, 36.62; H, 4.96; N, 7.57; F, 4.71

Ultraviolet absorption spectrum: $\lambda_{max}{}^{0.02}$M-phosphate buffer (pH 6.86) nm, 266.5

EXAMPLE 6c 1-(5-Fluoro-1H-4-oxopyrimidin-2-yl)-2,3,4-tri-O-acetyl-β-D-glucopyranouronic acid methyl ester

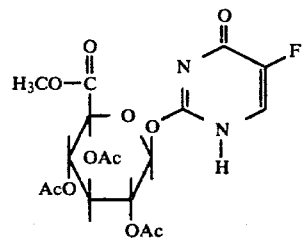

In 40 ml of anhydrous methanol was dissolved 0.55 g (1.04 mmol) of 1-(4-benzyloxy-5-fluoropyrimidin-2-yl)-2,3,4-tri-O-acetyl-β-D-glucopyranouronic acid methyl ester obtained in Example 1c. After the atmosphere in the reaction vessel for reduction was replaced with nitrogen gas, 0.11 g of 10% palladium on carbon was added to the solution and the resulting mixture was stirred for 7 minutes in a stream of hydrogen gas. After completion of the reaction, the catalyst was removed by filtration and the solvent was removed by distillation under reduced pressure. The thus obtained residue was crystallized by adding anhydrous ethanol thereto to obtain 378 mg of the desired compound as white crystals having a melting point of 165°–167° C.

Elementary analysis: for $C_{17}H_{19}O_{11}N_2F$ Calcd. C, 45.75; H, 4.29; N, 6.28; F, 4.26 Found C, 45.35; H, 4.35; N, 6.32; F, 4.02

Ultraviolet absorption spectrum: $\lambda_{max}^{MeOH}$ nm ($\epsilon$), 266 (6400)

EXAMPLE 7c 1-(5-Fluoro-1H-4-oxopyrimidin-2-yl)-β-D-glucopyranouronic acid amide

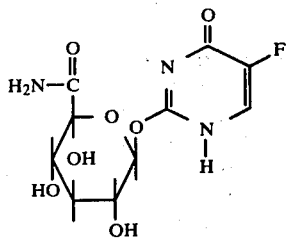

In 27 ml of anhydrous methanol was dissolved 357 mg (0.8 mmol) of 1-(5-fluoro-1H-4-oxopyrimidin-2-yl)-2,3,4,-tri-O-acetyl-β-D-glucopyranouronic acid methyl ester. The solution was saturated with ammonia by introducing dry ammonia thereinto and the solution thus obtained was allowed to stand overnight in a refrigerator. After completion of the reaction, the solvent was removed by distillation under reduced pressure and the resulting residue was dissolved in a small amount of methanol. After 10 ml of chloroform was added to the solution, the precipitate which formed was recovered by filtration and suspended in chloroform. The suspension was stirred for 30 minutes and then filtered to obtain 270 mg of a powder which showed a single spot on thin layer chromatogram on silica gel developed with chloroform containing 50% of methanol as the volvent system.

Melting point: 120°–125° C. (decomp.)

Elementary analysis: for $C_{10}H_{12}O_7N_3F\cdot H_2O$ Calcd. C, 37.16; H, 4.37; N, 13.00; F, 5.88 Found C, 37.05; H, 4.23; N, 12.85; F, 5.66

Ultraviolet absorption spectrum: $\lambda_{max}$ 0.02m-phosphate buffer (pH 6.86 nm ($\epsilon$), 268 (6700)

EXAMPLE 8c 1-(4-Benzyloxy-5-fluoropyrimidin-2-yl)-β-D-glucopyranouronic acid methylamide

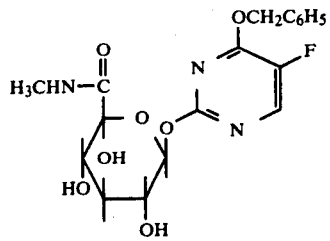

In 40 ml of anhydrous methanol was dissolved 590 mg (1.1 mmol) of 1-(4-benzyloxy-5-fluoropyrimidin-2-yl)-2,3,4-tri-O-acetyl-β-D-glucopyranouronic acid methyl ester. The resulting solution was saturated with methylamine by introducing dry methylamine thereinto and, after closing the vessel with a plug, was stirred at 0° C. for 35 hours. After completion of the reaction, the solvent was removed by distillation under reduced pressure and the residue thus obtained was suspended in anhydrous ethanol, followed by stirring for 30 minutes. The powder which precipitated was recovered by filtration, washed with anhydrous ethanol and dried to obtain 378 mg of the desired compound as a white powdery product which showed a single spot on thin layer chromatogram on silica gel developed with chloroform containing 10% of methanol as the developing solvent. Melting point: 181°–182° C. (decomp.)

Elementary analysis: for $C_{18}H_{20}O_7N_3F$ Calcd. C, 52.81; H, 4.92; N, 10.27; F, 4.64 Found C, 53.16; H, 5.21; N, 10.23; F, 4.34

Ultraviolet absorption spectrum: $\lambda_{max}^{MeOH}$ nm ($\epsilon$), 265 (7500)

EXAMPLE 9c 1-(5-Fluoro-1H-4-oxopyrimidin-2-yl)-β-D-glucopyranouronic acid methylamide

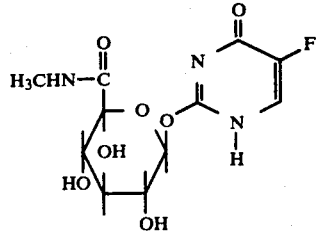

In 40 ml of anhydrous methanol was dissolved 300 mg (0.734 mmol) of 1-(4-benzyloxy-5-fluoropyrimidin-2-yl)-β-D-glucopyranouronic acid methylamide. After the atmosphere in the reaction vessel for reduction was replaced with nitrogen gas, 37 mg of 10% palladium on carbon was added to the resulting solution and the mixture which formed was stirred until 15 ml of hydrogen gas was absorbed. After completion of the reaction, the catalyst was removed by filtration and the solvent was removed by distillation under reduced pressure. The powdery residue thus obtained was suspended in anhydrous ethanol and collected by filtration after stirring for 30 minutes to obtain 142 mg of the desired compound as a white powder having a melting point of 130°–135° C. (decomp.).

Elementary analysis: for $C_{11}H_{14}O_7N_3F$ Calcd. C, 40.25; H, 4.61; N, 12.80; F, 5.79 Found C, 40.53; H, 4.67; N, 12.60; F, 5.85

Ultraviolet absorption spectrum: $\lambda_{max}$ 0.02 M-Phosphate buffer (pH 6.86) nm ($\epsilon$), 267 (7400)

COMPOUNDS (Id)

The 5-fluorouracil compounds of this invention include those of the formula (Id)

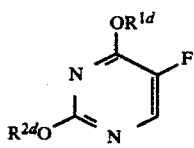

wherein one of $R^{1d}$ and $R^{2d}$ represents a group

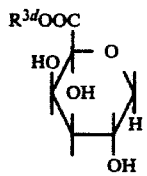

in which $R^{3d}$ represents a hydrogen atom, an alkyl group, a cycloalkyl group, an aralkyl group or an aryl group and the other represents a hydrogen atom.

In formula (Id), above, $R^{3d}$ represents a hydrogen atom; a straight-chain or branched alkyl group having from 1 to 8 carbon atoms such as, for example, methyl, ethyl, n-propyl, isopropyl, n-butyl, isobutyl, n-pentyl, isopentyl, n-hexyl, sec-hexyl, n-heptyl, n-octyl, 2-ethylhexyl, etc.; a cycloalkyl group having from 5 to 7 ring members such as, for example, cyclopentyl, cyclohexyl, cycloheptyl, etc.; an aralkyl group, the aromatic ring of which may be unsubstituted, e.g., benzyl, phenthyl, etc., or substituted with a lower alkyl group such as methyl, ethyl, n-propyl, isopropyl, n-butyl and isobutyl, a lower alkoxy group such as methoxy, ethoxy, n-propoxy, isopropoxy, n-butoxy and isobutoxy, or a halogen atom such as chlorine, bromine and fluorine; an aryl group, the aromatic ring of which may be unsubstituted, e.g., phenyl, etc., or substituted with a lower alkyl group such as methyl, ethyl, n-propyl, isopropyl, n-butyl and isobutyl, a lower alkoxy group such as methoxy, ethoxy, n-propoxy, isopropoxy, n-butoxy and isobutoxy, or a halogen atom such as chlorine, bromine and fluorine.

In formula (Id), $R^{3d}$ represents preferably a hydrogen atom or a straight-chain or branched alkyl group having from 1 to 6 carbon atoms.

Although formula (Id) above is shown in an enol form, it is considered that the compounds thereof generally exist in a keto form.

As compounds of formula (Id), above, the following are typical:

1d 1-(5-Fluoro-1H-12-oxopyrimidin-4-yl)-$\beta$-D-galactopyranouronic acid
2d 1-(5-Fluoro-1H-2-oxopyrimidin-4-yl)-$\beta$-D-galactopyranouronic acid methyl ester
3d 1-(5-Fluoro-1H-2-oxopyrimidin-4-yl)-$\beta$D-galactopyranouronic acid ethyl ester
4d 1-(5-Fluoro-1H-2-oxopyrimidin-4-yl)-$\beta$-D-galactopyranouronic acid n-propyl ester
5d 1-(5-Fluoro-1H-2-oxopyrimidin-4-yl)-$\beta$D-galactopyranouronic acid isopropyl ester
6d 1-(5-Fluoro-1H-2-oxopyrimidin-4-yl)-$\beta$-D-galactopyranouronic acid isobutyl ester
7d 1-(5-Fluoro-1H-2-oxopyrimidin-4-yl)-$\beta$-D-galactopyranouronic acid isobutyl ester 8d 1-(5-Fluoro-1H-4-oxopyrimidin-2-yl)-$\beta$-D-galactopyranouronic acid
9d 1-(5-Fluoro-1H-4-oxopyrimidin-2-yl)-$\beta$-D-galactopyranouronic acid methyl ester
10d 1-(5-Fluoro-1H-4-oxopyrimidin-2-yl)-$\beta$-D-galactopyranouronic acid ethyl ester
11d 1-(5-Fluoro-1H-4-oxopyrimidin-2-yl)-$\beta$-D-galactopyranouronic acid n-propyl ester
12d 1-(5-Fluoro-1H-4-oxopyrimidin-2-yl)-$\beta$-D-galactopyranouronic acid isopropyl ester 13d 1-(5-Fluoro-1H-4-oxopyrimidin-2-yl)-$\beta$-D-galactopyranouronic acid n-butyl ester
14d 1(5-Fluoro-1H-4-oxopyrimidin-2-yl)-$\beta$-D-galactopyranouronic acid isobutyl ester The novel compounds of formula (Id) can be prepared by the processes illustrated below.

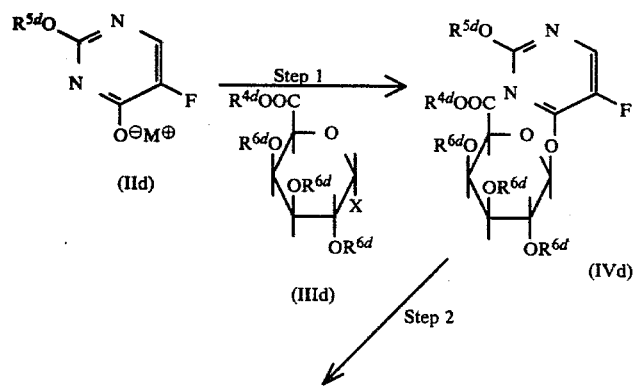

-continued
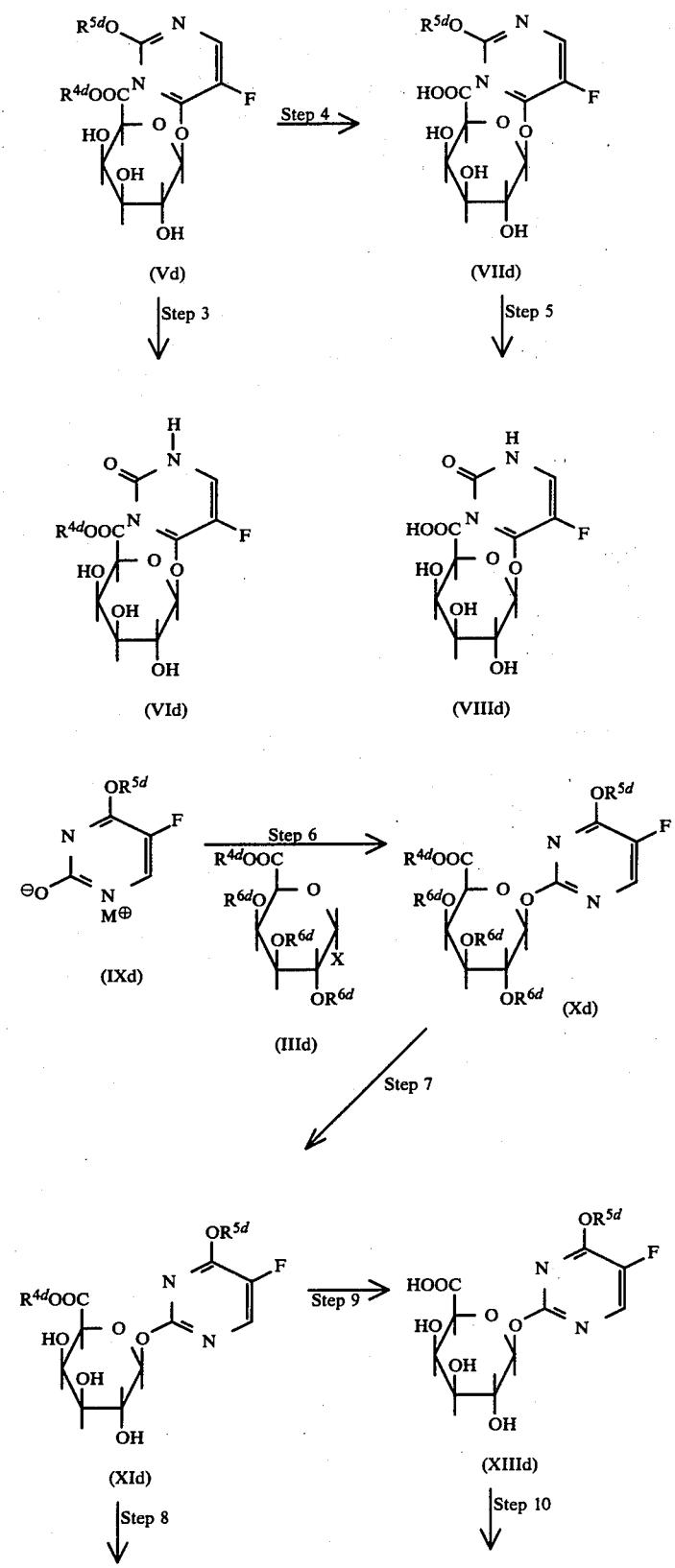

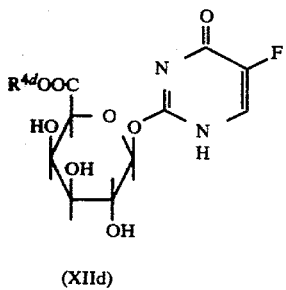

(XIId)

-continued

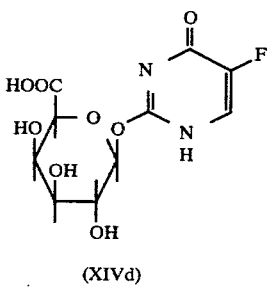

(XIVd)

In the above formulae, $R^{4d}$ represents an alkyl group, a cycloalkyl group, an aralkyl group or an aryl group, each corresponding to a group $R^{1d}OC$—in formula (Id), above, which represents a carboxylic acid ester group; $R^{5d}$ represents a protective group for a hydroxyl group which may be removed by reduction reaction, e.g., a benzyl group, the aromatic ring of which may be unsubstituted or substituted with a nitro group, a halogen atom such as chlorine, bromine, etc., or an ethyl group substituted at the β-position with one or more halogen atoms such as 2,2,2-trichloroethyl, 2,2-dibromoethyl, etc., $R^{6d}$ represents an acyl group which may be employed as a protective group for a hydroxyl group, e.g., an aliphatic acyl group such as acetyl, n-propionyl, n-butyryl, isobutyryl, etc., or an aromatic acyl group such as benzoyl, p-nitrobenzoyl, p-methylbenzoyl, p-methoxybenzoyl, etc.; an ion $M^{\oplus}$ represents a metal ion which may be employed in the reaction for preparing an O-glycoside compound by condensation of a heterocyclic base and a saccharide, e.g., a monovalent silver ion, a monovalent mercury ion, a divalent mercury ion such as $HgCl^{\oplus}$ and $HgBr^{\oplus}$, an alkali metal ion such as a sodium ion, a potassium ion and the like; and X represents a halogen atom, e.g., chlorine, bromine, etc.

The first step is to prepare an O-glycoside compound of formula (IVd) above; a metal salt of 5-fluorouracil of formula (IId) is subjected to condensation reaction with a halogenogalactopyranouronic acid ester of formula (IIId). The condensation reaction is conducted by contacting a compound of formula (IId) with a compound of formula (IIId) in the presence of a solvent.

As the solvents to be used, though not limited in particular as long as they do not participate in the present reaction, there may be preferred aromatic hydrocarbons, e.g., toluene, xylene, etc.; dialkyl aliphatic acid amides, e.g., dimethylformamide, dimethylacetamide, etc.; dialkylsulfoxides, e.g., dimethylsulfoxide, etc.; phosphoric acid amides, e.g., hexamethylphosphoroamide, etc.; nitroalkanes, e.g., nitromethane, etc.; and nitriles, e.g., acetonitrile, etc. While the reaction temperature is not limited in particular, the reaction is carried out generally at 0°-150° C., but preferably at 100°-150° C. when a nonpolar solvent is used and at around room temperature when a polar solvent is used. The reaction period of time varies depending mainly upon the reaction temperature and the solvent to be used, but it is between about 5 minutes and 20 hours.

The condensation reaction may also be conducted by a process which comprises, instead of using a metal salt of formula (IId), adding mercuric cyanide in the presence of a solvent to a compound of formula (XVd):

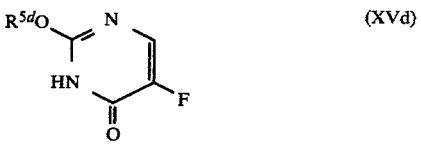

(XVd)

wherein $R^{5d}$ has the same meaning as defined above, and then a halogenogalactopyranouronic acid of formula (IIId), above, is added thereto while heating.

After completing of the reaction, desired compound (IVd) of the present step is obtained from the reaction mixture according to an ordinary method. For instance, after insoluble substances in the reaction mixture are filtered out, the solvent is removed by distillation under reduced pressure and the resulting residue is extracted with an organic solvent such as ethyl acetate, etc. After the extract is washed with water and dried, the solvent is removed from the extract by distillation and thus the desired compound can be obtained.

The second step is to prepare a compound of formula (Vd), above; an acyl protective group of a hydroxyl group in a saccharide moiety is removed from a compound of formula (IVd). This reaction is conducted by contacting a compound of formula (IVd) with an alkali metal alkoxide in the presence of a solvent. The alkali metal alkoxides used are preferably sodium methoxide, sodium ethoxide, potassium tert-butoxide and the like. As the solvents to be used, though not limited as long as they do not participate in the present reaction, there may preferably be mentioned alcohols, e.g., methanol, ethanol, tert-butanol, etc.; ethers, e.g., tetrahydrofuran, dioxane, etc.; halogenated hydrocarbons, et.g., methylene chloride, chloroform, etc.; and aromatic hydrocarbons, e.g., benzene, toluene, xylene, etc. While the reaction temperature is not limited in particular, the reaction is carried out generally at −30° C. to 50° C., but preferably at about −30° C. in particular. The reaction period is different depending mainly upon the reaction temperature but is between about 10 and 60 minutes.

After completion of the reaction, desired compound (Vd) of the present step is obtained from the reaction mixture according to an ordinary method. For instance, after the reaction mixture is neutralized by adding an acid such as acetic acid thereto and the solvent is removed by distillation, the residue is dissolved in an organic solvent such as ethyl acetate, etc. Then, the organic solvent layer is washed with water and dried. Thereafter, the solvent is removed from the extract by distillation so that the desired compound can be obtained.

The third step is to prepare a galactouronic acid ester compound of formula (VId) which is a desired compound of this invention; a protective group of the hydroxyl group in the pyrimidine nucleus moiety is removed from a compound of formula (Vd) by reduction reaction. This reaction is carried out by contacting a compound of formula (Vd) with a reducing agent in the presence of a solvent. As the reducing agents to be used, hydrogen and a catalyst for catalytic reduction such as palladium-carbon are preferable in cases where the protective group of the hydroxyl group is a substitutd or unsubstituted benzyl group; and metallic zinc and acetic acid or an alcohol such as methanol, ethanol, etc., are preferable in cases where the protective group of the hydroxyl group is an ethyl group substituted at its β-position with one or more halogen atoms. While the solvents to be used are not limited in particular as long as they do not participate in the present reaction, alcohols such as methanol, ethanol, etc., and ethers such as tetrahydrofuran, dioxane, etc., are preferable. The reaction temperature is not limited in particular but the reaction may preferably be carried out at about room temperature. The reaction period varies depending mainly upon the reducing agent but is between about 5 and 60 minutes.

After completion of the reaction, desired compound (VId) of the present step is obtained according to an ordinary method. For instance, after insoluble substances are removed by filtration from the reaction mixture, the solvent is removed by distillation under reduced pressure. To the residue thus produced is added an organic solvent such as ethanol and the mixture is allowed to stand to afford the desired product.

The fourth step is to prepare a compound of formula (VIId); an ester compound of formula (Vd) is hydrolyzed. This reaction is conducted by contacting a compound of formula (Vd) with a hydrolyzing agent in the presence of a solvent. While the hydrolyzing agent to be used is not limited in particular if it hydrolyzes only an ester group without influencing the other part of the compound, the reaction is preferably carried out at around pH 11 with ammonium hydroxide. As the solvents to be used, though not limited in particular as long as they do not participate in the reaction, a mixed solvent of an alcohol such as methanol, ethanol, etc., and water is preferable. While the reaction temperature is not limited in particular, the reaction is carried out generally at −10° to 50° C., but may usually be carried out preferably at about room temperature. The reaction period varies depending mainly upon the reaction temperature, but is between about 3 and 24 hours.

After completion of the reaction, desired compound (VIId) of the present step is obtained according to an ordinary method. For instance, the solvent is removed from the reaction mixture by distillation under reduced pressure and the resulting residue is purified by fractionation by preparative thin layer chromatography on silica gel. The fraction so obtained of the desired compound is extracted with an organic solvent such as methanol and then the solvent is removed by distillation from the extract. After an organic solvent such as ethanol is added to the residue, the mixture is allowed to stand in an ice room to afford the desired product.

The fifth step is to prepare a galactouronic acid compound of formula (VIIId) which is a desired compound of this invention; a protective group of the hydroxyl group in the pyrimidine nucleus moiety is removed from a compound of formula (VIId) by reduction reaction. The reaction conditions of the reaction in this step and the procedures for the after-treatment are similar to those in the third step mentioned above.

The sixth step is to prepare an O-glycoside compound of formula (Xd), above; a metal salt of 5-fluorouracil of formula (IXd) is subjected to condensation reaction with a halogenogalactopyranouronic acid ester of formula (IIId). While the reaction conditions of this reaction are similar to those mentioned above in the first step, the reaction may also be carried out by a process which comprises, instead of using a metal salt of formula (IXd), adding mercuric cyanide in the presence of a solvent to a compound of formula (XVId):

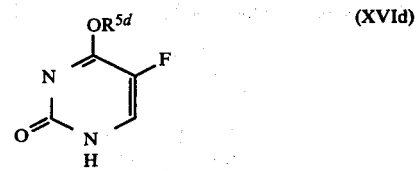

wherein $R^{5d}$ has the same meaning as defined above, and then a halogenogalactopyranouronic acid ester of formula (IIId) mentioned above is added thereto while heating. After completion of the reaction, the desired compound (Xd) of the present step is obtained from the reaction mixture according to an ordinary method, using an after-treatment similar to that in the first step mentioned above.

The seventh step is to prepare a compound of formula (XId), above; an acyl group for protecting a hydroxyl group in the saccharide moiety is removed from a compound of formula (Xd). The reaction conditions and the after-treatment in this step are similar to those in the second step mentioned above.

The eighth step is to prepare a galactouronic acid ester compound of formula (XIId) which is a desired compound of this invention; a protective group for the hydroxyl group on the pyrimidine nucleus moiety is removed from a compound of formula (XId) by reduction reaction. The reaction conditions for the reaction in this step and the procedures for after-treatment are similar to those in the third step as mentioned above.

The ninth step is to prepare a compound of formula (XIIId); an ester compound of formula (XId) is hydrolyzed. The reaction conditions for the reaction in this step and the procedures for after-treatment are similar to those in the fourth step as mentioned above.

The tenth step is to prepare a galactouronic acid compound of formula (XIVd) which is a desired compound of this invention; a protective group for the hydroxyl group on the pyrimidine nucleus moiety is removed from a compound of formula (XIIId) by reduction reaction. The reaction conditions for the reaction in this step and the procedures for after-treatment are similar to those in the third step as mentioned above.

Each desired compound which is obtained by each step mentioned above can, if necessary, be purified further by an ordinary method, e.g., gas chromatography, recrystallization or reprecipitation.

Compound of formula (Id) are illustrated in the following examples.

EXAMPLE 1d 1-(2-Benzyloxy-5-fluoropyrimidin-4-yl)-2,3,4-tri-O-acetyl-β-D-galactopyranouronic acid methyl ester

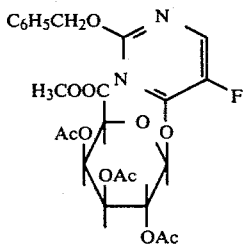

In 320 ml of dry toluene was suspended 7.9 g of the silver salt of 2-benzyl-5-fluorouracil. To remove water, about 90 ml of the solvent was removed by distillation using a water separator and the residual suspension was allowed to cool. To the residual suspension was added 9.1 g of 2,3,5-tri-O-acetyl-1-bromo-1-deoxy-α-D-galactopyranouronic acid methyl ester and the resulting mixture was heated under reflux for 30 minutes. After completion of the reaction, insoluble substances which precipitated after being allowed to cool were removed by filtration and the solvent was removed by distillation under reduced pressure. The residue was dissolved in 300 ml of ethyl acetate and washed successively with 200 ml of water, 300 ml of 5% aqueous sodium hydrogen carbonate and 200 ml of 20% aqueous sodium chloride in turn. Then, each water layer was extracted with 200 ml of ethyl acetate. After the organic layers were combined and dried over anhydrous magnesium sulfate, the solvent was removed by distillation, so that a caramel-like residue was obtained. This residue was purified by column chromatography on silica gel using chloroform as a developing solvent to give 10.1 g of the desired captioned compound as a caramel-like substance which showed a single spot on a thin layer chromatograph.

Elementary Analysis (%): for $C_{24}H_{25}O_{11}N_2F$ Calcd. C, 53,73; H, 4.70; N, 5.22; F, 3.54 Found C, 53.96; H, 4.55; N, 5.20; F, 3.52

Ultraviolet absorption spectrum: $\lambda_{max}^{0.1\ N-HCl,\ MeOH}=271$ nm, $\lambda_{max}^{MeOH}=271$ nm, $\lambda_{max}^{0.1\ N-NaOH,\ MeOH}=270$ nm.

EXAMPLE 2d 1-(2-Benzyloxy-5-fluoropyrimidin-4-yl)-β-D-galactopyranouronic acid methyl ester

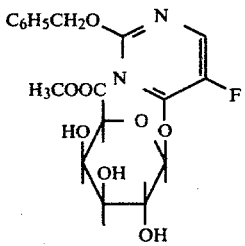

To 160 ml of a solution of sodium methoxide in methanol, which was previously prepared by dissolving 0.55 g of metallic sodium in 160 ml of anhydrous methanol and was cooled to −30° C., was added 6.44 g of 1-(2-benzyloxy-5-fluoropyrimidin-4-yl)-2,3,4-tri-O-acetyl-β-D-galactopyranouronic acid methyl ester, and the reaction was carried out under anhydrous conditions at −30° C. for 6 hours. After 2.01 g of acetic acid dissolved in 10 ml of anhydrous methanol was added thereto and the neutrality of the medium was confirmed, the reaction mixture was evaporated to dryness under reduced pressure to give a caramel-like residue, which was then dissolved in 90 ml of ethyl acetate and washed once with 100 ml of phosphate buffer solution (pH 7.0) and twice with 60 ml of 10% aqueous sodium chloride. Each aqueous layer was extracted with 50 ml of ethyl acetate in turn, and the ethyl acetate layers were combined with each other and dried over anhydrous magnesium sulfate. Then, the solvent was removed by distillation under reduced pressure. When most of the ethyl acetate was removed, 50 ml of isopropanol was added to the residual mixture and the solvent was further removed gradually. When the smell of ethyl acetate was lost, a white powdery substance precipitated. This was collected by filtration and dried to give 1.8 g of the desired captioned compound.

Elementary analysis (%): for $C_{18}H_{19}O_8N_2F$ Calcd. C, 52.68; H, 4.67; N, 6.83; F, 4.63 Found C, 52.81; H, 4.50; N, 6.91; F, 4.42

Ultraviolet absorption spectrum: $\lambda_{max}^{H_2O}=270$ nm

EXAMPLE 3d 1-(5-Fluoro-1H-2-oxopyrimidin-4-yl)-β-D-galactopyranouronic acid methyl ester

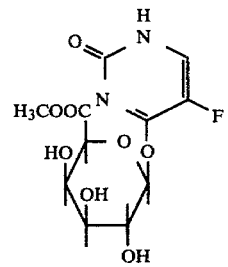

In 90 ml of anhydrous methanol was dissolved 2.46 g of 1-(2-benzyloxy-5-fluoropyrimidin-4-yl)-β-D-galactopyranouronic acid methyl ester. After the mixture was stirred for 15 minutes in a stream of hydrogen, the atmosphere in the reaction vessel was replaced with nitrogen gas. Then, 300 mg of 10% palladium on carbon was added thereto and 134 ml of hydrogen gas was absorbed at an ordinary temperature under atmospheric pressure. After the catalyst was removed by filtration, the solvent was evaporated under reduced pressure at a bath temperature of below 30° C. When most of the methanol was removed by evaporation, 30 ml of ethanol was added to the residual mixture and the evaporation was continued further. This procedure was repeated twice and a white powdery product was collected by filtration to give 1.1 g of the desired captioned compound.

Elementary analysis (%): for $C_{11}H_{13}O_8N_2F$ Calcd. C, 41.26; H, 4.09; N, 8.75; F, 5.93 Found C, 41.55; H, 4.30; N, 8.77; F, 5.99

Ultraviolet absorption spectrum: $\lambda_{max}$ 0.02 M phosphate buffer (pH 6.86)=288 nm

EXAMPLE 4D 1-(2-Benzyloxy-5-fluoropyrimidin-4-yl)-β-D-galactopyranouronic acid

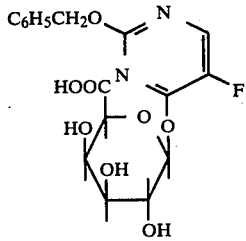

In 23 ml of a mixture of methanol, water and concentrated aqueous ammonia (6:3.9:0.1) was dissolved 1.0 g of 1-(2-benzyloxy-5-fluoropyrimidin-4-yl)-β-D-galactopyranouronic acid methyl ester obtained in Example 2d, and the solution was allowed to stand for 24 hours with stirring. After completion of the reaction, the solvent was removed from the reaction mixture by distillation under reduced pressure and 1.1 g of a caramel-like residue was obtained.

The residue thus obtained was subjected to preparative thin layer chromatography to separate a fraction containing the desired compound by using chloroform containing 35% of methanol as a developing solvent. The fraction was extracted with methanol followed by removal of the methanol from the extract to give a caramel-like residue. After ethanol was added to the residue and the mixture was allowed to stand in a refrigerator, a powdery substance precipitated. This was collected by filtration to give the desired captioned compound.

Elementary analysis (%): for $C_{17}H_{17}O_8N_2F \cdot 2H_2O$ Calcd. C, 47.23; H, 4.90; N, 6.48; F, 4.39 Found C, 47.56; H, 4.51; N, 6.32; F, 4.21

Ultraviolet absorption spectrum: $\lambda_{max}^{H2O} = 269$ nm

EXAMPLE 5d 1-(5-Fluoro-1H-2-oxopyrimidin-4-yl)-β-D-galactopyranouronic acid

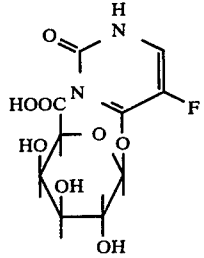

In 20 ml of anhydrous methanol was dissolved 396 mg of 1-(2-benzyloxy-5-fluoropyrimidin-4-yl)-β-D-galactopyranouronic acid. After the atmosphere in the reaction vessel was replaced with nitrogen gas, 50 mg of 10% palladium on carbon was added to the solution and the resulting mixture was stirred at an ordinary temperature under atmospheric pressure until 22 ml of hydrogen gas was absorbed. After completion of the reaction, the catalyst was removed by filtration from the reaction mixture. When most of the methanol was removed by distillation under reduced pressure, anhydrous ethanol was added to the residual mixture and then the solvent was removed further by distillation. A white powdery substance produced was collected by filtration, washed with anhydrous ethanol and dried to give the desired captioned compound.

Elementary analysis (%): for $C_{10}H_{11}O_8N_2F$ Calcd. C, 39.22; H, 3.62; N, 9.15; F, 6.20 Found C, 39.45; H, 3.45; N, 9.32; F, 5.95

Ultraviolet absorption spectrum: $\lambda_{max}$ 0.02 M phosphate buffer (pH 6.86) = 288 nm

COMPOUNDS (Ie)

5-fluorouracil compounds of formula (Ie) and pharmaceutically acceptable salts thereof are also included herein:

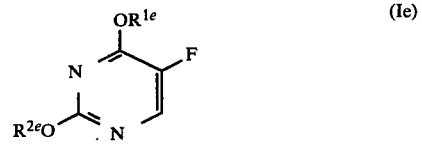
(Ie)

wherein one of $R^{1e}$ and $R^{2e}$ represents a group with the following formula:

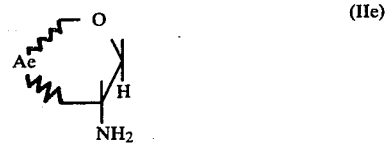
(IIe)

wherein Ae represents a group having the following formulae:

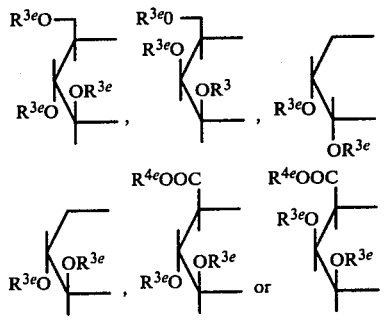

wherein $R^{3e}$ represents a hydrogen atom or an acyl group; $R^{4e}$ represents a hydrogen atom, an alkyl, a cycloalkyl, an aralkyl or an aryl group and the other of $R^{1e}$ and $R^{2e}$ represents a hydrogen atom.

Formula (Ie) is represented by an enol form but seems to be usually a keto form.

In formula (IIe), $R^{3e}$ represents a hydrogen atom, or a protecting group used for protecting hydroxyl groups in sugars e.g. a straight or branched aliphatic acyl group having form 1 to 5 carbon atoms such as formyl, acetyl, n-propionyl, n-butyryl, isobutyryl, pivaloyl, valeryl or isovaleryl, an aromatic acyl group which may be substituted with a lower alkyl group such as methyl, ethyl, n-propyl, isopropyl, n-butyl or isobutyl, a lower alkoxy group such as methoxy, ethoxy, n-propoxy, isopropoxy, n-butoxy or isobutoxy or a halogen atom such as fluorine, chlorine or bromine; $R^{4e}$ represents a hydrogen atom; a straight or branched alkyl group having 1 to 8 carbon atoms such as methyl, ethyl, n-propyl, isopropyl, n-butyl, isobutyl, n-pentyl, isopentyl, n-hexyl, sec-hexyl, n-heptyl, n-octyl or 2-ethyl-hexyl; a cycloalkyl group having from 5 to 7 carbon atoms such as cyclopentyl, cyclohexyl or cycloheptyl; an aralkyl group such as benzyl or phenethyl which may be substituted with a lower alkyl group such as methyl, ethyl, n-propyl, isopropyl, n-butyl or isobutyl; a lower alkoxyl group such as methoxy, ethoxy, n-propoxy, isopropoxy or isobutoxy or a halogen atom such as fluorine, chlorine or bromine; an aryl group such as phenyl which may be substituted with a lower alkyl group such as methyl, ethyl, n-propyl, isopropyl, n-butyl or isobutyl, a lower alkoxyl group such as methoxy, ethoxy, n-propoxy, isopropoxy, n-butoxy or isobutoxy, or a halogen atom such as fluorine, chlorine or bromine.

Particularly in formula (IIe), $R^{3e}$ preferably represents a hydrogen atom or a straight or branched aliphatic acyl group having from 2 to 4 carbon atoms, $R^{4e}$ preferably represents a hydrogen atom or a straight or branched alkyl group having from 1 to 6 carbon atoms.

Compounds of formula (Ie) can also be transformed into pharmaceutically acceptable salts, if desired. Such salts may be acid addition salts of a mineral acid such as hydrochloric acid, hydrobromic acid or phosphoric acid or an organic acid such as oxalic acid, succinic acid, maleic acid or citric acid.

Compounds of formula (Ie) are exemplified as follows:

(1e)  $O^4$-(2-amino-2-deoxy-$\beta$-D-glucopyranosyl)-5-fluorouracil (2e)  $O^4$-(2-amino-2-deoxy-$\beta$-D-galactopyranosyl)-5-fluorouracil (3e)  $O^4$-(2-amino-2-deoxy-$\beta$-D-ribopyranosyl)-5-fluorouracil (4e)  $O^4$-(2-amino-2-deoxy-$\beta$-D-xylopyranosyl)-5-fluorouracil (5e)  $O^2$-(2-amino-2-deoxy-$\beta$-D-glucopyranosyl)-5-fluorouracil (6e)  $O^2$-(2-amino-2-deoxy-$\beta$-D-galactopyranosyl)-5-fluorouracil (7e)  $O^2$-(2-amino-2-deoxy-$\beta$-D-ribopyranosyl)5-fluorouracil (8e)  $O^2$-(2-amino-2-deoxy-$\beta$-D-xylopyranosyl)-5-fluorouracil and acylated compounds in which hydroxyl groups of sugar parts are acylated with acetyl, n-propionyl, n-butryl or isobutyryl groups (9e)  $O^4$-(2-amino-2-deoxy-$\beta$-D-gluçopyranouronyl)-5-fluorouracil (10e)  $O^2$-(2-amino-2-deoxy-$\beta$-D-glucopyranouronyl)-5-fluorouracil (11e)  $O^4$-(2-amino-2-deoxy-$\beta$-D-galactopyranouronyl)-5-fluorouracil (12e)  $O^2$-(2-amino-2-deoxy-$\beta$-D-galactopyranouronyl)-5-fluorouracil and esterified compounds in which the carboxylic acid part is esterified with a methyl, n-propyl, isopropyl, n-butyl, isobutyl, n-pentyl, isopentyl or n-hexyl group and further acylated compounds of these in which the hydroxyl group of sugar parts is acylated with an acetyl, n-propionyl, n-butyryl or isobutyryl group.

Compounds of (Ie) can be prepared by the following steps:

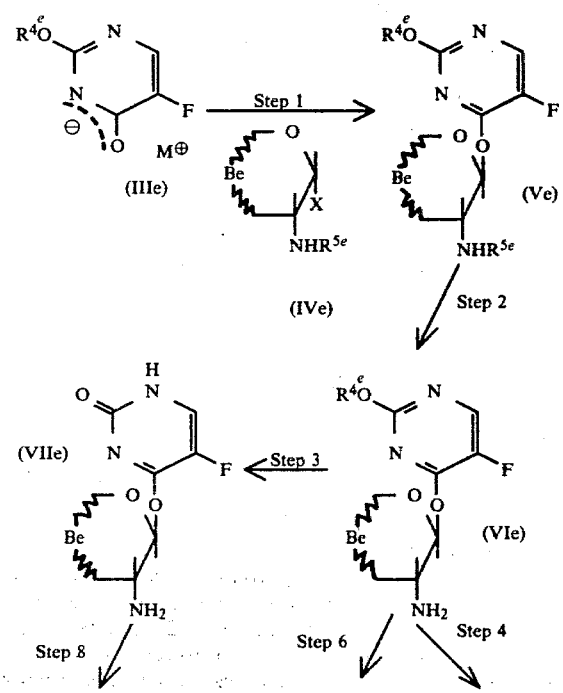

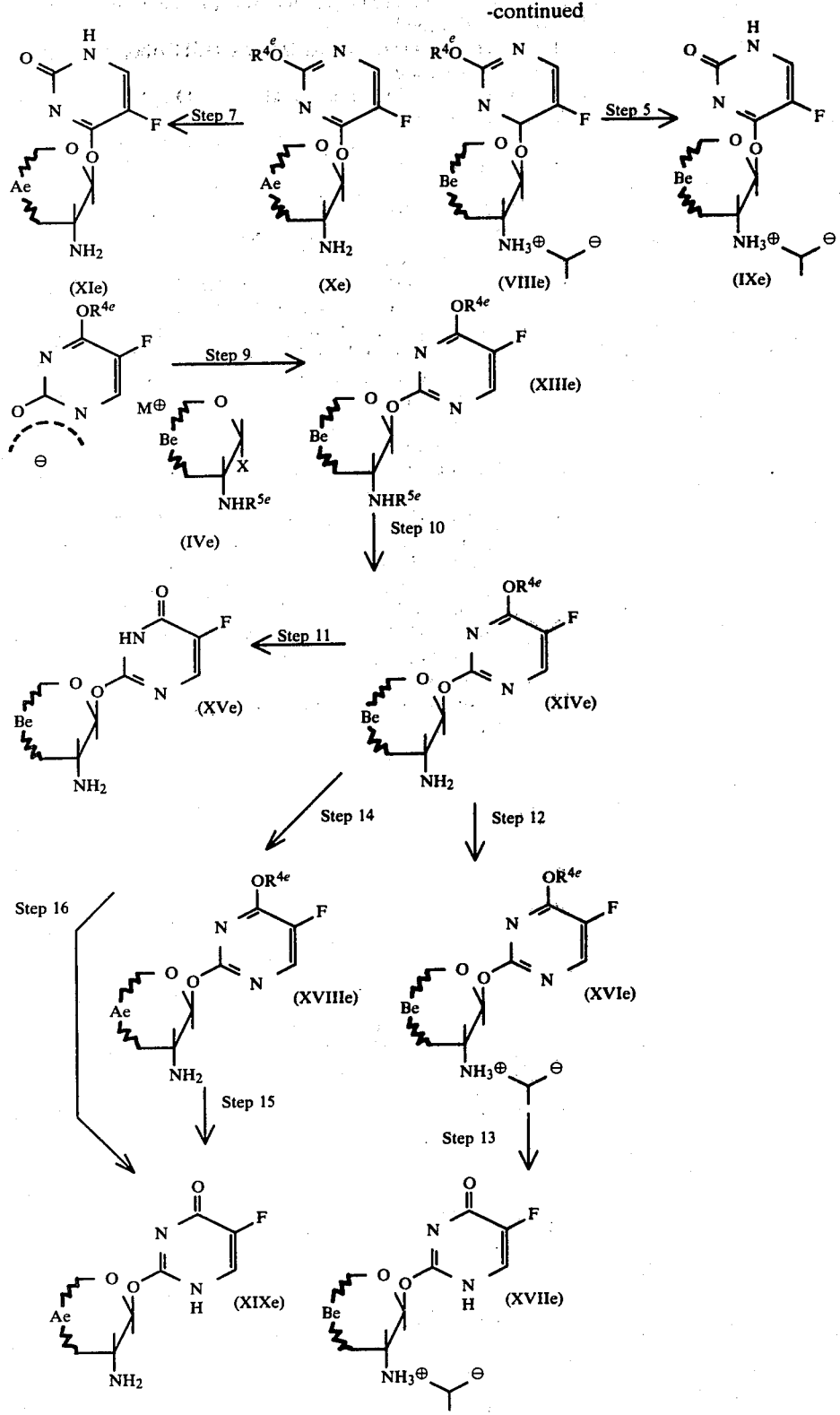

In the above formulae, Ae is the same as defined above; $R^{4e}$ represents a protecting group for the hydroxyl group in a pyridine nucleus which can be removed by reduction such as the benzyl group which may be substituted with a nitro group or a halogen atom, e.g. chlorine or bromine; $R^{5e}$ represents a protecting group for the amino group in the sugar part which can be removed by reduction as a halogenoethoxycarbonyl, e.g. 2,2,2-trichloroethoxycarbonyl and 2,2-dibromoethoxycarbonyl, or a benzyloxycarbonyl which may be substituted with nitro or a halogen atom such as chlorine or bromine, Be is the same as in $R^{3e}$ and $R^{4e}$ of Ae providing that a hydrogen atom is excluded; $M^{\oplus}$ represents a metallic ion used for preparation of an O-glucoside by condensation of a heterocyclic base and a sugar, such as monovalent silver or monovalent or divalent mercury e.g. $HgCl^{\oplus}$ or $HgBr^{\oplus}$ or an alkali metal, e.g. sodium or potassium; X represents a halogen atom such as chlorine or bromine; and $Y^{\ominus}$ represents an acid addition salt of a mineral acid such as hydrochloric acid, hydrobromic acid or phosphoric acid or an organic acid such as oxalic acid, succinic acid, maleic acid or citric acid.

The preparation of this invention can be carried out by optional combined reactions of condensation between 5-fluorouracil metal salts and halogenosugars and the reactions for removing protecting groups for the hydroxyl group in the pyrimidine nucleus and sugar part, but will be explained in detail for each of the steps by following the above reaction steps.

The first step is a process of preparing an O-glucoside of formula (Ve), which is a step of condensing a 5-fluorouracil metal salt of formula (IIIe) and a halogenopyranose of formula (IVe). The reaction of this step can be carried out by contacting a compound of formula (IIIe) with a compound of formula (IVe) in a solvent. Solvents used are not limited as far as they are inert for this reaction and are preferably aromatic hydrocarbons such as toluene and xylene, aliphatic acid dialkylamides such as dimethylformamide and dimethylacetamide, dialkylsulfoxides such as dimethylsulfoxide, phosphoric acid amides such as hexamethylphosphoroamide, nitroalkanes such as nitromethane and nitriles such as acetonitrile. The reaction temperature is not limited and is usually at a temperature of 0° to 150° C. It is preferably at a temperature of 100° to 150° C. in the case of a non-polar solvent and near room temperature in the case of a polar solvent. The reaction time mainly varies with the reaction temperature and the solvent used but is at a range of about 5 minutes to 30 hours.

This reaction can also be carried out by adding mercuric cyanide to a compound of formula (XXe):

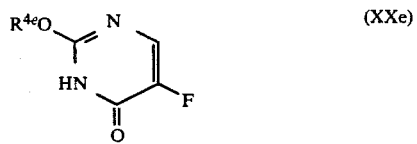

(XXe)

wherein $R^{4e}$ is the same as defined above instead of a metal salt of formula (IIIe), and then adding a halogenopyranose of formula (IVe) thereto while heating in a solvent.

After completion of the reaction, the object compound (Ve) of this step can be taken out from the reaction mixture by a conventional method. For example, after filtering off an insoluble substance from the reaction mixture, the filtrate is distilled under reduced pressure and the resulting residue is extracted with an organic solvent such as ethyl acetate. The extract is washed with water, dried and distilled to give the object compound.

The second step is a process for preparing a compound of formula (VIe) which is a step of removing the protecting group for the amino group in the sugar part by reduction. This reaction can be carried out by contacting a compound of formula (Ve) with a reducing agent in a solvent. Reducing agents used are preferably zinc metal in cases where the protecting group for the amino group is a halogenoethoxycarbonyl group, and a catalytic reduction catalyst such as hydrogen and palladium on carbon in cases where it is the benzyloxycarbonyl group. In the latter catalytic reduction, the protecting group for the hydroxyl group in the pyrimidine nucleus of the compound of formula (Ve) is also removed at the same time. The reaction conditions and after-treatment method are the same as in the third step and will be explained in the third step.

In cases where zinc is used as a reducing agent, solvents used are preferably aliphatic acids such as oxalic acid and acetic acid and alcohols such as methanol, ethanol and propanol and a combined solvent of water and these organic solvents. The reaction temperature is not limited but is preferably near room temperature. The reaction time is usually at a range of 1 to 5 hours.

After completion of the reaction, the object compound (VIe) of this step can be taken out from the reaction mixture by conventional methods. For example, after filtration of an undissolved substance from the reaction mixture, the filtrate is distilled under reduced pressure and an organic solvent such as ethanol is added to the residue and allowed to stand to give crystals, which are filtered out.

The third step is a process for preparing a $O^4$-($\beta$-D-glucopyranosyl)-5-fluorouracil of formula (VIIe), which is a step of removing the protecting group for the hydroxyl group in the pryimidine nucleus of a compound of formula (VIe). This reaction can be carried out by contacting a compound of formula (VIe) with a reducing agent in a solvent. The reducing agent used is not limited for removing a protecting group such as benzyl group, but it is preferably a catalytic reduction agent such as hydrogen and palladium on carbon. Solvents used are not limited as far as they are inert for the reaction and are preferably alcohols such as methanol and ethanol and ethers such as tetrahydrofuran and dioxan. The reaction temperature is not particularly limited but is preferably near room temperature. The reaction time is usually a period required for absorption of one equivalent of hydrogen.

After completion of the reaction, the object compound (VIIe) of this step can be taken out from the reaction mixture by conventional methods. For example, after filtering off an insoluble substance which forms, the filtrate is distilled under reduced pressure and an organic solvent such as ethanol is added to the residue and allowed to stand to give crystals, which are filtered out.

The fourth step is a process for preparing a compound of formula (VIIIe), which is a step of converting a compound of formula (VIe) into its acid addition salt. This reaction can be carried out by adding an acid forming a salt to a compound of formula (VIe) in a solvent. Acids used are mineral acids such as hydrochloric acid, hydrobromic acid and phosphoric acid, and organic acids such as oxalic acid, succinic acid, maleic acid and citric acid. Solvents used are not particularly limited but are preferably non-polar solvents which can dissolve the raw material (VIe) and cause the resulting acid addition salt to crystallize. These solvents are preferably ethers such as acetone, and methyl ethyl ketone. The reaction is carried out with ice-cooling.

After completion of the reaction, the object compound (VIIIe) of this step can be taken out from the reaction mixture by conventional methods. For example, the crystals from the reaction mixture are filtered out.

The fifth step is a process for preparing an acid addition said of O⁴-(β-D-glycopyranosyl)-5-fluoroacil of formula (IXe), which is a step of removing a protecting group for the hydroxyl group in the pyrimidine nucleus in a compound of formula (VIIIe) by reduction. The reaction conditions and the after-treatments of this step are the same as in the third step.

The sixth step is a process for preparing a compound of formula (Xe), which is a step of removing the acyl protecting group for the hydroxyl group in the sugar part of a compound of formula (VIe) and further, if necessary, of hydrolysing the uronic acid ester part.

The reaction for removing the acyl protecting group for the hydroxyl group can be carried out by contacting a compound of formula (VIe) with a base such as ammonia or an alkali metal alkoxide in a solvent. Bases used are preferably ammonia, sodium methoxide, sodium ethoxide or potassium tert-butoxide. Solvents used are not limited so long as they are inert for this reaction and are preferably alcohols such as methanol, ethanol and tert-butanol, and a mixed solvent of the said alcohol and an ether such as tetrahydrofuran and dioxan or a halogeno-hydrocarbon such as methylenechloride and chloroform.

The reaction can preferably be carried out in anhydrous conditions. The reaction temperature is not limited and is preferably at a temperature of −30° to 50° C. and particularly at a temperature of −30° C. to room temperature. The reaction time mainly varies with the reaction temperature and is usually at a range of 2 to 20 hours.

After completion of the reaction, the object compound obtained by the reaction for removing the acyl protecting group can be taken out from the reaction mixture by conventional methods. For example, after adjusting pH of the reaction mixture to about 6–7, the reaction mixture is distilled under reduced pressure and with the addition of ethyl acetate and phosphoric acid buffer solution (pH 6.5) crystals are formed. The crystals are filtered out.

Next, the optional hydrolysis of the uronic acid ester part can be carried out by contacting the compound obtained by removing the acyl protecting group with a hydrolysing agent in a solvent. Hydrolysing agents used are not limited so long as they can hydrolyse only an ester group without affecting other parts. This hydrolysis can preferably be carried out at a pH of about 11 with ammonium hydroxide. Solvents used are not limited so long as they are inert for this reaction and are preferably a mixed solvent of an alcohol such as methanol or ethanol and water. The reaction temperature is not particularly limited but is at a temperature of 10° to 50° C. and preferably near room temperature. The reaction time mainly varies with the reaction temperature and is at a range of about 3 to 24 hours.

After completion of the reaction, the object compound of this hydrolysis reaction can be taken out by conventional methods. For example, the reaction mixture is distilled under reduced pressure and the resulting residue is purified by subjecting it to a thin layer partition chromatography using silica gel for partition, and the partition obtained is extracted with an organica solvent such as methanol and the elute is distilled. An organic solvent such as ethanol is added to the residue and allowed to stand in a refrigerator to give crystals.

The seventh step is a process of preparing a O⁴-(β-D-glucopyranosyl)-5-fluorouracil of formula (XIe), which is a step of removing the protecting group for the hydroxyl group in the pyrimidine nucleus of a compound of formula (Xe). The reaction conditions and after-treatments are the same as in the third step.

The eighth step is another process of preparing a O⁴-(β-D-glycopyranosyl)-5-fluorouracil of formula (XIe), which is a step of removing an acyl protecting group for the hydroxy group of a compound of formula (VIIe) and further, if necessary, of hydrolysing the ester part. The reaction conditions and after-treatments are the same as in the sixth step.

The ninth step is a process for preparing a O-glycoside of formula (XIIIe), which is a step of condensing a 5-fluorouracil metal salt of formula (XIIe) with a halogenopyranose of formula (IVe). The reaction conditions are the same as in the first step, but this reaction can be carried out by adding mercuric cyamide to a compound of formula (XXIe):

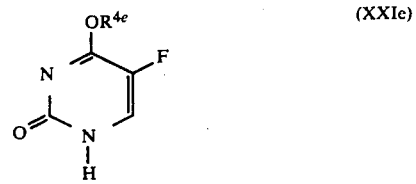

in which R⁴ᵉ is defined as above in a solvent, instead of a metal salt of formula (XIIe), and further adding a halogenopyranose of formula (IVe) thereto while heating.

After completion of the reaction, the object compound (XIIIe) of this step can be removed from the reaction mixture using the same after-treatments as in the first step according to conventional methods.

The tenth step is a process for preparing a compound of formula (XIVe), which is a step for removing a protecting group for the amino group of the sugar part in a compound of formula (XIIIe). The reaction conditions and after-treatments are the same as in the second step.

The eleventh step is a process for preparing a O²-(β-D-glycopyranosyl)-5-fluorouracil of formula (XVe), which is a step of removing the protecting group for the hydroxyl group in the pyrimidine nucleus of a compound of formula (XIVe). The reaction conditions and after-treatments of this step are the same as in the third step.

The twelfth step is a process for preparing a compound of formula (XVIe), which is a step of producing an acid addition salt of a compound of formula (XIVe). The reaction conditions and after-treatments are the same as in the fourth step.

The thirteenth step is a process of preparing an acid addition salt of a O²-(β-D-glycopyranosyl)-5-fluorouracil of formula (XVIIe), which is a step of removing the protecting group for the hydroxyl group in the pyrimidine nucleus of a compound of formula (XVIe). The reaction conditions and after-treatments are the same as in the third step.

The fourteenth step is a process for preparing a compound of formula (XVIIIe), which is a process of removing the acyl protecting group for the hydroxyl group of a sugar part in a compound of formula (XIVe) and further hydrolysing the uronic acid ester part, if necessary. The reaction conditions and after-treatments are the same as in the sixth reaction.

The fifteenth step is a process for preparing a O²-(β-D-glycopyranosyl)-5-fluorouracil of formula (XIXe), which is a step of removing the protecting group for the hydroxyl group in the pyrimidine nucleus of a compound of formula (XVIIIe). The reaction conditions and after-treatments are the same as in the third step.

The sixteenth step is another process for preparing a O²-(β-D-glycopyranosyl)-5-fluorouracil of formula (XIXe), which is a step of removing the acyl protecting group for the hydroxyl group in the sugar part of a compound of formula (XVe) and further hydrolysing the ester part, if necessary. The reaction conditions and after-treatments are the same as in the sixth step.

The object compounds obtained by the above steps can be purified, if necessary, by conventional methods, for example, recrystallisation, column chromatography or reprecipitation.

Compounds of formula (Ie) are illustrated by the following examples.

EXAMPLE 1e

O²-benzyl-O⁴-(3,4,6-tri-O-acetyl-2-deoxy-2-trichloroethoxycarbonylamino-β-D-glucopyranosyl)-5-fluorouracil

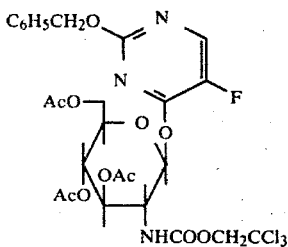

In 710 ml. of anhydrous toluene, which was dehydrated with calcium hydride and distilled, was suspended 23.1 g. (71 mmol.) of O²-benzyl-5-fluorouracil silver salt. The resulting suspension was refluxed to distill about 50 ml. of toluene under azeotropic distillation in order to remove water and allowed to cool at room temperature. A solution of 33.6 g. (71 mmol.) of 3,4,6-tri-O-acetyl-2-deoxy-2-trichloroethoxycarboxylamino-2-α-D-glucopyranosyl bromide in 100 ml. of dried toluene was added to the suspension and refluxed for 15 minutes without stirring. After completion of the reaction, a crystallized undissolved substance was filtered off and the filtrate was concentrated and dried under reduced pressure to obtain a caramel-like residue, which was dissolved in 500 ml. of ethyl acetate and washed with 300 ml. of 5% aqueous sodium hydrogen carbonate solution and 500 ml. of saturated sodium chloride solution. After filtering an undissolved substance, the organic layer was dried with anhydrous magnesium sulfate and the solvent was evaporated under reduced pressure to give 43.2 g. of the desired product as a caramel-like substance. This raw substance can be purified by subjecting it to silica gel column chromatography using chloroform containing 1% methanol as developing solvent, but can be used for the following step as it was.

Ultraviolet absorption spectrum: $\lambda_{max}^{0.1\ N\text{-}HCl\ in\ MeOH}$ nm($\epsilon$): 270 (6950). $\lambda_{max}^{MeOH}$ nm($\epsilon$): 271 (7260). $\lambda_{max}^{0.1\ N\text{-}NaOH\ in\ MeOH}$ nm($\epsilon$): 272 (7310).

NMR spectrum: $\delta$(CDCl₃): 6.30 (d, H at 1'-position, $J_{1'\text{-}2'}=8.5$ cps)

Elementary anaylsis C₂₆H₂₇O₁₁N₃Cl₃F·¼CHCl₃ Calculated: C, 43.77; H, 3.81; N, 5.81; F, 2.56. Found: C, 43.88; H, 3.66; N, 6.04; F, 2.56.

EXAMPLE 2e

O²-benzyl-O⁴-(3,4,6-tri-O-acetyl-2-amino-2-deoxy-β-D-glucopyranosyl)-5-fluorouracil

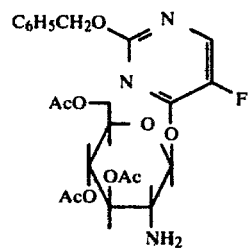

In 200 ml. of 80% acetic acid was dissolved 43.2 g. (63.0 mmol.) of O²-benzyl-O⁴-(3,4,6-tri-O-acetyl-2-deoxy-2-trichloroethoxycarbonylamino-β-D-glucopyranosyl)-5-fluorouracil. 20.4 g. (31.5 mmol.) of zinc dust was added to 330 ml. of 80% acetic acid and stirred for about 5 minutes and cooled to about 20° C. with ice-cooling. The former solution was added with stirring to the zinc dust suspension and stirred further for 1 hour and 10 minutes after addition of 80% acetic acid. After completion of the reaction, an undissolved substance was filtered off and the solvent was evaporated under reduced pressure to give a residue, which was dissolved in 300 ml. of ethyl acetate and washed with 300 ml. of ice-water, 500 ml. of 5% aqueous sodium hydrogen carbonate solution, 200 ml. of water and 200 ml. of saturated saline solution. Each of the water layers was extracted with 100 ml. of ethyl acetate and the combined ethyl acetate was dried with anhydrous magnesium sulfate and distilled under reduced pressure. The residue was dissolved in 200 ml. of ethanol and the solution was distilled to about 100 ml. and allowed to stand overnight at about 5° C. to give crystals, which were filtered out and dried to give 14.38 g. of the object compound (melting point, 141° to 142° C.) as colorless crystals.

Ultraviolet absorption spectrum: $\lambda_{max}^{0.1\ N\text{-}HCl\ in\ MeOH}$ nm($\epsilon$): 270 (6900). $\lambda_{max}^{MeOH}$ nm($\epsilon$): 271 (6990). $\lambda_{max}^{0.1\ N\text{-}NaOH\ in\ MeOH}$ nm($\epsilon$): 270 (6880).

NMR spectrum: $\delta$(CDCl₃): 8.24 (d, H at 6-position, $J_{6H\text{-}F}=2.0$ cps), 5.90 (d, H at 1'-position, $J_{1'\text{-}2'}=8.5$ cps), 5.40 (s, -CH₂-C₆H₅).

Elementary analysis: C₂₃H₂₆O₉N₃F Calculated: C, 54.44; H, 5.16; N, 8.28; F, 3.74 Found: C, 54.18; H, 5.44; N, 8.28; F, 3.45.

EXAMPLE 3e

O⁴-(3,4,6-tri-O-acetyl-2-amino-2-deoxy-β-D-glucopyranosyl)-5-fluorouracil

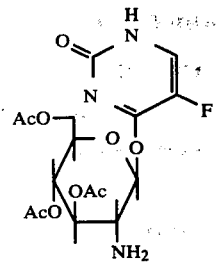

In 50 ml. of anhydrous ethanol was dissolved 517 mg. of O²-benzyl-O⁴-(3,4,6-tri-O-acetyl-2-amino-2-deoxy-β-D-glucopyranosyl)-5-fluorouracil and after the content of the vessel for reduction was replaced with dried nitrogen gas, the solution was stirred after addition of 50 mg. of 10% palladium-on-charcoal under ordinary pressure until 20 ml. of hydrogen gas was absorbed. After completion of the reduction, the catalyst was filtered off and the filtrate was concentrated under reduced pressure. The resulting residue was dissolved in 5 ml. of anhydrous methanol and after addition of an additional 20 ml. of anhydrous ethanol the solutioan was concentrated under reduced pressure to give crystals, which were filtered and dried to give 250 mg. of the desired product having a melting point of 129° to 130° C. (decomp.).

Ultraviolet absorption spectrum: $\lambda_{max}^{MeOH}$ nm (ε): 291 (5010)

NMR spectrum: δ (DMSO-d₆): 8.13 (d, H at 6-position, $J_{6H-F}$=5.5 cps), 6.06 (d, H at 1'-position, $J_{1'-2'}$=8.0 cps)

Elementary analysis: $C_{16}H_{20}O_9N_3F \cdot H_2O$ Calculated: C, 44.14; H, 5.09; N, 9.65; F, 4.36 Found: C, 44.05; H, 4.77; N, 9.39; F, 3.87.

EXAMPLE 4e

O²-benzyl-O⁴-(3,4,6-tri-O-acetyl-2-amino-2-deoxy-β-D-glucopyranosyl)-5-fluorouracil hydrochloric acid salt

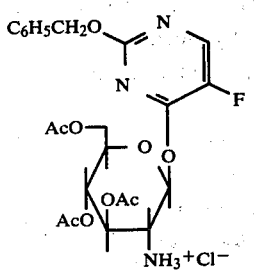

In 160 ml. of acetone was dissolved 3.04 g. (6 mmol.) of O²-benzyl-O⁴-(3,4,6-tri-O-acetyl-2-amino-2-deoxy-β-D-glucopyranosyl)-5-fluorouracil obtained in Example 2e, and a solution of 1.96 ml. of ether containing 0.95 equivalent of hydrochloric acid in 40 ml. of acetone was added dropwise thereto. After completion of the reaction, a white precipitate which formed was filtered, washed with acetone and dried to give 2.67 g. of the desired product, having a melting point of 171° to 172° C. (decomp.), as white crystals. The filtrate was concentrated to give a crystalline residue, to which 20 ml. of acetone was added and an additional 378 mg. of the desired product was obtained by filtering the residue, washing with acetone and drying.

Ultraviolet absorption spectrum: $\lambda_{max}^{MeOH}$ nm(ε): 270 (7030)

NMR spectrum: δ(DMSO-d₆): 8.63 (d, H at 6-position, $J_{6H-F}$=2.7 cps), 6.78 (d, H at 1'-position, $J_{1'-2'}$=8.5 cps)

Elementary analysis: $C_{23}H_{26}O_9N_3F \cdot HCl$ Calculated: C, 50.79; H, 5.00; N, 7.73; Cl, 6.52; F, 3.49 Found: C, 50.84; H, 4.98; N, 7.80; Cl, 6.55; F, 3.30.

EXAMPLE 5e

O⁴-(3,4,6-tri-O-acetyl-2-amino-2-deoxy-β-D-glucopyranosyl)-5-fluorouracil hydrochloric acid salt

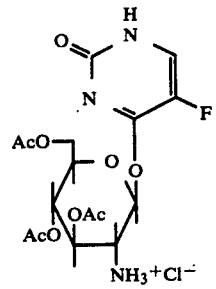

In 50 ml. of anhydrous methanol was dissolved 544 mg. of O²-benzyl-O⁴-(3,4,6-tri-O-acetyl-2-amino-2-deoxy-β-D-glucopyranosyl)-5-fluorouracil hydrochloric acid salt, and the atmosphere of the vessel for reduction was replaced with dried nitrogen gas and, after adding 50 mg. of 10% palladium-on-charcoal, the solvent was reduced with stirring under ordinary pressure until 20 ml. of nitrogen gas was absorbed. After completion of the reaction, the catalyst was filtered and the filtrate was concentrated to give crystals, which were filtered out, washed with anhydrous ethanol and dried to give white crystals of the desired product having a melting point of 112°–116° C. (decomp.)

Elementary analysis: $C_{16}H_{20}O_9N_3F \cdot HCl \cdot H_2O$ Calculated: C, 40.73; H, 4.70; N, 8.91, Cl, 7.51; F, 40.3 Found: C, 40.66; H, 4.67; N, 9.55; Cl, 7.23; F, 3.57.

EXAMPLE 6e

O²-benzyl-O⁴-(2-amino-2-deoxy-β-D-glucopyranosyl)-5-fluorouracil

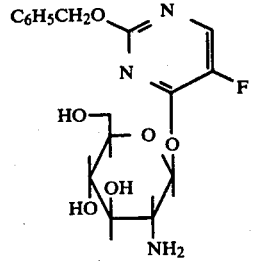

In 30 ml. of anhydrous methanol and 20 ml. of methylene chloride was dissolved 2.06 g. (4 mmol.) of O²-benzyl-O⁴-(3,4,6-tri-O-acetyl-2-amino-2-deoxy-β-D-glucopyranosyl)-5-fluorouracil and the solution was cooled to −35° C. After addition of a solution of 8 ml. of 1 N sodium methoxide in methanol, the resulting solution was kept at −30° to −25° C. for 2 hours. After the resulting solution was cooled to −40° C., 10 ml. of anhydrous methanol in 528 mg. of acetic acid was added thereto and after a solution of anhydrous methanol in 0.1 ml. of acetic acid was added dropwise to adjust pH to 6–7, the solution which formed was evaporated under reduced pressure to obtain a gel-like residue. To this residue were added 50 ml. of 0.1 M phosphoric acid buffer solution (pH 6.5) and 50 ml. of ethyl acetate, and the resulting mixture was stirred well to give a precipitate, which was crushed, filtered out, washed with 20 ml. of each of ethyl acetate and water and dried to give 597 mg. of the desired product, melting point of 124° to 126° C. (decomp.), as white crystals.

Ultraviolet absorption spectrum: $\lambda_{max}^{MeOH}$ nm ($\epsilon$): 270 (6930)

NMR spectrum: $\delta$ (d$^6$-DMSO): 8.50 (d, H at 6-position, $J_{6H-F}$=2.5 cps), 5.83 (d, H at 1'-position, $J_{1'-2'}$=8.0 cps), 5.40 (s, -CH$_2$-C$_6$H$_5$)

Elementary analysis: $C_{17}H_{20}O_6N_3F$ Calculated: C, 53.54; H, 5.29; N, 11.02; F, 4.93 Found: C, 53.50; H, 5.45; N, 11.03; F, 4.51.

EXAMPLE 7e

O$^4$-(2-amino-2-deoxy-$\beta$-D-glucoyranosyl)-5-fluorouracil

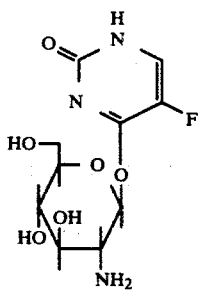

In 60 ml of anhydrous methanol was dissolved 762 mg (2 mmol.) of O$^2$-benzyl-O$^4$-(2-amino-2-deoxy-$\beta$-D-glucopyranosyl)-5-fluorouracil and the atmosphere of the vessel for reduction was replaced with dried nitrogen gas and, after addition of 100 mg of 10% palladium-on-charcoal, the resulting solution was reduced with stirring at room temperature until 46 ml of hydrogen was absorbed. After completion of the reaction, the catalyst was filtered off and the filtrate was concentrated under reduced pressure to give crystals, which were filtered out after addition of a small amount of anhydrous ethanol and dried to give white crystals having a melting point of 120° to 130° C. (decomp.).

Elementary analysis: $C_{10}H_{14}O_6N_3F \cdot H_2O \cdot CH_3OH$ Calculated: C, 38.71; H, 5.91; N, 12.31; F, 5.57 Found: C, 38.59; H, 5.62; N, 12.06; F, 5.26.

EXAMPLE 8e

O$^4$-benzyl-O$^2$-(3,4,6-tri-O-acetyl-2-deoxy-2-trichloroethoxycarbonylamino-$\beta$-D-glucopyranosyl)-5-fluorouracil

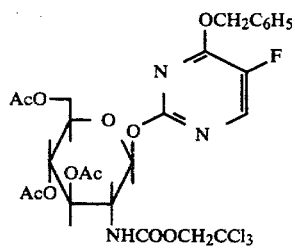

In 330 ml of anhydrous toluene, which was dehydrated with calcium hydride and distilled, was suspended 10.8 g (33 mmol.) of O$^4$-benzyl-5-fluorouracil silver salt and the suspension was refluxed to distill about 30 ml of toluene under azeotropic distillation in order to remove water. It was then allowed to cool at room temperature. To this suspension was added a solution of 17.9 g (33 mmol.) of 3,4,6-triacetyl-2-deoxy-trichloroethoxycarbonylamino-$\alpha$-D-glucopyranosyl bromide in 30 ml of anhydrous toluene and the resulting mixture was refluxed for 30 minutes. After completion of the reaction, a crystallized precipitate was filtered off and the filtrate was distilled under reduced pressure. The residue so obtained was dissolved in 200 ml of ethyl acetate and washed once with 150 ml of 5% aqueous sodium hydrogen carbonate solution, and twice with 200 ml of water. Each of the water layers was extracted with 50 ml of ethyl acetate and the combined organic layer was dried with anhydrous magnesium sulfate and distilled under reduced pressure to give 26.3 g of a caramel-like desired product. This raw product can be purified by subjecting it to silica gel chromatography using chloroform containing 1% methanol as a developing solvent, but can be used in the following step without purification.

Ultraviolet absorption spectrum: $\lambda_{max}^{0.1\ N-HCl\ in\ MeOH}$ nm ($\epsilon$): 265 (6900) $\lambda_{max}^{H_2O-MeOH}$ nm ($\epsilon$): 265 (8200) $\lambda_{max}^{0.1\ N-NaOH\ in\ MeOH}$ nm ($\epsilon$): 266 (8000)

NMR spectrum: $\delta$ (CDCl$_3$): 8.48 (d, H at 6-position, $J_{6H-F}$=2.6 cps), 6.18 (d, H at 1'-position, $J_{1'-2'}$=9.0 cps), 5.55 (s, -CH$_2$-C$_6$H$_5$)

Elementary analysis: $C_{26}H_{27}O_{11}N_3Cl_3F \cdot \frac{1}{8}CHCl_3 \cdot \frac{1}{8}CH_3OH$ Calculated: C, 44.80; H, 4.11; N, 5.89; Cl, 16.76; F, 2.66 Found: C, 44.63; H, 3.82; N, 5.57; Cl, 16.72; F, 2.41.

EXAMPLE 9e

O$^4$-benzyl-O$^2$-(3,4,6-tri-O-acetyl-2-amino-2-deoxy-$\beta$-D-glucopyranosyl)-5-fluorouracil

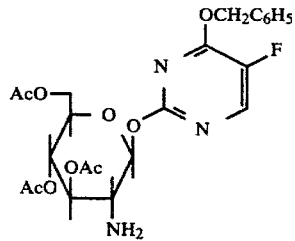

In 250 ml of 80% acetic acid was added 9.8 g (150 mmol.) of zinc dust and the resulting suspension was stirred at room temperature and cooled to about 20° C. To this suspension was added a solution of 20.5 g (30 mmol.) of $O^4$-benzyl-$O^2$-(3,4,6-tri-O-acetyl-2-deoxy-2-trichloroethoxycarbonylamino-$\beta$-D-glucopyranosyl)-5-fluorouracil in 80 ml of 80% acetic acid and the mixture which formed was stirred at room temperature for 2 hours. After completion of the reaction, a dissolved substance was filtered off and the solvent was distilled under reduced pressure to give a caramel-like residue, which was dissolved in 300 ml of aqueous 5% sodium hydrogen carbonate and washed once with 300 ml of ice-water. 300 ml of aqueous sodium hydrogen carbonate solution, and 300 ml of ice-water respectively. Each of the water layers was extracted with 100 ml of ethyl acetate and the combined organic layer was dried over anhydrous magnesium sulfate and distilled to give a residue, which was dissolved in ethanol and the solution was concentrated to give crystals, which were filtered out and dried to give 10.7 g of the desired product having a melting point of 61° to 62° C.

Ultraviolet absorption spectrum: $\lambda_{max}^{0.1\ N\text{-}HCl\ in\ MeOH}$ nm ($\epsilon$): 263.5 (8300) $\lambda_{max}^{H2O\text{-}MeOH}$ nm ($\epsilon$): 265 (8200) $\lambda_{max}^{0.1\ N\text{-}NaOH\ in\ MeOH}$ nm ($\epsilon$): 265 (8200)

NMR spectrum: $\delta$ (DMSO-$d_6$): 8.49 (d, H at 6-position, $J_{6H\text{-}F}$=2.6 cps), 5.94 (d, H at 1'-position, $J_{1'\text{-}2'}$=8.5 cps), 5.58 (s, -CH$_2$-C$_6$H$_5$)

Elementary analysis: $C_{23}H_{26}O_9N_3F\cdot\frac{1}{2}C_2H_5OH$ Calculated: C, 54.34; H, 5.51; N, 7.92; F, 3.58 Found: C, 53.91; H, 5.31; N, 8.00; F, 3.50.

EXAMPLE 10e $O^2$-(3,4,6-tri-O-acetyl-2-amino-2-deoxy-$\beta$-D-glucopyranosyl)-5-fluorouracil

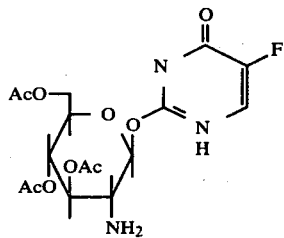

In 30 ml of anhydrous methanol was dissolved 507 mg (1 mmol.) of $O^4$-benzyl-$O^2$-(3,4,6-tri-O-acetyl-2-amino-2-deoxy-$\beta$-D-glucopyranosyl)-5-fluorouracil and after the atmosphere of the vessel for reduction was replaced with dried nitrogen 50 mg of 10% palladium-on-carbon was added thereto. The solution was reduced at room temperature until 23 ml of hydrogen gas was absorbed. After completion of the reaction, the catalyst was filtered off and the solvent was distilled under reduced pressure. To thus obtained residue was added anhydrous methanol and the mixture was concentrated under reduced pressure to give a precipitate, which was filtered, washed with anhydrous ethanol and dried to give 285 mg of the desired product, a white powder having a melting point of 103°–104° C.

Ultraviolet ray absorption spectrum: $\lambda_{max}^{MeOH}$ nm ($\epsilon$): 267 (6000)

NMR spectrum: $\delta$ (DMSO-$d_6$): 7.84 (d, H at 6-position, $J_{6H\text{-}F}$=3.7 cps), 5.97 (d, H at 1'-position, $J_{1'\text{-}2'}$=8.3 cps).

Elementary analysis: $C_{16}H_{20}O_9N_3F\cdot\frac{1}{2}H_2O$ Calculated: C, 45.07; H, 4.96; N, 9.86; F, 4.46 Found: C, 45.33; H, 5.33; N, 9.93; F, 3.92.

EXAMPLE 11e $O^4$-benzyl-$O^2$-(3,4,6-tri-O-acetyl-2-amino-2-deoxy-$\beta$-D-glucopyranosyl)-5-fluorouracil hydrochloric acid salt

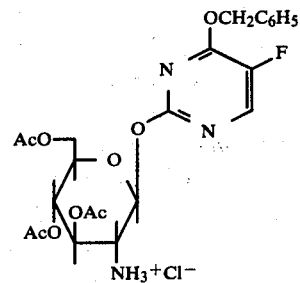

In a mixed solvent of 60 ml of acetone and 30 ml of ether was dissolved 9.3 g (18.3 mmol) of $O^4$-benzyl-$O^2$-(3,4,6-tri-O-acetyl-2-amino-2-deoxy-$\beta$-D-glucopyranosyl)-5-fluorouracil obtained by Example 9e, and an ether solution containing one equivalent of hydrochloric acid was added thereto with icecooling. After completion of the reaction, about 80 ml of acetone was added to the reaction mixture to give precipitated crystals, which were crushed, filtered out, washed with acetone and dried to give 8.5 g of the desired product, white crystals having a melting point of 157°–159° C. (decomp.)

Ultraviolet absorption spectrum: $\lambda_{max}^{MeOH}$ nm ($\epsilon$): 263 (7600)

NMR spectrum: $\delta$ (DMSO-$d_6$): 8.55 (d, H at 6-position, $J_{6H\text{-}F}$=2.5 cps), 6.57 (d, H at 1'-position, $J_{1'\text{-}2'}$=8.0 cps), 5.61 (s, —CH$_2$—C$_6$H$_5$)

Elementary analysis: $C_{23}H_{26}O_9N_3F\cdot HCl$ Calculated: C, 50.48; H, 5.00; N, 7.73; Cl, 6.51; F, 3.49 Found: C, 50.48; H, 5.03; N, 7.55; Cl, 6.50; F, 3.28.

EXAMPLE 12e $O^2$-(3,4,6-tri-O-acetyl-2-amino-2-deoxy-$\beta$-D-glucopyranosyl)-5-fluorouracil hydrochloric acid salt

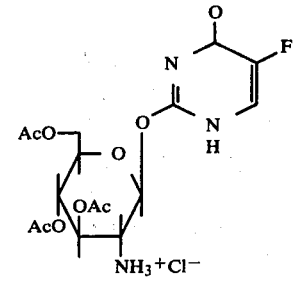

In 50 ml of anhydrous methanol was dissolved 544 mg (1 mmol.) of $O^4$-benzyl-$O^2$-(3,4,6-tri-O-acetyl-2-amino-2-deoxy-$\beta$-D-glucopyranosyl)-5-fluorouracil hydrochloric acid salt and the atmosphere of the vessel for reduction was replaced with dried nitrogen gas. After addition of 50 mg of 10% palladium-on-carbon, the resulting mixture was stirred at normal pressure until 21 ml of hydrogen gas was absorbed. After completion of the reaction, the catalyst was filtered off from the reaction mixture and the filtrate was concentrated under reduced pressure to give crystals, to which a small amount of anhydrous ethanol was added and distillation was continued. The thus obtained crystals were filtered out, washed with anhydrous ethanol and dried to give 304 mg of the desired product, white crystals having a melting point of 140°–148° C. (decomp.)

Ultraviolet absorption spectrum: $\lambda_{max}$ phosphate buffer (pH 6.86)nm ($\epsilon$): 266 (6000)

NMR spectrum: $\delta$ (DMSO-$d_6$): 7.94 (d, H at 6-position, $J_{6H-F}$=3.5 cps), 6.32 (d, H at 1'-position, $J_{1'-2'}$=8.0 cps)

Elementary analysis: $C_{16}H_{20}O_9N_3F \cdot HCl$ Calculated: C, 42.35; H, 4.66; N, 9.26; Cl, 7.81; F, 4.19 Found: C, 42.03; H, 4.56; N, 9.00; Cl, 7.77; F, 3.83.

EXAMPLE 13e $O^4$-benzyl-$O^2$-(2-amino-2-deoxy-$\beta$-D-glucopyranosyl)-5-fluorouracil

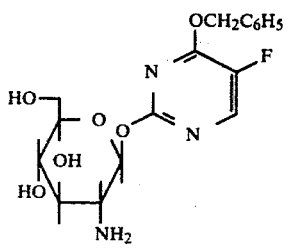

In 50 ml of anhydrous methanol was dissolved 2.18 g (4 mmol.) of $O^4$-benzyl-$O^2$-(3,4,6-tri-$O$-acetyl-2-amino-2-deoxy-$\beta$-D-glucopyranosyl)-5-fluorouracil hydrochloric acid salt obtained by Example 11e and the resulting mixture was cooled to $-30°$ C. Addition of 4 ml (one equivalent) of a solution of 1 N-sodium methoxide in methanol caused a white precipitate (free amino compound), which was dissolved by addition of 30 ml of methylene chloride. Then, 8 ml (2 equivalents) of a solution of 1 N-sodium methoxide in methanol was added thereto and the mixture was stirred at $-30°$ $\pm 5°$ C. for 3.5 hours. After cooling to $-40°$ C., 10 ml of anhydrous methanol containing 625 mg (10.4 mmol.) of acetic acid was added dropwise thereto and the mixture was distilled under reduced pressure to give a residue, to which 30 ml of 1 M-phosphoric acid buffer solution (pH, 6.5) was added to give crystals. These crystals were filtered out, washed with water and dried to give 1.53 g of the desired product, white crystals having a melting point of 116°–119° C.

Ultraviolet ray absorption spectrum: $\lambda_{max}^{0.1\ N-HCl}$nm ($\epsilon$): 262 (8100) $\lambda_{max}^{H_2O-MeOH}$ nm ($\epsilon$): 264 (7900) $\lambda_{max}^{0.1\ N-NaOH}$ nm ($\epsilon$): 265 (8000)

NMR spectrum: $\delta$ (DMSO-$d_6$): 8.50 (d, H at 6-position, $J_{6H-F}$=2.5 cps), 5.80 (d, H at 1'-position, $J_{1'-2'}$=8.5 cps), 5.55 (s, —$\underline{CH_2}$—$C_6H_5$)

Elementary analysis: $C_{17}H_{20}O_6N_3F \cdot 2H_2O \cdot \frac{1}{2}K_2HPO_4$ Calculated: C, 44.29; H, 5.30; N, 9.12; F, 4.12. Found: C, 43.76; H, 5.34; N, 9.58; F, 4.29

EXAMPLE 14e $O^2$-(2-amino-2-deoxy-$\beta$-D-glucopyranosyl)-5-fluorouracil

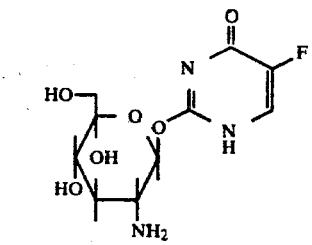

In 60 ml of anhydrous methanol was dissolved 762 mg (2 mmol.) of $O^4$-benzyl-$O^2$-(2-amino-2-deoxy-$\beta$-D-glucopyranosyl)-5-fluorouracil and the atmosphere of the vessel for reduction was replaced with dried nitrogen gas. After addition of 100 mg of 10% palladium-on-carbon, the resulting mixture was stirred at normal pressure until 46 ml of hydrogen gas was absorbed. After completion of the reaction, the catalyst was filtered off and the filtrate was concentrated under reduced pressure to give crystals, to which 40 ml of anhydrous ethanol was added. Continuation of distillation caused crystals, which were filtered out to give 516 mg of a raw product of the desired compound. These were dissolved in 80 ml of anhydrous methanol and the solution was concentrated after addition of 30 ml of anhydrous ethanol to give a powder, which was filtered out, washed with anhydrous ethanol and dried to give 283 mg of the desired product, a white powder-like pure substance having a melting point of 161°–165° C. (decomp.)

Ultraviolet ray absorption spectrum: $\lambda_{max}$ phosphate buffer (pH 6.86)nm ($\epsilon$): 267 (4400)

Elementary analysis: $C_{10}H_{14}O_6N_3F \cdot 4.5H_2O \cdot C_2H_5OH$. Calculated: C, 34.45; H, 5.90; N, 10.04; F, 4.54 Found: C, 34.68; H, 5.76; N, 9.53; F, 4.43.

The above-mentioned 5-fluorouracil compounds of the present invention exhibit remarkable anti-tumor activity according to pharmacological tests. Pharmacological test results concerning the anti-tumor activity are shown below in TABLES 1 through 4.

TABLE 1

| Anti-tumor activity against mouse leukemia L-1210[1] | | | | |
|---|---|---|---|---|
| Drugs | Dosage mg/Kg/day | Administration date[2] | Administration method | Average survival days (day) | Rate of increased survival days (%) |
| Compound[3] obtained in Example 3a | 50 | 1,2,3,4,6,7,8 and 9 | i.p. | 13.0 | 59 |
| | 100 | 1,2,3,4,6 and 7 | i.p. | 16.2 | 98 |
| | 200 | 1,2,3,4,6 and 7 | i.p. | 15.6 | 90 |
| Control | — | | | 8.2 | |
| Compound[3] obtained in Example 3a | 500 | 1 | i.p. | 11.8 | 57 |
| | 250 | 1 | i.p. | 9.6 | 28 |
| Control | — | | | 7.5 | |
| Compound[3] obtained in Example 3a | 1000 | 1 | p.o. | 14.6 | 74 |
| | 500 | 1 | p.o. | 11.6 | 38 |
| | 250 | 1 | p.o. | 8.8 | 5 |
| 5-FU[4] | 200 | 1 | p.o. | 13.2 | 57 |
| FT-207[5] | 1000 | 1 | p.o. | 14.0 | 67 |

TABLE 1-continued

Anti-tumor activity against mouse leukemia L-1210[1]

| Drugs | Dosage mg/Kg/day | Administration date[2] | Administration method | Average survival days (day) | Rate of increased survival days (%) |
|---|---|---|---|---|---|
| Control | — | | | 8.4 | |

[1]Cells of leukemia L-1210 (1 × 10⁵) were inoculated intraperitoneally into a BDF₁ mouse.
[2]Days are represented assuming that the day of inoculation of L-1210 is day zero. For instance, 6 represents the 6th day after inoculation.
[3]Compound of Example 3a: 1-(5-Fluoro-1H-2-oxo-pyrimidin-4-yl)-β-D-glucopyranouronic acid methyl ester
[4]5-FU: 5-Fluorouracil
[5]FT-207: N₁-(2-Tetrahydrofuryl)-5-fluorouracil

TABLE 2

Anti-tumor activity against mouse leukemia L-1210[1]

| Medicals | Dosage mg/kg/day | The day administered[2] | Administration method | Mean survival day | Increasing rate of survival days (%) |
|---|---|---|---|---|---|
| The compound obtained by Example 8b | 500 | 1 | Intraperitoneal | 15.0 | 88 |
| 5-FU[4] | 125 | 1 | Intraperitoneal | 15.0 | 88 |
| FT-207[5] | 400 | 1 | Intraperitoneal | 11.6 | 45 |
| Control | — | | | 8.0 | |
| The compound obtained by Example 8b | 500 | 1 | oral | 13.8 | 73 |
| Control | — | | | 8.0 | |

[1]Cells of leukemia L-1200 (1 × 10⁵) were transplanted into a peritoneum of mouse BDF₁.
[2]The transplanting day is represented as 0 day and 1 day means one day after the transplanting.
[3]The compound obtained in Example 8b: O⁴-(β-D-Glucopyranosyl)-5-fluorouracil
[4]5-FU: 5-Fluorouracil
[5]FT-207: N₁-(2-Tetrahydrofuryl)-5-fluorouracil

TABLE 3

Anti-tumor activity against mouse leukemia L-1210[1]

| Drugs | Dosage mg/Kg/day | Administration date[2] | Administration method | Average survival days (day) | Rate of increased survival days (%) |
|---|---|---|---|---|---|
| Compound[3] of Example 3c | 150 | 1-5 | i.p. | 11.5 | 35 |
| FT-207[5] | 100 | 1-5 | i.p. | 11.2 | 32 |
| Control | — | | | 8.5 | |
| Compound[4] of Example 7c | 500 | 1 | i.p. | 10.2 | 20 |
| FT-207 | 250 | 1 | i.p. | 10.4 | 22 |
| Control | — | | | 8.5 | |

[1]Cells of leukemia L-1210 (1 × 10⁵) were inoculated intraperitoneally into a BDF₁ mouse.
[2]Days are represented assuming that the day of inoculation of L-1210 is the day zero. For example, 5 represents the fifth day after inoculation.
[3]Compound of Example 3c: 1-(5-Fluoro-1H-4-oxopyrimidin-2-yl)-β-D-glucopyranouronic acid methyl ester
[4]Compound of Example 7c: 1-(5-Fluoro-1H-4-oxopyrimidin-2-yl)-β-D-glucopyranouronic acid amide.

TABLE 4

Anti-cancer activities against mouse leukemia L-1210[1]

| Medicals | Dosage mg/kg/day | The day administered[2] | Administration method | Mean survival day | Increasing rate of survival days (%) |
|---|---|---|---|---|---|
| The compound obtained by Example 3e[3] | 500 | 1 | Intraperitoneal | 13.0 | 78 |
| 5-FU[4] | 100 | 1 | Intraperitoneal | 13.2 | 81 |
| FT-207[5] | 400 | 1 | Intraperitoneal | 9.2 | 26 |
| Control | — | | | 7.3 | |
| The compound obtained by Example 12e | 500 | 1 | Intraperitoneal | 10.6 | 33 |
| 5-FU | 100 | 1 | Intraperitoneal | 13.8 | 73 |
| FT-207 | 400 | 1 | Intraperitoneal | 11.0 | 38 |
| Control | — | | | 8.0 | |

[1]Cells of leukemia L-1200 (1 × 10⁵) were transplanted into a peritoneum of mouse BDF₁
[2]The transplanting day is represented as 0 day and 1 day means one day after the transplantation.
[3]The compound obtained by Example 3e: O⁴-3,4,6-tri-O-acetyl-2-amino-2-deoxy-β-D-glucopyranosyl)-5-fluorouracil
[4]5-FU: 5-fluorouracil
[5]FT-207: N₁-(2-tetrahydrofuryl)-5-fluorouracil
[6]The compound obtained by Example 12: O²-(3,4,6-tri-O-acetyl-2-amino-2-deoxy-β-glucopyranosyl)-5-fluorouracil hydrochloric acid.

We claim:

1. A 5-Flourouracil compound having the formula

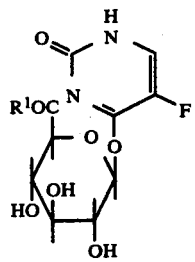

wherein $R^1$ represents a hydroxyl group, a $C_1$-$C_8$ alkoxy group, a $C_5$-$C_7$ cycloalkoxy group, a phenylalkyloxy having 1-2 carbon atoms in the alkyl moiety and the phenyl ring may be substituted with $C_1$-$C_4$ alkyl, $C_1$-$C_4$ alkoxy or halogen group, a phenyloxy group optionally substituted with $C_1$-$C_4$ alkyl, $C_1$-$C_4$ alkoxy or halogen or a group

in which $R^2$ and $R^3$ may be the same or different and each represents a hydrogen atom, a $C_1$-$C_5$ alkyl group, a $C_5$-$C_7$ cycloalkyl group, phenylalkyl having 1-2 carbon atoms in the alkyl moiety and the phenyl ring may be substituted with $C_1$-$C_4$ alkyl, $C_1$-$C_4$ alkoxy or halogen; phenyl, and phenyl substituted with $C_1$-$C_4$ alkyl, $C_1$-$C_4$ alkoxy or halogen or $R^2$ and $R^3$ may form 5-6 membered cyclic amino group.

2. A 5-Fluorouracil compound having the formula

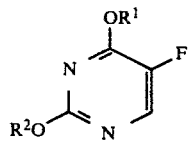

wherein $R^1$ and $R^2$, which are the same, each represents a β-D-glucopyranosyl, β-D-galactopyranosyl, β-D-ribopyranosyl or β-D-xylopyranosyl group, or one of $R^1$ and $R^2$ represents a β-D-glucopyranosyl, β-D-galactopyranosyl, β-D-ribopyranosyl or β-D-xylopyranosyl group and the other of $R^1$ and $R^2$ represents a hydrogen atom.

3. A 5-Fluorouracil compound having the formula

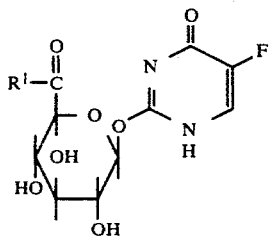

wherein $R^1$ represents a hydroxyl group, a $C_1$–$C_8$ alkoxy group, a $C_5$–$C_7$ cycloalkoxy group, a phenylalkyloxy having 1-2 carbon atoms in the alkyl moiety and the phenyl ring may be substituted with $C_1$–$C_4$ alkyl, $C_1$–$C_4$ alkoxy or halogen group, a phenyloxy group optionally substituted with $C_1$–$C_4$ alkyl, $C_1$–$C_4$ alkoxy or halogen or a group

in which $R^2$ and $R^3$ may be the same or different and each represents a hydrogen atom, a $C_1$–$C_4$ alkyl group, a $C_5$–$C_7$ cycloalkyl group, phenylalkyl having 1-2 carbon atoms in the alkyl moiety and the phenyl ring may be substituted with $C_1$–$C_4$ alkyl, $C_1$–$C_4$ alkoxy or halogen; phenyl, and phenyl substituted with $C_1$–$C_4$ alkyl, $C_1$–$C_4$ alkoxy or halogen or $R^2$ and $R^3$ may form 5-6 membered cyclic amino group.

4. A 5-Flourouracil compound having the formula

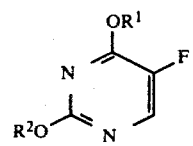

wherein one of $R^1$ and $R^2$ represents a group

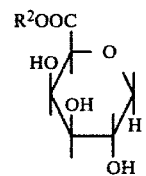

in which $R^3$ represents a hydrogen atom, a $C_1$–$C_8$ alkyl group, a $C_5$–$C_7$ cycloalkyl group, a phenylalkyl having 1-2 carbon atoms in the alkyl moiety and the phenyl ring may be substituted with $C_1$–$C_4$ alkyl, $C_1$–$C_4$ alkoxy or halogen; phenyl, and phenyl substituted with $C_1$–$C_4$ alkyl, $C_1$–$C_4$ alkoxy or halogen or $R^2$ and $R^3$ may form 5-6 membered cyclic amino group and the other represents a hydrogen atom.

5. A Flourouracil compound having the following formula and pharmaceutically acceptable salts thereof:

wherein one of $R^1$ and $R^2$ represents a group with the following formula:

wherein A represents a group having the following formulae:

wherein $R^3$ represents a hydrogen atom; a $C_1$–$C_5$ aliphatic acyl group; an aromatic acyl group, the aromatic group of which may be substituted with a $C_1$–$C_4$ alkyl group, a $C_1$–$C_4$ alkoxy group, or a halogen group; $R^4$ represents a hydrogen atom, a $C_1$–$C_8$ alkyl, a $C_5$–$C_7$ cycloalkyl, a phenylalkyl having 1-2 carbon atoms in the alkyl moiety and the phenyl ring may be substituted with $C_1$–$C_4$ alkyl, $C_1$–$C_4$ alkoxy, or halogen or phenyl, and phenyl substituted with $C_1$–$C_4$ alkyl, $C_1$–$C_4$ alkoxy or halogen and the other of $R^1$ and $R^2$ represents a hydrogen atom.

6. A 5-flourouracil compound selected from the group consisting of (Ia)

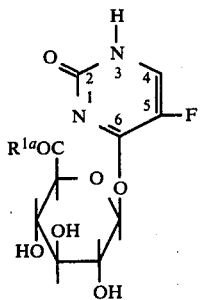

wherein $R^{1a}$ is hydroxy; alkoxy having from 1 to 8 carbon atoms; cycloalkoxy having from 5 to 7 carbon atoms; phenylalkyloxy which is unsubstituted or substituted with $C_1$ to $C_4$ alkyl, $C_1$ to $C_4$ alkoxy or halogen; phenyloxy, the phenyl ring of which may be substituted with $C_1$ to $C_4$ alkyl, $C_1$ to $C_4$ alkoxy or halogen; or

in which $R^{2a}$ and $R^{3a}$ are selected from the group consisting of (i) hydrogen, (ii) $C_1$ to $C_5$ alkyl, (iii) $C_5$ to $C_7$ cycloalkyl, (iv) phenylalkyl having 1-2 carbon atoms in the alkyl moiety and the phenyl ring may be substituted with $C_1$-$C_4$ alkyl, $C_1$-$C_4$ alkoxy or halogen, (v) phenyl which is unsubstituted or substituted with $C_1$-$C_4$ alkyl, $C_1$-$C_4$ alkoxy or halogen, and (vi) $R^{2a}$ and $R^{3a}$, together with the adjacent nitrogen atom, is a 5 or 6 membered cyclic amino group;

(Ib)

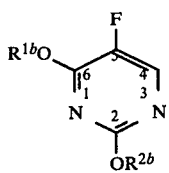

wherein $R^{1b}$ and $R^{2b}$ are the same and are selected from the group consisting of β-D-glucopyranosyl, β-D-galactopyranosyl, β-D-ribopyranosyl and β-D-xylopyranosyl, or one of $R^{1b}$ and $R^{2b}$ is so selected and the other of $R^{1b}$ and $R^{2b}$ is hydrogen;

(Ic)

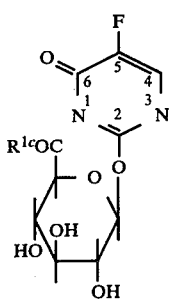

wherein $R^{1c}$ is hydroxy; $C_1$ to $C_8$ alkoxy; $C_5$ to $C_7$ cycloalkoxy; phenylalkyloxy having 1-2 carbon atoms in the alkyl moiety and the phenyl ring may be substituted with $C_1$ to $C_4$ alkyl, $C_1$ to $C_4$ alkoxy or halogen; aryl which is unsubstituted or substituted with $C_1$ to $C_4$ alkyl, $C_1$ to $C_4$ alkoxy or halogen; or

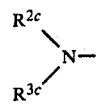

in which $R^{2c}$ and $R^{3c}$ are selected from the group consisting of (i) hydrogen, (ii) $C_1$ to $C_5$ alkyl, (iii) $C_5$ to $C_7$ cycloalkyl, (iv) phenylalkyl, the phenyl ring of which may be substituted with $C_1$ to $C_4$ alkyl, $C_1$ to $C_4$ alkoxy or halogen, (v) phenyl, and phenyl substituted with $C_1$ to $C_4$ alkyl, $C_1$ to $C_4$ alkoxy or halogen, and (vi) $R^{2c}$ and $R^{3c}$, together with the adjacent nitrogen atom, is a 5 or 6 membered cyclic amino group;

(Id)

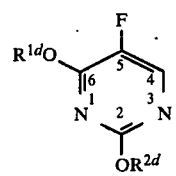

wherein one of $R^{1d}$ and $R^{2d}$ is a group of the formula

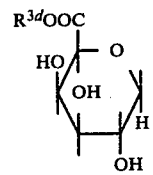

in which $R^{3d}$ is selected from the group consisting of (i) $C_1$ to $C_8$ alkyl, (ii) $C_5$ to $C_7$ cycloalkyl, (iii) phenylalkyl having 1-2 carbon atoms in the alkyl moiety and the phenyl ring may be substituted with $C_1$ to $C_4$ alkyl, $C_1$ to $C_4$ alkoxy or halogen, and (iv) phenyl, and phenyl substituted with $C_1$ to $C_4$ alkyl, $C_1$ to $C_4$ alkoxy or halogen; and the other of $R^{1d}$ and $R^{2d}$ is hydrogen; and (Ie)

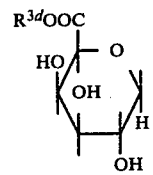

wherein one of $R^{1e}$ and $R^{2e}$ represents a group of the formula

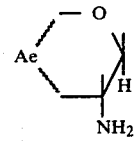

wherein Ae is a group of one of the following formulae

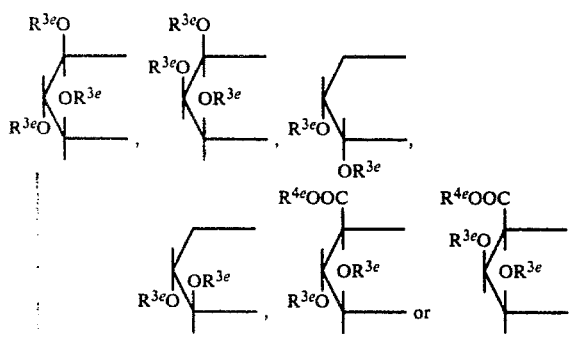

in which $R^{3e}$ is hydrogen, $C_1$ to $C_5$ aliphatic acyl, or aromatic acyl, the aromatic group of which may be substituted with $C_1$ to $C_4$ alkyl, $C_1$ to $C_4$ alkoxy or halogen; $R^{4e}$ is selected from the group consisting of (i) hydrogen, (ii) $C_1$ to $C_8$ alkyl, (iii) $C_5$ to $C_7$ cycloalkyl, (iv) phenylalkyl having 1-2 carbon atoms in the alkyl moiety and the phenyl ring may be substituted with $C_1$ to $C_4$ alkyl, $C_1$ to $C_4$ alkoxy or halogen, and (v) phenyl, and phenyl substituted with $C_1$ to $C_4$ alkyl, $C_1$ to $C_4$ alkoxy or halogen; and the other of $R^{1e}$ and $R^{2e}$ is hydrogen.

7. A compound of claim 6 of formula (Ia).
8. 1-(5-Fluoro-1H-2-oxo-pyrimidinyl-4-yl)-$\beta$-D-glucopyranouronic acid methyl ester of formula (Ia) of claim 6.
9. A compound of claim 6 of formula (Ib).
10. $O^4$-($\beta$-D-Glucopyranosyl)-5-flourouracil of formula (Ib) of claim 6.
11. A compound of claim 6 of formula (Ic).
12. 1-(5-Flouro-1H-4-oxopyrimidin-2-yl)-$\beta$-D-glucopyranouronic acid methyl ester of formula (Ic) of claim 6.
13. 1-(5-Flouro-1H-4-oxopyrimidin-2-yl)-$\beta$-D-glucopyranouronic acid amide of formula (Ic) of claim 6.
14. A compound of claim 6 of formula (Id).
15. 1-(2-Benzyloxy-5-fluoropyrimidin-4-yl)-2,3,4-tri-O-acetyl-$\beta$-D-galactopyranouronic acid methyl ester of formula (Id) of claim 6.
16. A compound of claim 6 of formula (Ie).
17. $O^4$-(3,4,6-tri-O-acetyl-2-amino-2-deoxy-$\beta$-D-glucopyranosyl)-5-flourouracil of formula (Ie) of claim 6.
18. $O^2$-(3,4,6-tri-O-acetyl-2-amino-2-deoxy-$\beta$-D-glucopyranosyl)-5-flourouracil hydrochloric acid salt of formula (Ie) of claim 6.

* * * * *

UNITED STATES PATENT AND TRADEMARK OFFICE
CERTIFICATE OF CORRECTION

PATENT NO. : 4,248,999　　　　　　　　　　　Page 1 of 2
DATED　　　 : February 3, 1981
INVENTOR(S) : TSUNEO BABA et al It is certified that error appears in the above—identified patent and that said Letters Patent is hereby corrected as shown below:

Column 6, line 13: rewrite "compunds" as --compounds--.

Column 37, line 63: rewrite "alochol" as --alcohol--.

Column 46, line 27: after "ester" delete "8d 1-(5-Fluoro-".

Column 46, line 28: before "1H-" insert --8d 1-(5-Fluoro- --.

Column 46, line 37: after "ester" delete "13d 1-(5-Fluoro-".

Column 46, line 38: before "1H-" insert --13d 1-(5-Fluoro- --.

Column 66, line 64: rewrite the entire line as follows
　　　　　--5.40　(s, $\underline{-CH_2}-C_6H_5$).

Column 73, line 65: replace "½$K_2HPO_4$" with --¼$K_2HPO_4$--.

UNITED STATES PATENT AND TRADEMARK OFFICE
CERTIFICATE OF CORRECTION

PATENT NO. : 4,248,999
DATED : February 3, 1981
INVENTOR(S) : TSUNEO BABA et al

It is certified that error appears in the above—identified patent and that said Letters Patent is hereby corrected as shown below:

Column 78, replace the formula appearing at the top of the column with the following:

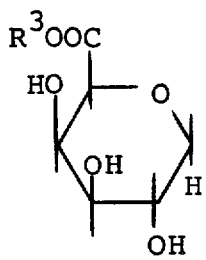

Title page, left column, under "Foreign Application Priority Data", delete "Oct. 28, 1976 [JP] Japan....51-130200".

Signed and Sealed this

First Day of March, 1988

*Attest:*

DONALD J. QUIGG

*Attesting Officer*     *Commissioner of Patents and Trademarks*